(12) United States Patent
Laniado et al.

(10) Patent No.: US 11,869,629 B2
(45) Date of Patent: *Jan. 9, 2024

(54) SYSTEMS AND METHODS FOR ARTIFICIAL INTELLIGENCE-GUIDED BIOMOLECULE DESIGN AND ASSESSMENT

(71) Applicant: Pythia Labs, INc., Culver City, CA (US)

(72) Inventors: Joshua Laniado, Los Angeles, CA (US); Julien Jorda, Los Angeles, CA (US); Matthias Maria Alessandro Malago, Santa Monica, CA (US); Thibault Marie Duplay, Los Angeles, CA (US); Mohamed El Hibouri, Los Angeles, CA (US); Lisa Juliette Madeleine Barel, Los Angeles, CA (US)

(73) Assignee: Pythia Labs, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/886,751

(22) Filed: Aug. 12, 2022

(65) Prior Publication Data

US 2023/0022022 A1 Jan. 26, 2023

Related U.S. Application Data

(63) Continuation of application No. 17/384,104, filed on Jul. 23, 2021, now Pat. No. 11,450,407.

(Continued)

(51) Int. Cl.
*G16B 15/20* (2019.01)
*G16B 35/00* (2019.01)
(Continued)

(52) U.S. Cl.
CPC ............. *G16B 15/20* (2019.02); *G16B 15/30* (2019.02); *G16B 35/00* (2019.02); *G16B 40/20* (2019.02)

(58) Field of Classification Search
CPC ........ G16B 15/20; G16B 15/30; G16B 15/00; G16B 99/00; G16C 20/30
See application file for complete search history.

(56) References Cited

U.S. PATENT DOCUMENTS

| 5,526,281 A | 6/1996 | Chapman et al. |
| 9,296,802 B2 | 3/2016 | Choi et al. |

(Continued)

FOREIGN PATENT DOCUMENTS

| EP | 3739589 A1 | 11/2020 |
| KR | 2021-0145059 A | 12/2021 |

(Continued)

OTHER PUBLICATIONS

Protein Sequence Design with a Learned Potential Namrata Anand, Raphael R. Eguchi, Alexander Derry, Russ B. Altman, Po-Ssu Huang bioRxiv 2020.01.06.895466; doi: https://doi.org/10.1101/2020.01.06.895466 (Year: 2020).*

(Continued)

*Primary Examiner* — Jesse P Frumkin
(74) *Attorney, Agent, or Firm* — Choate, Hall & Stewart LLP; William R. Haulbrook; Ronen Adato

(57) ABSTRACT

Described herein are systems and methods for designing and testing custom biologic molecules in silico which are useful, for example, for the treatment, prevention, and diagnosis of disease. In particular, in certain embodiments, the biomolecule engineering technologies described herein employ artificial intelligence (AI) software modules to accurately predict performance of candidate biomolecules and/or portions thereof with respect to particular design criteria. In (Continued)

certain embodiments, the AI-powered modules described herein determine performance scores with respect to design criteria such as binding to a particular target. AI-computed performance scores may, for example, be used as objective functions for computer implemented optimization routines that efficiently search a landscape of potential protein backbone orientations and binding interface amino-acid sequences. By virtue of their modular design, AI-powered scoring modules can be used separately, or in combination, such as in a pipeline approach where different structural features of a custom biologic are optimized in succession.

30 Claims, 57 Drawing Sheets

Related U.S. Application Data

(60) Provisional application No. 63/224,801, filed on Jul. 22, 2021.

(51) Int. Cl.
 *G16B 15/30* (2019.01)
 *G16B 40/20* (2019.01)

(56) References Cited

U.S. PATENT DOCUMENTS

| | | | |
|---|---|---|---|
| 9,373,059 B1 | 6/2016 | Heifets et al. | |
| 11,256,994 B1* | 2/2022 | Bucher | G06V 20/69 |
| 11,450,407 B1* | 9/2022 | Laniado | G16B 15/20 |
| 2002/0072864 A1 | 6/2002 | Lacroix et al. | |
| 2002/0133297 A1 | 9/2002 | Yang et al. | |
| 2002/0147547 A1 | 10/2002 | Desjarlais | |
| 2004/0199334 A1 | 10/2004 | Kovesdi et al. | |
| 2012/0239367 A1 | 9/2012 | Tong et al. | |
| 2013/0330335 A1 | 12/2013 | Bremel et al. | |
| 2016/0300127 A1 | 10/2016 | Heifets et al. | |
| 2018/0260517 A1* | 9/2018 | Blattner | G16B 15/00 |
| 2018/0285731 A1 | 10/2018 | Heifets et al. | |
| 2018/0341754 A1 | 11/2018 | Fan et al. | |
| 2019/0272887 A1 | 9/2019 | Feinberg et al. | |
| 2019/0325986 A1* | 10/2019 | Agarwal | G16B 15/30 |
| 2020/0342953 A1 | 10/2020 | Morrone et al. | |
| 2021/0304847 A1 | 9/2021 | Senior et al. | |
| 2022/0165366 A1 | 5/2022 | Zubarev et al. | |
| 2022/0375538 A1 | 11/2022 | Das et al. | |
| 2023/0034425 A1 | 2/2023 | Laniado et al. | |
| 2023/0040576 A1 | 2/2023 | Laniado et al. | |
| 2023/0083810 A1 | 3/2023 | Xu et al. | |

FOREIGN PATENT DOCUMENTS

| | | |
|---|---|---|
| WO | WO-2013/040142 A2 | 3/2013 |
| WO | WO-2018/213767 A1 | 11/2018 |
| WO | WO-2020/123302 A1 | 6/2020 |
| WO | WO-2023/004116 A1 | 1/2023 |

OTHER PUBLICATIONS

Satorras, V.G. et al., E(n) Equivariant Graph Neural Networks, Proc. 38th Int. Conf. Machine Learning, PMLR, 139, 10 pages, (2021).
Shrake, A. and Rupley, J.A., Environment and exposure to solvent of protein atoms. Lysozyme and insulin, J. Mol. Biol., 79(2):351-371 (1973).
Gainza, P. et al., De novo design of site-specific protein interactions with learned surface fingerprints, bioRxiv preprint, 41 pages, (2022).
Gainza, P. et al., Deciphering interaction fingerprints from protein molecular surfaces using geometric deep learning, Nat. Methods, 17(2):184-192 (2020).
International Search Report for PCT/US2022/038014, filed Jul. 22, 2022, 4 pages, (dated Nov. 15, 2022).
Senior, A.W. et al., Protein structure prediction using multiple deep neural networks in the 13th Critical Assessment of Protein Structure Prediction (CASP13), Proteins, 87(12):1141-1148 (2019).
Tien, M.Z. et al., Maximum allowed solvent accessibilites of residues in proteins, PLoS One, 8(11):e80635 (2013), 8 pages.
Written Opinion for PCT/US2022/038014, filed Jul. 22, 2022, 8 pages, (dated Nov. 15, 2022).
Ashtawy, Hossam Mohamed Farg., A Comparative Study of Machine-learning-based Scoring Functions in Predicting Protein-ligand Binding Affinity. Michigan State University. Electrical Engineering, 149 pages, (2011).
Cao, L. et. al., De novo design of picomolar SARS-COV-2 miniprotein inhibitors, Science, 370(6515):426-431, (2020).
Chevalier, A., et. al., Massively parallel de novo protein design for targeted therapeutics, Nature 550:74-79, (2017).
Collaborative Computational Project, No. 4, The CCP4 Suite: Programs for Protein Crystallography, Acta Crystallogr D Biol Crystallogr. D50:760-763 (1994).
Dauparas, J. et al., Robust deep learning based protein sequence design using ProteinMPNN, bioRxiv preprint, 33 pages, (2022).
Dhariwal, P. and Nichol, A., Diffusion models beat GANs on image synthesis, arXiv preprint, 44 pages, (2021).
Gorski, K.M., et. al., HEALPix—a Framework for high resolution discretization, and fast analysis of data distributed on the sphere, 622:759-771, (2005).
Hassan-Harrirou, H., et. al., RosENet: Improving Binding Affinity Prediction by Leveraging Molecular Mechanics Energies with an Ensemble of 3D Convolutional Neural Networks, J. Chem. Inf. Model, 60(6):2791-2802, (2020).
Hsu, C. et al., Learning inverse folding from millions of predicted structures, bioRxiv preprint, 22 pages, (2022).
Ingraham, J. et al., Generative Models for Graph-Based Protein Design, 33rd Conference on Neural Information Processing Systems (NeurIPS 2019), Vancouver, Canada, 12 pages, (2019). Retrieved online at: <https://proceedings.neurips.cc/paper/2019/hash/f3a4ff4839c56a5f460c88cce3666a2b-Abstract.html>.
Jiménez, J. et. al., KDEEP: Protein-Ligand Absolute Binding Affinity Prediction via 3D-Convolutional Neural Networks, J. Chem. Inf. Model, 58(2):287-296, (2018).
Liu, Y. et al., Rotamer-free protein sequence design based on deep learning and self-consistency, Nature Computational Science, 19 pages, (2022).
McPartlon, M. et al., A deep SE(3)-equivariant model for learning inverse protein folding, bioRxiv preprint, 18 pages, (2022).
Pierce, B.G., et.al., Accelerating Protein Docking in ZDOCK Using an Advanced 3D Convolution Library, PLoS ONE, e24657, 6(9):1-6, (2011).
Ragoza, M. et. al., Protein-Ligand Scoring with Convolutional Neural Networks, J. Chem. Inf. Model, 57(4):942-957, (2017).
Shapovalov, M.S., and Dunbrack, R.L., Jr., A smoothed backbone-dependent rotamer library for proteins derived from adaptive kernel density estimates and regressions, Structure, 19(6):844-858, <https://www.cell.com/structure/fulltext/S0969-2126(11)00144-4> (2011).
Strokach, A. et al., Fast and Flexible Protein Design Using Deep Graph Neural Networks, Cell Syst., 11(4):402-411, (2020).
The CCP4 Suite, Computer programs for protein crystallography, Overview and Manual, 130 pages, Feb. 2006.
Wallach, I., et. al., AtomNet: A Deep Convolutional Neural Network for Bioactivity Prediction in Structure-based Drug Discovery, 1-11, (2015).
Winn, M.D., et. al., Overview of the CCP4 suite and current developments, Acta Crystallogr. Section D, Biological Crystallography, ISSN 0907-4449, D67:235-242, (2011).
Yang, J. et al., Improved protein structure prediction using predicted interresidue orientations, Proc. Natl. Acad. Sci. USA, 117(3):1496-1503, (2020).
Yang, K. et al., Masked inverse folding with sequence transfer for protein representation learning, bioRxiv preprint, 16 pages, (2022).
Yershova, A., et. al., Generating uniform incremental grids on SO(3) Using the Hopf Fibration, The Internation Journal of Robotics Research, 29:(7):801-812, (2010).

(56) References Cited

OTHER PUBLICATIONS

Zhang, Z. et al., Protein representation learning by geometric structure pretraining, arXiv preprint, 25 pages, (2022).

Lim, J. et al., Scaffold-based molecular design with a graph generative model, arXiv:1905.1369, 33 pages, (2019).

Lim, J. et al., Scaffold-based molecular design with a graph generative model, Chem. Sci., 11(4):1153-1164 (2020).

Lipman, Y. et al., Flow Matching for Generative Modeling, arXiv Preprint, available online at <https://arxiv.org/abs/2210.02747v1>, 24 pages, (Oct. 6, 2022).

Vaswani, A. et al., Attention Is All You Need, arXiv Preprint, available online at https://arxiv.org/abs/1706.03762, 15 pages, (Dec. 6, 2017).

Anand, N. et al., Fully differentiable full-atom protein backbone generation, ICLR 2019 Workshop: Deep Generative Models for Highly Structured Data, 10 pages, (2019).

Andrusier, N. et al., Principles of flexible protein-protein docking, Proteins, 73(2):271-289 (2008).

Gray, J.J. et al., Protein-protein docking with simultaneous optimization of rigid-body displacement and side-chain conformations, J. Mol. Biol., 331(1):281-299 (2003).

Huang, S.Y., Search strategies and evaluation in protein-protein docking: principles, advances and challenges, Drug Discov. Today, 19(8):1081-1096 (2014).

Meng, X.Y. et al., Molecular docking: a powerful approach for structure-based drug discovery, Curr. Comput. Aided Drug Des., 7(2):146-157 (2011).

Zhou, P. et al., Computational peptidology: a new and promising approach to therapeutic peptide design, Curr. Med. Chem., 20(15):1985-1996 (2013).

\* cited by examiner

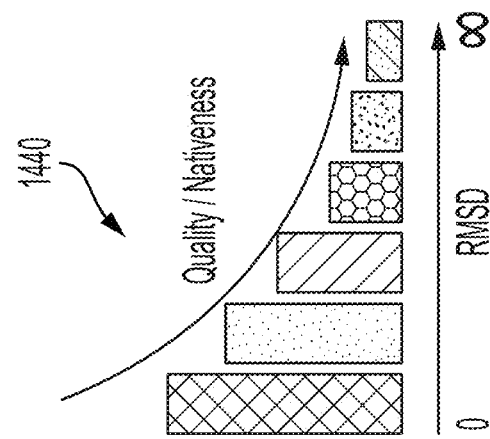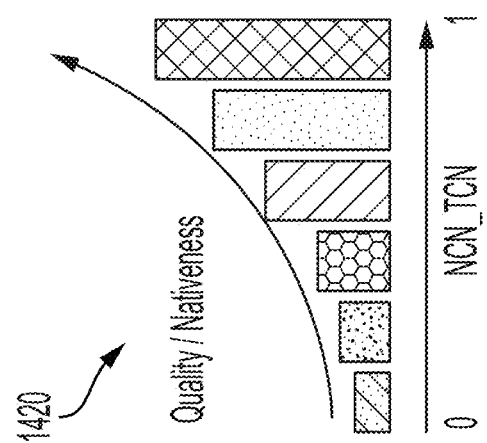
FIG. 14

FIG. 17

AA Type Sampling — 2902

For a given hotspot,
pick randomly a natural AA
that is not the wild-type one.

AA in natural interfaces are not uniformly distributed.
Random sampling utilizes frequencies of
AA in known interfaces
for each secondary structure type.

Rotamer Sampling — 2904

Once an AA is set, allowed rotamers for this
AA at the hotspot position are computed
based on the Dunbrack Rotamer Library.
Rotamers that induce clashes
with the rest of the molecule are excluded.
The Dunbrack library yields,
for each combination of AA
and phi/psi backbone torsion angles,
probabilities of rotamers that have
been derived from existing PDB structures

AA/SS Frequency Table

{'B': {'K': 5.7615, 'V': 6.4867, 'P':
4.996, 'L': 7.776, 'E': 5.6003, 'M':
3.4649, 'W': 2.9815, 'R': 9.3876, 'H':
3.1829, ... 'S': 6.9817, 'F': 4.0328, 'D':
7.4114, 'G': 6.2982}}

Dunbrack Library

| | | | | | | | | |
|---|---|---|---|---|---|---|---|---|
| ARG | -180 | -180 | 6 | 1 2 2 2 | 0.222369 | 64.5 | -177.8 | 178.6 | -174.7 ... |
| ARG | -180 | -180 | 6 | 1 2 2 1 | 0.190575 | 60.3 | 177.9 | 177.5 | 87.1 ... |
| ARG | -180 | -180 | 6 | 1 2 2 3 | 0.188392 | 64.3 | -174.0 | -175.6 | -68.2 ... |
| ARG | -180 | -180 | 6 | 1 2 1 2 | 0.090980 | 64.5 | -173.5 | 67.3 | -169.8 ... |
| ARG | -180 | -180 | 6 | 1 2 3 2 | 0.085782 | 63.5 | -177.5 | -67.1 | 172.5 ... |
| ARG | -180 | -180 | 6 | 1 2 1 1 | 0.051724 | 61.4 | 177.0 | 65.1 | 83.2 ... |
| ARG | -180 | -180 | 6 | 1 2 3 3 | 0.048664 | 62.9 | 180.0 | -69.2 | -82.5 ... |

FIG. 29

SYSTEMS AND METHODS FOR ARTIFICIAL INTELLIGENCE-GUIDED BIOMOLECULE DESIGN AND ASSESSMENT

CROSS-REFERENCE TO RELATED APPLICATIONS

This application is a continuation of U.S. application Ser. No. 17/384,104, filed Jul. 23, 2021, which claims priority to and benefit of U.S. provisional application No. 63/224,801, filed Jul. 22, 2021, the contents of which are hereby incorporated by reference in their entirety.

BACKGROUND

An increasing number of important drugs and vaccines are complex biomolecules referred to as biologics. For example, seven of the top ten best selling drugs as of early 2020 were biologics, including the monoclonal antibody adalimumab (Humira®). Biologics have much more complex structure than traditional small molecule drugs. The process of drug discovery, drug development, and clinical trials require an enormous amount of capital and time. Typically, new drug candidates undergo in vitro testing, in vivo testing, then clinical trials prior to approval.

Software tools for in silico design and testing of new drug candidates can cut the cost and time of the preclinical pipeline. However, biologics often have hard-to-predict properties and molecular behavior. To date, software and computational tools (including artificial intelligence (AI) and machine learning) have been applied primarily to small molecules, but, despite extensive algorithmic advances, have achieved little success in producing accurate predictions for biologics due to their complexity.

SUMMARY

Described herein are systems and methods for designing and testing custom biologic molecules in silico which are useful, for example, for the treatment, prevention, and diagnosis of disease. In particular, in certain embodiments, the biomolecule engineering technologies described herein employ artificial intelligence (AI) software modules to accurately predict performance of candidate biomolecules and/or portions thereof (e.g., amino acid backbones, sub-regions of interest, etc.) with respect to particular design criteria. In certain embodiments, the AI-powered modules described herein determine performance scores with respect to design criteria such as binding to a particular target, which may be an individual molecule, such as protein or peptide monomer, or a complex, for example formed by multiple protein and/or peptide sub-units. The AI-computed performance scores may, for example, be used as objective functions for computer implemented optimization routines that efficiently search a landscape of potential protein backbone orientations and binding interface amino-acid sequences. By virtue of their modular design, as described herein, AI-powered scoring modules can be used separately, or in combination with each other, such as in a pipeline approach where different structural features of a custom biologic are optimized in succession.

For example, presented herein is an AI-powered pipeline for engineering a custom biologic structure, said pipeline including (i) a scaffold docker, (ii) an interface designer, and (iii) a binding affinity predictor. The scaffold docker module determines favorable three-dimensional orientations—also referred to herein as "poses"—of candidate peptide backbones susceptible to interact with the target. In certain embodiments, candidate peptide backbones correspond to protein or peptide molecules with detailed structure of amino-acid side chains stripped away, and serve as molecular scaffolds that can be populated with amino acids to create a custom biologic structure. As such, these candidate peptide backbones together with the favorable poses determined via the scaffold docker module may be used as a starting point for the interface designer module, which is used to design an amino acid sequence a region of a candidate peptide backbone that is in proximity, and, accordingly, will influence binding to, the target. Positions along a particular candidate peptide backbone that, when occupied by amino acids, will be in proximity to the target are determined, for example, based on the geometry of a particular candidate peptide backbone and particular pose. The interface designer module populates these locations with amino acids, varying and evaluating different combinations of amino acid types and rotamers to generate candidate binding interfaces of the prospective biomolecule. In certain embodiments, a binding affinity predictor module is used to predict the binding affinity of each of a set of designed candidate interface regions to the target. The predicted binding affinities may be used to select a subset of the candidate interface regions, as well make additional refinements [e.g., by varying amino acids to modulate binding affinities (e.g., in an interactive fashion)], for use in creating a custom biologic structure for binding to the target.

The scaffold docker module uses a candidate scaffold model, which is a representation of a candidate peptide backbone (e.g., a backbone of a protein or peptide molecule). As described in further detail herein, scaffold models used to represent candidate peptide backbones may also include representations of one or more side chain atoms (e.g., atoms that are common to a plurality of types of amino acid side chains, such as a beta-carbon atoms). These retained side chain atoms may act as, for example, placeholders, identifying sites along a candidate peptide backbone that may be occupied by amino acids. Accordingly, in certain embodiments, candidate scaffold models may be generated from structural models of pre-existing proteins or peptides (e.g., having a previously determined crystallographic structure)], for example by stripping away portions of amino acid side chains [e.g., retaining only one or more (e.g., a single) side chain atoms, such as a beta carbon], or may be newly generated, for example via computational approaches. For a particular candidate scaffold model, the scaffold docker module generates a plurality of candidate poses with respect to the target ("docked poses") by rotating and/or translating the candidate scaffold model in three-dimensional space.

In certain embodiments, candidate poses are filtered based on an initial prediction of whether they are likely to create a sufficient level of interaction between the candidate scaffold model and target (e.g., between atoms of the candidate scaffold model and those of the target) and/or cause clashes (e.g., excessive spatial overlap). In certain embodiments, as described in further detail herein, a Fast Fourier Transform (FFT) and shape map representation approach can be used to efficiently evaluate candidate poses in this manner.

In certain embodiments, the scaffold docker module uses a machine learning algorithm to evaluate and score the candidate poses and identify favorable orientations. In certain embodiments, a particular candidate pose is used to generate a corresponding prospective scaffold-target complex model that represents at least a portion of a complex comprising the candidate peptide backbone and target, with the candidate peptide backbone oriented according to the particular pose with respect to the target. The machine learning algorithm receives the prospective scaffold-target complex model as input, and determines a scaffold-pose score that measures a likelihood that the scaffold-target complex model could represent to a viable, physically occurring complex. The scaffold-pose score is determined by the machine learning algorithm based on a training procedure whereby the machine learning algorithm is provided (i) representations of existing, physically viable complexes as well as (ii) artificially generated (e.g., computer generated), spurious, complexes that are not viable, and trained to differentiate between the two. In this manner, the scaffold docker module identifies favorable poses—i.e., three dimensional docked orientations of a candidate peptide backbone in complex with a target— by assessing how 'plausible' they appear, based on the model's training. Among other things, to Applicant's knowledge, a machine learning approach has not been previously applied in this manner—that is, in order to evaluate poses of and dock a scaffold model representing a candidate backbone, without a known amino acid sequence.

In certain embodiments, training data and the scaffold-target complex models received as input by the machine learning algorithm are three-dimensional volumetric data, such as electron density map (EDM) representations. In certain embodiments, the machine learning algorithm may utilize particular convolutional neural network (CNN) architectures. In particular, the present disclosure provides a spinal cord model (SCM) architecture that offers improved performance in capturing short-, middle- and long-range structural features of an interface (e.g., a protein-protein interface; e.g., a protein-peptide interface). These specialized features and approaches allow the machine learning algorithm of the scaffold docker module to evaluate candidate poses with a high degree of accuracy.

Accordingly, the scaffold docker module described herein utilizes (a) efficient sampling of the landscape of potential three-dimensional orientations of candidate peptide backbones for binding to a particular target along with (b) a specialized machine learning model trained to identify candidate peptide backbones and poses that are likely to be viable. In this manner, the scaffold docker module determines favorable orientations of candidate scaffolds for binding to a target.

In certain embodiments, once one or more favorable orientations—also referred to as docked poses—are determined (e.g., via the scaffold docker module), an interface designer module is used to design an amino acid sequence of a prospective ligand (e.g., protein and/or peptide) at an interface region that is in proximity to (e.g., and, accordingly, influences binding with) the target. In some embodiments, the interface designer module utilizes a machine learning algorithm that has been trained on a curated data set to accurately predict which interface sequences will be successful to bind the target. This training data set may include both existing, physically viable interfaces, for which structures have been experimentally determined, and also artificially generated (e.g., computer generated) mutant interfaces. In certain embodiments, mutant interfaces are generated by sampling both amino acid types as well as viable rotamers. Each interface is assigned a label that tallies the number of mutations and provides a measure of distance to an existing, physically viable interface. Interfaces—both existing and generated mutants—can be binned according to a number of mutations and the bins sampled uniformly to generate a large uniform dataset that serves as a foundation for training the machine learning algorithm to make accurate predictions.

Once trained, the machine learning algorithm of the interface designer module can be used to score candidate interfaces. In certain embodiments, the machine learning algorithm determines an interface score that represents a measure of a difference between the amino acid sequence of a prospective interface and an interface of an existing, physically viable complex [e.g., a physical complex with a known interface structure (e.g., amino-acid sequence)]. In certain embodiments, the interface score is a predicted number of mutations between the prospective interface and an existing, e.g., native interface. Prospective interfaces are thus assessed based on their similarity or dissimilarity to native, wild-type interfaces. Interfaces scored as having a higher degree of similarity to native complexes (e.g., a lower number of predicted mutations) are identified as more likely to be successful at binding the target and selected, for example to be evaluated further or synthesized.

In certain embodiments, as soon as one or more candidate interfaces are designed (e.g., via the interface designer module), a binding affinity predictor module is used to predict the binding affinity of each candidate interface to the target. The predicted binding affinities can then be used to rank candidate interfaces, e.g., to select those with highest predicted binding affinities for synthesis or further evaluation. Predicting binding affinities for large protein-protein complexes is challenging in comparison with small-molecule binding predictions. Proteins are larger and more complex than small molecules and protein binding data is also less extensive, resulting in a smaller data set. Moreover, protein binding affinity data can be highly unbalanced since it relies on experimentally determined affinity values (e.g., $K_d$, $K_i$, or logarithms thereof, such as $pK_d$), which presents a challenge to providing suitable training data for machine learning techniques.

In certain embodiments, to address this challenge and allow for AI-based prediction of binding affinities, training approaches described herein include methods for balancing the dataset across a range of experimental $pK_d$ values via clustering and differential augmentation techniques.

Approaches described herein also may include a pre-training technique (also referred to as transfer learning) whereby the architecture of the machine learning model utilized by the binding affinity predictor module matches an architecture of a model implemented in another, different, module. Among other things, this allows model weights obtained when training the other machine learning model to be used as a starting point (e.g., pre-training) for binding affinity prediction. For example, in certain embodiments, both the scaffold docker module and the binding affinity predictor module utilize machine models that implement the SCM architecture described herein. Once the scaffold docker module's SCM is trained, its weights can be transferred to the binding affinity predictor's SCM. These initial weights are then adjusted by training the binding affinity predictor's SCM on experimentally determined binding affinity data. Among other things, this pre-training approach addresses challenges associated with the limited size of binding affinity data sets by leveraging training performed to accomplish a different (e.g., and, in certain embodiments, easier), but related, task.

Accordingly, the approaches described herein provide accurate predictions of biomolecule performance in a flexible modular framework that can be used to engineer and design custom biologics in-silico. In this manner, these tools disclosed herein can facilitate drug development, cutting the cost and time of the preclinical pipeline and improving the speed and efficiency with which new therapies are created and brought to market.

In one aspect, the invention is directed to a method for designing a custom biologic structure for binding to a target (e.g., a target molecule and/or complex) via an artificial intelligence (AI)-powered scaffold docker module, the method comprising: (a) receiving and/or generating, by a processor of a computing device, a candidate scaffold model, wherein the candidate scaffold model is a representation (e.g., a 3D representation) of a candidate peptide backbone; (b) generating, by the processor, for the candidate scaffold model, one or more (e.g., a plurality of) prospective scaffold-target complex models, each representing at least a portion of a complex comprising the candidate peptide backbone [e.g., or a variation thereof (e.g., variations accounting for backbone flexibility)] at a particular pose (e.g., three-dimensional orientation) with respect to the target; (c) for each of the one or more (e.g., plurality of) prospective scaffold-target complex models, determining, by the processor, a scaffold pose score using a machine learning model that receives, as input, a volumetric representation of at least a portion of (e.g., an extracted interface of) a particular prospective scaffold-target complex model and outputs, for the particular scaffold-target complex model, as the scaffold pose score, a value representing a measure of plausibility (e.g., quantifying a prediction, by the machine learning model) [e.g., a likelihood value representing a predicted probability or indicative thereof (e.g., not necessarily bounded between 0 and 1)] that the particular prospective scaffold-target complex model represents a native complex [e.g., such that the scaffold pose score value represents a measure of plausibility (e.g., a degree to which the scaffold-target complex model is 'native-like') of the candidate peptide backbone and pose represented by the scaffold-target complex model, as determined by the machine learning model; e.g., wherein the scaffold pose score is a measure of similarity between the scaffold target complex and representations of native complexes], thereby determining one or more (e.g., a plurality of) scaffold pose scores; (d) selecting, by the processor, a subset of the one or more (e.g., plurality of) prospective scaffold-target complex models using the determined one or more (e.g., plurality of) scaffold pose scores; and (e) providing (e.g., by the processor) the selected subset of prospective scaffold-target complex models for use in designing the custom biologic structure and/or using the selected subset of prospective scaffold-target complex models to design the custom biologic structure.

In certain embodiments, the method further comprises performing steps (a) to (d) for each of a plurality of candidate scaffold models [e.g., selected from a library of scaffold models; e.g., based on a library of protein structure models (e.g., experimentally determined structures)], wherein step (e) comprises designing the custom biologic structure for binding to the target molecule using the determined scaffold scores (e.g., testing multiple candidate scaffolds each in multiple orientations with respect to the target molecule).

In certain embodiments, step (b) comprises adjusting one or more regions of the candidate scaffold to represent variations in (e.g., portions of) the candidate peptide backbone accounting for backbone flexibility.

In certain embodiments, the candidate peptide backbone has a length of less than about 100 peptide bonds [e.g., less than about 50 peptide bonds (e.g., less than about 20 peptide bonds)] (e.g., the candidate peptide backbone has a relatively short length, commensurate with a peptide).

In certain embodiments, the candidate peptide backbone has a length of greater than about 20 peptide bonds [e.g., greater than about 50 peptide bonds (e.g., greater than about 100 peptide bonds)] (e.g., the candidate peptide backbone is relatively long, commensurate with a protein).

In certain embodiments, the candidate peptide backbone is a backbone of a pre-existing protein molecule (e.g., for which a crystallographic structure has been previously determined).

In certain embodiments, the candidate scaffold model corresponds to a model of a backbone of a template biologic (e.g., a protein or peptide) [e.g., from a database (e.g., Protein Data Bank (PDB))] {e.g., the candidate scaffold model having been generated, and/or wherein step (a) comprises generating the candidate scaffold model, by: receiving and/or accessing a structural model of a template biologic (e.g., a protein or peptide) [e.g., from a database (e.g., Protein Data Bank (PDB))]; and extracting, from the structural model, a model of a backbone of the template biologic [e.g., by stripping at least a portion of amino acid side chain atoms (e.g., retaining a first side chain atom, such as a beta-carbon)] to generate the candidate scaffold model}.

In certain embodiments, the template biologic comprises at least one of a native peptide, a native protein, an engineered protein, and an engineered peptide.

In certain embodiments, the candidate scaffold model is a computationally generated model (e.g., representing a candidate peptide backbone not necessarily occurring in nature).

In certain embodiments, step (b) comprises applying one or more (e.g., a plurality of) three-dimensional rotational transforms to the candidate scaffold model, wherein the one or more (e.g., plurality of) rotational transformations are sampled uniformly from a rotational space (e.g., using Hopf Fibration).

In certain embodiments, step (b) comprises generating a shape map representation for the scaffold and target molecule, wherein atoms are labeled based on their solvent-accessible surface area (e.g., labeled as surface or core according to their solvent-accessible surface area (SASA) value) (e.g., and performing a cross-correlation via a FFT to distinguish poses that do not cause contact, poses that do cause contact, and clashes).

In certain embodiments, the method comprises, for each particular prospective scaffold-target complex model of the one or more (e.g., plurality of) prospective scaffold-target complex models: receiving and/or generating, by the processor, a simulated three-dimensional electron density map (3D EDM) corresponding to (e.g., generated from) at least a portion of the particular prospective scaffold-target complex model; and using the simulated 3D EDM as the volumetric representation of the particular prospective scaffold-target complex model input to the machine learning model.

In certain embodiments, the method comprises identifying, by the processor, an interface sub-region of the particular prospective scaffold-target complex model, the interface sub-region comprising representations of atoms of the candidate peptide backbone and/or target located in proximity to an interface between the candidate peptide backbone and/or target.

In certain embodiments, identifying the interface sub-region comprises: identifying, as hotspots of the candidate peptide backbone, atoms (e.g., beta-carbons) of the candidate peptide backbone located within a threshold distance from an atom (e.g., a beta-carbon) of the target; identifying, as hotspots of the target molecule, atoms (e.g., beta-carbons) of the target located within a threshold distance from an atom (e.g., a beta-carbon) of the candidate peptide backbone; and determining, as the interface sub-region, a portion of the scaffold-target complex model representing [e.g., comprising (e.g., only) representations of and/or bonds between] the hotspots of the candidate peptide backbone and the hotspots of the target.

In certain embodiments, the method further comprises: identifying, as context atoms and/or residues of the candidate peptide backbone and/or target, atoms and/or residues of the candidate peptide backbone and/or target adjacent (e.g., bound) to a hotspot; and expanding the interface sub-region to incorporate the context atoms of the candidate peptide backbone and/or target.

In certain embodiments, the volumetric representation received by the machine learning model as input is a simulated 3D EDM.

In certain embodiments, the machine learning model comprises a neural network [e.g., a convolutional neural network (CNN)].

In certain embodiments, the machine learning model is a trained model (e.g., a binary classifier model), having been trained (e.g., using training data) to determine a value representing a measure of plausibility of a particular volumetric representation (e.g., 3D EDM) of a scaffold-target complex model received as input (e.g., wherein the value is a measure of whether the particular volumetric representation represents a plausible (e.g., a native (e.g., wild-type) complex) (e.g., a likelihood value, representing a predicted probability).

In certain embodiments, the machine learning model has been trained (e.g., parameter values of the machine learning model established) using training data comprising: (A) a plurality of native complex models, each native complex models representing at least a portion of a native complex based on [e.g., and determined from (e.g., allowing for perturbations)] an experimentally determined structural model of the native complex; and (B) a plurality of artificially generated variant complex models, each variant complex model based on (e.g., generated from) structural models of one or more native ligands (e.g., proteins and/or peptides) and/or complexes thereof {e.g., each variant complex generated by one or more of (i), (ii), and (iii) (including combinations thereof) as follows: (i) wherein each of at least a portion (e.g., up to all) of the variant complex models are generated from a structural model of a native complex by identifying a ligand portion and a target portion of the native complex and applying one or more 3D rotation/translation operations to a representation of the ligand portion to generate a variant complex model that represents a variant of the native complex in which the ligand portion is at a different (e.g., new, artificial) 3D orientation with respect to the target portion; (ii) wherein each of at least a portion (e.g., up to all) of the variant complex models are generated by combining (e.g., two or more) monomeric structural models to generate variant complex models that represent combinations of monomers oriented [e.g., and applying one or more 3D rotation/translations] at various poses with respect to each other; and (iii) wherein each of at least a portion (e.g., up to all) of the variant complexes are generated from a structural model of a native complex by altering a representation of a backbone of one or more of its constituent molecules}.

In certain embodiments, the method comprises using, by the processor, a (e.g., computer implemented) optimization routine (e.g., simulated annealing) to select the subset of scaffold-target complex models (e.g., using the determined scaffold pose scores) [e.g., wherein steps (c) and/or (d) comprise using the determined scaffold pose scores as an objective function in a computer implemented optimization routine].

In certain embodiments, the target (e.g., molecule and/or complex) comprises a peptide and/or complex thereof.

In certain embodiments, the target (e.g., molecule and/or complex) comprises a protein and/or complex thereof (e.g., a dimer, trimer, etc.).

In another aspect, the invention is directed to a method for designing a custom biologic structure for binding to a target (e.g., a target molecule and/or complex) via an artificial intelligence (AI)-powered interface designer module, the method comprising: (a) receiving and/or generating, by a processor of a computing device, a candidate scaffold-target complex model representing a candidate peptide backbone at a particular pose (e.g., three dimensional orientation) with respect to the target; (b) receiving and/or generating, by the processor, one or more (e.g., a plurality of) prospective ligand-target complex models each representing a prospective ligand (e.g., protein and/or peptide) corresponding to the candidate peptide backbone [e.g., the prospective ligand having a peptide backbone corresponding to the selected candidate peptide backbone (e.g., wherein the peptide backbone of the prospective ligand is the selected candidate backbone or a version thereof (e.g., that accounts for backbone flexibility, e.g., variation/movement in one or more flexible regions))] (i) comprising at least an interface region located in proximity to the target populated with amino acids and (ii) positioned with respect to the target based on the particular pose {e.g., wherein a pose of the prospective ligand with respect to the target is a modified version of the particular pose, accounting for backbone flexibility and/or allowing for rigid body perturbations (e.g., random perturbations) [e.g., minor translations and/or rotations [e.g., translations within about 10 angstroms or less (e.g., about 5 angstroms or less, about 1 angstrom or less, about 0.5 angstroms or less) along one or more directions (e.g., an x-, y-, or z-, direction) and/or rotations of approximately 15 degrees or less (e.g., approximately 5 degrees or less, e.g., approximately one or two degrees or less about one or more axes (e.g., x- and/or y- and/or z-axis))]]}, each prospective ligand having a particular (e.g., distinct) amino acid population at its interface region [e.g., a particular (e.g., distinct) combination (e.g., sequence) of amino acids and/or rotamers thereof at the interface region of the prospective ligand]; (c) for each of the one or more prospective ligand-target complex models, determining, by the processor, an interface score using a machine learning model that receives, as input, a volumetric representation of a particular prospective ligand-target complex model and outputs, for the particular prospective interface-target complex model, as the interface score, a measure of similarity and/or dissimilarity between an interface of the particular prospective ligand-target complex model and representations of native interfaces [e.g., such that the interface score represents a measure of plausibility (e.g., a degree to which the ligand-target complex model is 'native-like', e.g., and/or is likely to form a viable complex when tested experimentally) of the amino acid interface represented by the ligand-target complex model, as determined by the machine learning model] [e.g., such that the interface score represents a measure of distance (e.g., a predicted number of amino acid mutations) between the interface of the particular prospective ligand-target complex and representations of native interfaces], thereby determining one or more (e.g., a plurality of) interface scores; (d) selecting, by the processor, a subset of the prospective ligand-target complex models based on the one or more (e.g., plurality of) interface scores; and (e) providing (e.g., by the processor) the selected subset of prospective ligand-target complex models for use in designing the custom biologic structure for binding to the target and/or designing the custom biologic structure for binding to the target using the selected subset of prospective ligand-target complex models.

In certain embodiments, the method further comprises performing steps (a) to (d) for each of a plurality of candidate scaffold-target complex models.

In certain embodiments, each of at least a portion of the one or more (e.g., plurality of) candidate scaffold-target complex models represent a same candidate peptide backbone at a different particular pose with respect to the target molecule.

In certain embodiments, each of at least a portion of the one or more (e.g., plurality of) candidate scaffold-target complex models represent a different candidate peptide backbone in complex with the target molecule.

In certain embodiments, the a candidate scaffold-target complex model is a member of a subset of prospective scaffold-target complex models determined using an artificial intelligence (AI) powered scaffold docker module (e.g., that performs the method of any one of various aspects and embodiments described herein).

In certain embodiments, step (b) comprises assigning an initial amino acid sequence to an interface region of the candidate peptide backbone (e.g., a randomly generate amino acid sequence; e.g., based on a native protein or peptide from which the candidate peptide backbone was derived) and mutating amino acids to generate, for each prospective ligand-target complex models, the particular amino acid population at the interface region of the prospective ligand.

In certain embodiments, the method comprises, for each particular prospective ligand-target complex model of the one or more (e.g., plurality of) prospective ligand-target complex models: receiving and/or generating, by the processor, a simulated three-dimensional electron density map (3D EDM) corresponding to (e.g., generated from) at least a portion of the particular prospective ligand-target complex model; and using the simulated 3D EDM as the volumetric representation of the particular prospective ligand-target complex model input to the machine learning model.

In certain embodiments, the method comprises identifying, by the processor, an interface sub-region of the particular prospective ligand-target complex model, the interface sub-region comprising representations of atoms of the prospective ligand and/or target located in proximity to an interface between the prospective ligand and target.

In certain embodiments, identifying the interface sub-region comprises: identifying, as hotspots of the prospective ligand, residues of the prospective ligand located within a threshold distance from a residue of the target; identifying, as hotspots of the target molecule, residues of the target located within a threshold distance from a residue of the prospective ligand; and determining, as the interface sub-region, a portion of the ligand-target complex model representing [e.g., comprising (e.g., only) representations of and/or bonds between] the hotspots of the prospective ligand and the hotspots of the target.

In certain embodiments, the method further comprises: identifying, as context atoms and/or residues of the prospective ligand and/or target, atoms and/or residues of the prospective ligand and/or target adjacent (e.g., bound) to a hotspot; and expanding the interface sub-region to incorporate the context atoms and/or residues of the prospective ligand and/or target.

In certain embodiments, the volumetric representation received by the machine learning model as input comprises a simulated 3D EDM.

In certain embodiments, the machine learning model comprises a neural network [e.g., a convolutional neural network (CNN)].

In certain embodiments, the machine learning model is a trained model (e.g., a regression model), having been trained (e.g., using training data) to determine (e.g., as the measure of similarity and/or dissimilarity) a predicted number of mutations between (i) an interface that a particular volumetric representation (e.g., 3D EDM) of at least a portion of a ligand-target complex model received as input represents and (ii) representations of native interfaces.

In certain embodiments, the machine learning model has been trained (e.g., parameter values of the machine learning model established) using training data comprising: (A) a plurality of native interface models, each native interface models representing at least a portion of a native interface based on (e.g., and determined/derived from) an experimentally determined structural model of the native interface; (B) a plurality of artificially generated mutant interface models, each mutant interface model based on a mutated version of a native interface [e.g., generated from a structural model of a native interface by mutating amino acids of the native interface (e.g., changing an amino acid type and/or rotamer)].

In certain embodiments, the method comprises using, by the processor, a (e.g., computer implemented) optimization routine (e.g., simulated annealing) to select the subset of the prospective ligand-target complex models [e.g., wherein steps (c) and/or (d) comprise using the determined interface scores as an objective function in a computer implemented optimization routine].

In another aspect, the invention is directed to a method for engineering a custom biologic structure for binding to a target (e.g., target molecule and/or complex), via an artificial intelligence (AI) powered binding affinity predictor module, the method comprising: (a) receiving and/or generating, by a processor of a computing device, one or more prospective ligand-target complex models, each representing at least a portion of a complex comprising a prospective (e.g., custom) biologic and the target, with the prospective (e.g., custom) biologic positioned at a particular pose (e.g., three-dimensional orientation) with respect to the target; and (b) for each of the one or more prospective ligand-target complex models, determining, by the processor, a binding affinity score using a machine learning model that receives, as input, a volumetric representation of a particular ligand-target complex model (e.g., determined using the method of various aspects and/or embodiments described herein, for example with respect to various artificial intelligence (AI)-powered scaffold docker modules and/or artificial intelligence (AI)-powered interface designer modules for designing a custom biologic structure for binding to a target (e.g., a target molecule and/or complex), described herein) and outputs, as the binding affinity score, a value representing a predicted binding affinity between the prospective (e.g., custom) biologic and the target molecule of the particular ligand-target complex model.

In certain embodiments, the method comprises performing steps (a) and (b) for a plurality of ligand-target complex models, thereby determining a plurality of binding affinity scores and: (c) selecting, by the processor, a subset of the prospective ligand-target complex models based on the plurality of binding affinity scores; and (d) designing a custom biologic structure using the selected subset of prospective biologic-target complex modules.

In certain embodiments, step (c) comprises selecting, as the subset, those prospective ligand-target complexes having binding affinity scores greater than a particular binding affinity threshold value, thereby selecting a high binding affinity subset.

In certain embodiments, step (c) comprises ranking the prospective ligand-target complexes according to the plurality of binding affinity scores and selecting the subset based on the ranking [e.g., selecting, as the subset, a portion of the ligand-target complexes having a higher binding affinity score than others (e.g., a top 1, top 2, top 5, etc.; e.g., a top 10%, a top quartile, etc.)].

In certain embodiments, the method comprises: performing steps (a) and (b) for an initial set of one or more ligand-target complex models, to determine an initial set of binding affinity scores; and (e.g., iteratively) updating ligand-target complex models of the initial set to, for each ligand-target complex model, mutate amino acids (e.g., type and/or rotamer) of the custom biologic and/or the target molecule, to generate a set of mutated ligand-target complex models and performing step (b) for the set of the mutated ligand-target complex models to determine an updated set of binding affinity scores [e.g., and comparing the updated set of binding affinity scores with the initial set of binding affinity scores (e.g., to predict stabilizing and/or destabilizing mutations; e.g., to predict changes in binding affinity after mutation; e.g., to tune/modulate (e.g., increase or decrease) binding affinity))].

In certain embodiments, the binding affinity score is a predicted dissociation constant (e.g., pKd) value.

In another aspect, the invention is directed to a method for engineering a custom biologic structure for binding to a target molecule in silico, the method comprising: (a) receiving and/or generating, by a processor of a computing device, one or more candidate scaffolds models, wherein each of the one or more candidate scaffold models is a representation of a candidate peptide backbone; (b) determining, by the processor, based on the one or more candidate scaffold models, a set of one or more prospective scaffold-target complex models using a scaffold docker module (e.g., a machine learning software module, e.g., software that performs a method of any aspects and/or embodiments described herein, for example, various methods for designing a custom biologic structure for binding to a target (e.g., a target molecule and/or complex) via an artificial intelligence (AI)-powered scaffold docker module, described herein); (c) determining, by the processor, based on at least one member of the set of prospective scaffold-target complex models, a set of prospective ligand-target complex models using an interface designer module (e.g., a machine learning software module, e.g., software that performs a method of any aspects and/or embodiments described herein, for example, various methods for designing a custom biologic structure for binding to a target (e.g., a target molecule and/or complex) via an artificial intelligence (AI)-powered interface designer module, described herein); and (d) providing (e.g., by the processor) the set of prospective scaffold-target complex models and/or the set of prospective ligand target complex models for use in designing the custom biologic structure for binding to the target molecule and/or designing the custom biologic structure using the determined set of prospective ligand-target complex models and/or the set of prospective scaffold-target complex models.

In certain embodiments, step (d) comprises: determining, by the processor, for each of at least a portion of the set of prospective ligand-target complex models and/or the set of prospective scaffold-target complex models, predicted binding affinity score using a binding affinity predictor module (e.g., a machine learning software module, e.g., software that performs a method of any aspects or embodiments described herein, for example, various methods for designing a custom biologic structure for binding to a target (e.g., target molecule and/or complex), via an artificial intelligence (AI) powered binding affinity predictor module, described herein); and using the set of predicted binding affinity scores to design the custom biologic structure (e.g., to identify high-binding affinity biologic structures).

In certain embodiments, each of the scaffold docker module and the interface designer module comprises a machine learning software module.

In another aspect, the invention is directed to a method for determining and/or evaluating a predicted structure of a biologic complex, the method comprising: (a) receiving and/or generating, by the processor, one or more biologic complex models each representing a complex comprising a first biologic positioned at a (e.g., distinct) particular pose (e.g., 3D orientation) with respect to a second biologic; (b) for each of the one or more biologic complex models, determining, by the processor, a pose score using a machine learning model that receives, as input, a volumetric representation of a particular biologic complex model and outputs, for the particular biologic complex model, as the pose score, a value representing a measure of plausibility [e.g., likelihood value representing a predicted probability or indicative thereof (e.g., not necessarily bounded between 0 and 1)] that the particular biologic complex model represents a native complex [e.g., such that the scaffold pose score value represents a measure of plausibility (e.g., a degree to which the scaffold-target complex model is 'native-like') of the pose represented by the biologic complex model, as determined by the machine learning model; e.g., wherein the scaffold pose score is a measure of similarity between the scaffold target complex and representations of native complexes], thereby determining one or more pose scores; (c) selecting, by the processor, a subset of the one or more (e.g., plurality of) biologic complex models using the determined one or more (e.g., plurality of) pose scores; and (d) storing and/or providing, by the processor, the selected subset for display and/or further processing.

In certain embodiments, each of the one or more biologic complex models comprises: a first biologic model representing at least a portion of the first biologic; and a second biologic model representing at least a portion of the second biologic.

In certain embodiments, the first biologic model is a scaffold model representing a backbone of the first biologic (e.g., and omitting at least a portion of amino acid side-chain atoms); and/or the second biologic model is a scaffold model representing a backbone of the second biologic (e.g., and omitting at least a portion of amino acid side-chain atoms).

In certain embodiments, both the first and second biologic models are scaffold models.

In certain embodiments, the first biologic model includes representations of at least a portion of amino-acid side chains of the first biologic (e.g., within an sub-region in proximity to the second biologic; e.g., over the entire first biologic) (e.g., is a ligand model, having at least a portion populated with amino acids); and/or the second biologic model includes representations of at least a portion of amino-acid side chains of the second biologic (e.g., within an sub-region in proximity to the first biologic; e.g., over the entire second biologic) (e.g., is a ligand model, having at least a portion populated with amino acids).

In certain embodiments, both the first and second biologic models include representations of at least a portion of amino acid side chains of the respective biologic that they represent.

In certain embodiments, the method further comprises using the selected subset of biologic complex models as an initial starting point for one or more physics-based (e.g., force-field; e.g., energy functional) docking routines.

In certain embodiments, step (a) comprises receiving the one or more biologic complex models, and the received one or more biologic complex models having been determined using one or more physics-based docking routines.

In another aspect, the invention is directed to a method for determining a predicted structure of a biologic complex, the method comprising: (a) receiving and/or generating, by the processor, one or more biologic complex models, each representing a complex comprising a first biologic having a first amino acid sequence and positioned at a particular pose (e.g., 3D orientation) with respect to a second biologic having a second amino acid sequence; (b) for each of the one or more biologic complex models, determining, by the processor, an sequence score using a machine learning model that receives, as input, a volumetric representation of a particular biologic complex model and outputs, for the particular biologic complex model, as the sequence score, a measure of similarity and/or dissimilarity between an interface between the first and second biologic [e.g., the interface formed first and second amino acid sequences of the particular biologic complex in combination, e.g., including spatial relationships] and representations of native interfaces [e.g., such that the sequence score represents a measure of plausibility (e.g., a degree to which the biologic complex model is 'native-like') of the amino acid sequences represented by the biologic complex model, as determined by the machine learning model] [e.g., such that the sequence score represents a measure of distance (e.g., a predicted number of amino acid mutations) between the interface of the particular prospective ligand-target complex and representations of native interfaces]; (c) selecting, by the processor, a subset of the one or more (e.g., a plurality of) biologic complex models using the determined one or more (e.g., a plurality of) sequence scores; and (d) storing and/or providing, by the processor, the selected subset for display and/or further processing.

In certain embodiments, step (a) comprises receiving and/or generating a plurality of biologic complex models wherein, for each particular biologic complex model, the first biologic is a distinct first biologic (e.g., having a distinct first amino acid sequence).

In certain embodiments, for each particular biologic complex model, the second biologic is a same second biologic (e.g., having a same second amino acid sequence).

In certain embodiments, for each particular biologic complex model, the second biologic is a distinct second biologic (e.g., having a distinct second amino acid sequence).

In certain embodiments, step (a) comprises varying the first and/or second amino acid sequence to generate a plurality of distinct biologic complex models.

In certain embodiments, variations in the first amino acid sequence are restricted to a portion of the first amino acid sequence that corresponds to an interface sub-region of the first biologic in proximity to the second biologic; and/or variations in the second amino acid sequence are restricted to a portion of the second amino acid sequence that corresponds to an interface sub-region of the second biologic in proximity to the first biologic.

In certain embodiments, variations in the first and/or second amino acid sequences are not limited to an interface sub-region of the first and/or second biologic, such that the method provides for designing an entire biologic (e.g., not just an interface; e.g., a complete protein or peptide).

In another aspect, the invention is directed to a pipeline (e.g., a computer architecture pipeline) for designing custom biologic structures in silico, said pipeline comprising a plurality of AI-powered modules, wherein each module in the pipeline optimizes candidate custom biologic structural features with respect to a particular criteria [e.g., using a machine learning model that receives, as input, a representation of the candidate custom biologic structural features and generates, as output, a score representing a measure of performance with respect to the particular criteria].

In another aspect, the invention is directed to a system comprising: a processor of a computing device; and a memory having instructions stored thereon, wherein the instructions, when executed by the processor, cause the processor to perform the method of any one of the aspects and/or embodiments described herein.

In another aspect, the invention is directed to a method for designing a custom biologic structure for binding to a target (e.g., a target molecule and/or complex) in-silico via a pipeline of artificial intelligence (AI)-powered modules, the method comprising: (a) receiving and/or generating, by a processor of a computing device, one or more (e.g., a plurality of) prospective scaffold-target complex models (e.g., 3D representations), each representing at least a portion of a complex comprising a candidate peptide backbone [e.g., at least a portion of the scaffold-target complex models representing a same candidate peptide backbone and/or variations thereof (e.g., variations accounting for backbone flexibility) at various different poses; e.g., at least a portion of the scaffold-target complex models representing distinct candidate peptide backbones, e.g., so as to evaluate a library of different candidate peptide backbones] at a particular pose (e.g., three-dimensional orientation) with respect to the target; (b) for each of the one or more (e.g., plurality of) prospective scaffold-target complex models, determining, by the processor, a scaffold pose score using a first machine learning model, thereby determining one or more (e.g., a plurality of) scaffold pose scores; (c) selecting, by the processor, a scaffold-target complex model of the one or more (e.g., plurality of) prospective scaffold-target complex models using the determined one or more (e.g., plurality of) scaffold pose scores, thereby identifying a selected candidate peptide backbone and a selected pose represented by the selected scaffold-target complex model as a backbone and pose on which to build a custom interface portion of a ligand for binding to the target molecule; (d) generating, by the processor, based on the selected scaffold-target complex model, one or more (e.g., a plurality of) prospective ligand-target complex models (e.g., 3D representations), each representing a prospective ligand (e.g., protein and/or peptide) corresponding to the selected candidate peptide backbone [e.g., the prospective ligand having a peptide backbone corresponding to the selected candidate peptide backbone (e.g., wherein the peptide backbone of the prospective ligand is the selected candidate backbone or a version thereof (e.g., that accounts for backbone flexibility, e.g., variation/movement in one or more flexible regions))] (i) comprising at least an interface region located in proximity to the target populated with amino acids and (ii) positioned with respect to the target based on the selected pose {e.g., wherein a pose of the prospective ligand with respect to the target is a modified version of the selected pose, accounting for backbone flexibility and/or allowing for rigid body perturbations (e.g., random perturbations) [e.g., minor translations and/or rotations [e.g., translations within 10 angstroms or less (e.g., 5 angstroms or less, 1 angstrom or less, 0.5 angstroms or less) along one or more directions (e.g., an x-, y-, or z-, direction) and/or rotations of 15 degrees or less (e.g., 5 degrees or less, e.g., about one or two degrees or less about one or more axes (e.g., x- and/or y- and/or z-axis))]]}, each prospective ligand comprising a particular (e.g., distinct) amino acid population at its interface region [e.g., a particular (e.g., distinct) combination (e.g., sequence) of amino acids and/or rotamers thereof at the interface region of the prospective ligand]; (e) for each of the one or more (e.g., plurality) prospective ligand-target complex models, determining, by the processor, an interface score using a second machine learning model, thereby determining one or more (e.g., a plurality) of interface scores; (f) selecting, by the processor, a subset of the prospective ligand-target complex models based on at least a portion of the one or more (e.g., plurality of) interface scores; and (g) providing (e.g., by the processor) the selected subset of prospective ligand-target complex models for use in designing the custom biologic structure for binding to the target and/or designing the custom biologic structure for binding to the target using the selected subset of prospective ligand-target complex models.

In certain embodiments, the candidate peptide backbone comprises a length of less than about 100 peptide bonds [e.g., less than about 50 peptide bonds (e.g., less than about 20 peptide bonds)] (e.g., the candidate peptide backbone has a relatively short length, commensurate with a peptide).

In certain embodiments, the candidate peptide backbone comprises a length of greater than about 20 peptide bonds [e.g., greater than about 50 peptide bonds (e.g., greater than about 100 peptide bonds)] (e.g., the candidate peptide backbone is relatively long, commensurate with a protein).

In certain embodiments, the candidate peptide backbone is a backbone of a pre-existing protein molecule (e.g., for which a crystallographic structure has been previously determined).

In certain embodiments, step (a) comprises receiving and/or generating a candidate scaffold model representing at least a portion of the candidate peptide backbone, wherein the candidate scaffold model corresponds to a model of a backbone of a template biologic (e.g., a protein or peptide) [e.g., from a database (e.g., Protein Data Bank (PDB))] {e.g., the candidate scaffold having been generated, and/or wherein step (a) comprises generating the candidate scaffold model, by: receiving and/or accessing a structural model of a template biologic (e.g., a protein or peptide) [e.g., from a database (e.g., Protein Data Bank (PDB))]; and extracting, from the structural model, a model of a backbone of the template biologic [e.g., by stripping at least a portion of amino acid side chain atoms (e.g., retaining a first side chain atom, such as a beta-carbon)] to generate the candidate scaffold model}.

In certain embodiments, the template biologic comprises at least one of a wild-type peptide, a wild-type protein, an engineered protein, and an engineered peptide.

In certain embodiments, step (a) comprises receiving a computationally generated candidate scaffold model and/or generating a candidate scaffold model representing the candidate peptide backbone via a computational approach (e.g., thereby representing a candidate peptide backbone not necessarily occurring in nature).

In certain embodiments, step (a) comprises applying a one or more (e.g., plurality of) three-dimensional rotational transforms to a candidate scaffold model representing the candidate peptide backbone, wherein the one or more (e.g., plurality of) three-dimensional rotational transformations are sampled uniformly from a rotational space (e.g., using Hopf Fibration).

In certain embodiments, step (a) comprises generating a shape map representation for each of the candidate peptide backbone and the target molecule, the shape map representation comprising representations of atoms that are labeled based on their solvent-accessible surface area (e.g., labeled as surface or core according to their solvent-accessible surface area (SASA) value) (e.g., and performing a cross-correlation via FFT to distinguish poses that do not cause contact, poses that do cause contact, and clashes).

In certain embodiments, the first machine learning model receives, as input, for each particular prospective scaffold-target complex model, a volumetric representation of at least a portion of (e.g., an extracted interface of) the particular prospective scaffold-target complex model and outputs, for the particular scaffold-target complex model, as the scaffold pose score, a value representing a measure of plausibility (e.g., quantifying a prediction, by the first machine learning model) [e.g., a likelihood value representing a predicted probability or indicative thereof (e.g., not necessarily bounded between 0 and 1)] that the particular prospective scaffold-target complex model represents a native complex [e.g., such that the scaffold pose score represents a measure of plausibility (e.g., a degree to which the scaffold-target complex model is 'native-like') of the candidate peptide backbone and pose represented by the scaffold-target complex model, as determined by the machine learning model; e.g., wherein the scaffold pose score is a measure of similarity between the scaffold target complex and representations of native complexes], thereby determining the one or more (e.g., plurality of) scaffold pose scores.

In certain embodiments, the method comprises, for each particular prospective scaffold-target complex model of the one or more (e.g., plurality of) prospective scaffold-target complex models: receiving and/or generating, by the processor, a simulated three-dimensional electron density map (3D EDM) corresponding to (e.g., generated from) at least a portion of the particular prospective scaffold-target complex model; and using the simulated 3D EDM as the volumetric representation of the particular prospective scaffold-target complex model input to the first machine learning model.

In certain embodiments, the method comprises identifying, by the processor, an interface sub-region of the particular prospective scaffold-target complex model, the interface sub-region comprising representations of atoms of the candidate peptide backbone and/or target located in proximity to an interface between the candidate peptide backbone and/or target.

In certain embodiments, the first machine learning model is a trained model (e.g., a binary classifier model), having been trained (e.g., using training data) to determine a value representing a measure of plausibility of a particular volumetric representation (e.g., 3D EDM) of a scaffold-target complex model received as input (e.g., wherein the value is a measure of whether the particular volumetric representation represents a plausible (e.g., a native (e.g., wild-type) complex) (e.g., a likelihood value, representing a predicted probability).

In certain embodiments, the first machine learning model has been trained (e.g., parameter values of the machine learning model established) using training data comprising: (A) a plurality of native complex models, each native complex models representing at least a portion of a native complex based on [e.g., and determined from (e.g., allowing for perturbations)] an experimentally determined structural model of the native complex; and (B) a plurality of artificially generated variant complex models, each variant complex model based on (e.g., generated from) structural models of one or more native ligands and/or complexes thereof {e.g., each variant complex generated by one or more of (i), (ii), and (iii) (including combinations thereof) as follows: (i) wherein each of at least a portion (e.g., up to all) of the variant complex models are generated from a structural model of a native complex by identifying a ligand portion and a target portion of the native complex and applying one or more 3D rotation/translation operations to a representation of the ligand portion to generate a variant complex model that represents a variant of the native complex in which the ligand portion is at a different (e.g., new, artificial) 3D orientation with respect to the target portion; (ii) wherein each of at least a portion (e.g., up to all) of the variant complex models are generated by combining (e.g., two or more) monomeric structural models to generate variant complex models that represent combinations of monomers oriented [e.g., and applying one or more 3D rotation/translations] at various poses with respect to each other; and (iii) wherein each of at least a portion (e.g., up to all) of the variant complexes are generated from a structural model of a native complex by altering a representation of a backbone of one or more of its constituent molecules}.

In certain embodiments, step (d) comprises assigning an initial amino acid sequence to an interface region of the candidate peptide backbone (e.g., a randomly generated amino acid sequence; e.g., based on a native protein or peptide from which the candidate peptide backbone was derived) and mutating amino acids to generate, for each prospective ligand-target complex model, the particular amino acid population at the interface region of the prospective ligand.

In certain embodiments, the second machine learning model receives, as input, for each particular prospective ligand-target complex model, a volumetric representation of at least a portion of the particular prospective ligand-target complex model and outputs, for the particular prospective ligand-target complex model, as the interface score, a measure of similarity and/or dissimilarity between an interface of the particular prospective ligand-target complex model and representations of native interfaces [e.g., such that the interface score represents a measure of plausibility (e.g., a degree to which the ligand-target complex model is 'native-like', e.g., and/or is likely to form a viable complex when tested experimentally) of the amino acid interface represented by the ligand-target complex model, as determined by the machine learning model][e.g., such that the interface score represents a measure of distance (e.g., a predicted number of amino acid mutations) between the particular prospective ligand-target complex and a native complex].

In certain embodiments, the second machine learning model is a trained model (e.g., a regression model), having been trained (e.g., using training data) to determine (e.g., as the measure of similarity and/or dissimilarity) a predicted number of mutations between (i) an interface that a particular volumetric representation (e.g., 3D EDM) of at least a portion of a ligand-target complex model received as input represents and (ii) representations of native interfaces.

In certain embodiments, the second machine learning model has been trained (e.g., parameter values of the machine learning model established) using training data comprising: (A) a plurality of native interface models, each native interface models representing at least a portion of a native interface based on (e.g., determined/derived from) an experimentally determined structural model of the native interface; and (B) a plurality of artificially generated mutant interface models, each mutant interface model based on a mutated version of a native interface [e.g., generated from a structural model of a native interface by mutating amino acids of the native interface (e.g., changing an amino acid type and/or rotamer)].

In certain embodiments, at least one of the first machine learning model and the second machine learning model comprises a neural network [e.g., a convolutional neural network (CNN)].

In certain embodiments, the method comprises: using, by the processor, a (e.g., computer implemented) optimization routine (e.g., simulated annealing) to select the scaffold-target complex model of the prospective scaffold-target complex models using the determined scaffold pose scores [e.g., wherein steps (b) and/or (c) comprise using the determined scaffold pose scores as an objective function in a computer implemented optimization routine]; and/or using, by the processor, a (e.g., computer implemented) optimization routine (e.g., simulated annealing) to select the subset of the prospective ligand-target complex models [e.g., wherein steps (e) and/or (f) comprise using the determined interface scores as an objective function in a computer implemented optimization routine].

In certain embodiments, the target (e.g., molecule and/or complex) comprises is a peptide and/or complex thereof.

In certain embodiments, the target (e.g., molecule and/or complex) comprises a protein and/or a protein complex (e.g., a dimer, trimer, etc.).

In certain embodiments, the method further comprises: for each of at least a portion of the subset of the prospective ligand-target complex models determined at step (f), determining, by the processor, a binding affinity score using a third machine learning model that receives, as input, a volumetric representation of at least a portion of a particular ligand-target complex model and outputs, as the binding affinity score, a value representing a predicted binding affinity between the prospective custom biologic structure and the target molecule of the particular ligand-target complex model; and at step (g), using the one or more binding affinity scores to design the custom biologic structure.

In certain embodiments, the method comprises: selecting one or more high binding affinity ligand-target complex models based on the one or more binding affinity scores; and providing the one or more high binding affinity ligand-target complex models for use in designing the custom biologic structure and/or designing the custom biologic structure using the one or more high binding affinity ligand-target complex models.

In certain embodiments, the method comprises comparing the one or more binding affinity scores to a threshold value.

In certain embodiments, the method comprises ranking the prospective ligand target-complex models of the subset determined at step (f) according to the one or more determined binding affinity scores.

In certain embodiments, the binding affinity score is a predicted dissociation constant (e.g., a pKd value).

In certain embodiments, the third machine learning model comprises a neural network (e.g., a CNN).

In another aspect, the invention is directed to a system for designing a custom biologic structure for binding to a target (e.g., a target molecule and/or complex) in-silico via a pipeline of artificial intelligence (AI)-powered modules, the system comprising: a processor of a computing device; and a memory having instructions stored thereon, wherein the instructions, when executed by the processor, cause the processor to: (a) receive and/or generate one or more (e.g., a plurality of) prospective scaffold-target complex models, each representing at least a portion of a complex comprising a candidate peptide backbone at a particular pose (e.g., three-dimensional orientation) with respect to the target [e.g., at least a portion of the scaffold-target complex models representing a same candidate peptide backbone and/or variations thereof (e.g., variations accounting for backbone flexibility) at various different poses; e.g., at least a portion of the scaffold-target complex models representing distinct candidate peptide backbones, e.g., so as to evaluate a library of different candidate peptide backbones]; (b) for each of the one or more (e.g., plurality of) prospective scaffold-target complex models, determine a scaffold pose score using a first machine learning model, thereby determining one or more (e.g., a plurality of) scaffold pose scores; (c) select a scaffold-target complex model of the one or more (e.g., plurality of) prospective scaffold-target complex models using the determined one or more (e.g., plurality of) scaffold pose scores, thereby identifying a selected candidate peptide backbone and a selected pose represented by the selected scaffold-target complex model as a backbone and pose on which to build a custom interface portion of a ligand for binding to the target molecule; (d) generate, based on the selected scaffold-target complex model, one or more (e.g., a plurality of) prospective ligand-target complex models, each representing a prospective ligand (e.g., protein and/or peptide) corresponding to the selected candidate peptide backbone [e.g., the prospective ligand having a peptide backbone corresponding to the selected candidate peptide backbone (e.g., wherein the peptide backbone of the prospective ligand is the selected candidate backbone or a version thereof (e.g., that accounts for backbone flexibility, e.g., variation/movement in one or more flexible regions))] (i) comprising at least an interface region located in proximity to the target molecule populated with amino acids and (ii) positioned with respect to the target based on the selected pose {e.g., wherein a pose of the prospective ligand with respect to the target is a modified version of the selected pose, accounting for backbone flexibility and/or allowing for rigid body perturbations (e.g., random perturbations) [e.g., minor translations and/or rotations [e.g., translations within 10 angstroms or less (e.g., 5 angstroms or less, 1 angstrom or less, 0.5 angstroms or less) along one or more directions (e.g., an x-, y, or z-, direction) and/or rotations of 15 degrees or less (e.g., 5 degrees or less, e.g., about one or two degrees or less about one or more axes (e.g., x- and/or y- and/or z-axis))]]}, each prospective ligand comprising a particular (e.g., distinct) amino acid population at its interface region [e.g., a particular (e.g., distinct) combination (e.g., sequence) of amino acids and/or rotamers thereof at the interface region of the prospective ligand]; (e) for each of the one or more (e.g., plurality of) prospective ligand-target complex models, determine an interface score using a second machine learning model, thereby determining one or more (e.g., a plurality of) interface scores; (f) select a subset of the prospective ligand-target complex models based on the one or more (e.g., plurality of) interface scores; and (g) provide the selected subset of prospective ligand-target complex models for use in designing the custom biologic structure for binding to the target and/or design the custom biologic structure for binding to the target using the selected subset of prospective ligand-target complex models.

In another aspect, the invention is directed to a method for designing a custom biologic structure for binding to a target (e.g., a target molecule and/or complex) via an artificial intelligence (AI)-powered scaffold docker module, the method comprising: (a) receiving and/or generating, by a processor of a computing device, a candidate scaffold model, wherein the candidate scaffold model is a representation (e.g., a 3D representation) of a candidate peptide backbone; (b) generating, by the processor, for the candidate scaffold model, one or more (e.g., a plurality of) prospective scaffold-target complex models, each representing at least a portion of a complex comprising the candidate peptide backbone [e.g., or a variation thereof (e.g., variations accounting for backbone flexibility); e.g., wherein step (b) comprises adjusting one or more regions of the candidate scaffold to represent variations in (e.g., portions of) the candidate peptide backbone accounting for backbone flexibility] at a particular pose (e.g., three-dimensional orientation) with respect to the target; (c) for each of the one or more (e.g., plurality of) prospective scaffold-target complex models, determining, by the processor, a scaffold pose score using a machine learning model that receives, as input, a volumetric representation of at least a portion of (e.g., an extracted interface of) a particular prospective scaffold-target complex model and outputs, for the particular scaffold-target complex model, as the scaffold pose score, a value representing a measure of plausibility (e.g., quantifying a prediction, by the machine learning model) [e.g., a likelihood value representing a predicted probability or indicative thereof (e.g., not necessarily bounded between 0 and 1)] that the particular prospective scaffold-target complex model represents a native complex [e.g., such that the scaffold pose score value represents a measure of plausibility (e.g., a degree to which the scaffold-target complex model is 'native-like') of the candidate peptide backbone and pose represented by the scaffold-target complex model, as determined by the machine learning model; e.g., wherein the scaffold pose score is a measure of similarity between the scaffold target complex and representations of native complexes], thereby determining one or more (e.g., a plurality of) scaffold pose scores; (d) selecting, by the processor, a subset of the one or more (e.g., plurality of) prospective scaffold-target complex models using the determined one or more (e.g., plurality of) scaffold pose scores; and (e) providing (e.g., by the processor) the selected subset of prospective scaffold-target complex models for use in designing the custom biologic structure and/or using the selected subset of prospective scaffold-target complex models to design the custom biologic structure.

Features of embodiments described with respect to one aspect of the invention may be applied with respect to another aspect of the invention.

Throughout the description, where devices, systems, procedures, and/or methods are described as having, including, or comprising specific components, or where methods are described as having, including, or comprising specific steps, it is contemplated that, additionally, there are devices, systems, procedures, and/or methods of the present disclosure that consist essentially of, or consist of, the recited components, and that there are methods according to the present disclosure that consist essentially of, or consist of, the recited processing steps.

It should be understood that the order of steps or order for performing certain actions is immaterial as long as the method remains operable. Moreover, two or more steps or actions may be conducted simultaneously.

The following description is for illustration and exemplification of the disclosure only, and is not intended to limit the disclosure to the specific embodiments described.

The mention herein of any publication, for example, in the Background section, is not an admission that the publication serves as prior art with respect to any of the present claims. The Background section is presented for purposes of clarity and is not meant as a description of prior art with respect to any claim.

BRIEF DESCRIPTION OF THE DRAWING

The foregoing and other objects, aspects, features, and advantages of the present disclosure will become more apparent and better understood by referring to the following description taken in conjunction with the accompanying drawing, in which:

FIG. 14 is a pair of illustrative graphs showing variation in two pose quality metrics for different types of complexes, according to an illustrative embodiment.

FIG. 17 is a schematic illustrating an example sampling process, according to an illustrative embodiment.

FIG. 19C continues from FIG. 19B.

FIG. 19D continues from FIG. 19C.

FIG. 19E continues from FIG. 19D.

FIG. 19F continues from FIG. 19E.

FIG. 19G continues from FIG. 19F.

FIG. 19H continues from FIG. 19G.

FIG. 19I continues from FIG. 19H.

FIG. 19J continues from FIG. 19I.

FIG. 19K continues from FIG. 19J.

FIG. 19L continues from FIG. 19K.

FIG. 29 is a schematic diagram illustrating approaches for mutating amino acid side chains to create candidate interfaces, according to an illustrative embodiment.

Figure 2:
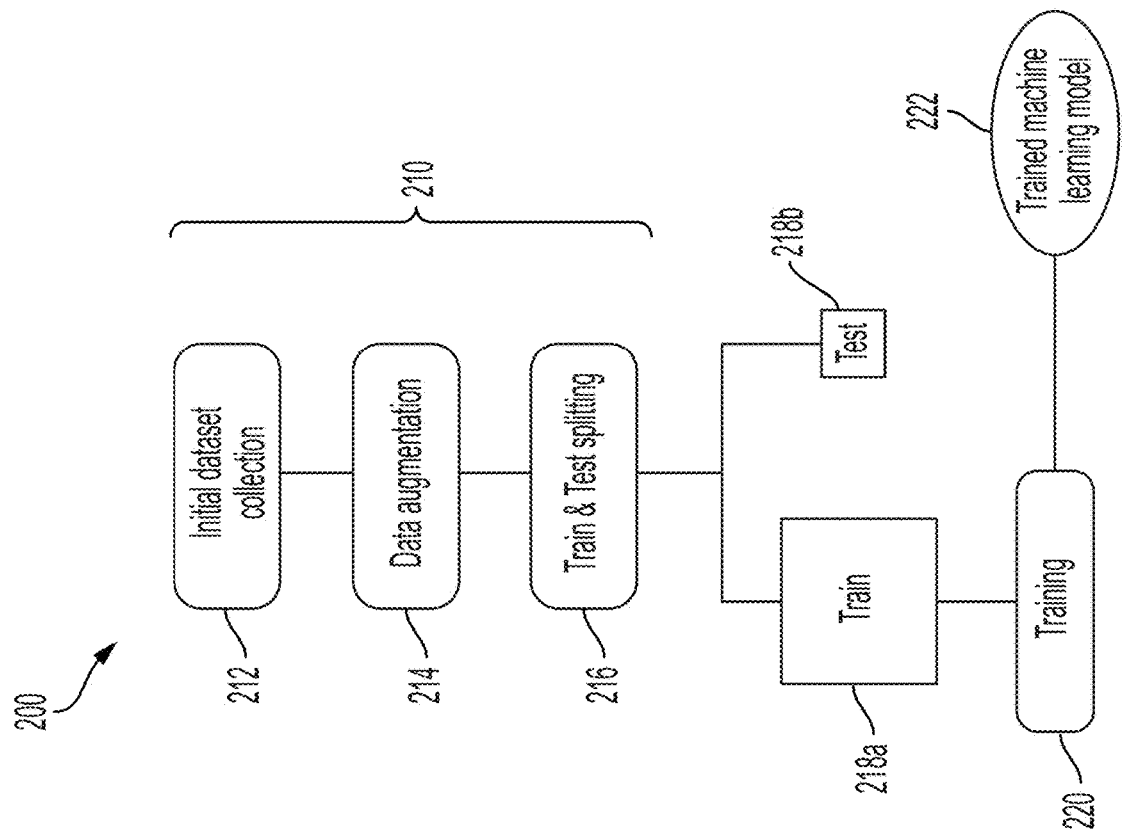
FIG. 2 is a block flow diagram of an example process for training and testing a machine learning model, according to an illustrative embodiment.

Features and advantages of the present disclosure will become more apparent from the detailed description of certain embodiments that is set forth below, particularly when taken in conjunction with the figures, in which like reference characters identify corresponding elements throughout. In the figures, like reference numbers generally indicate identical, functionally similar, and/or structurally similar elements.

CERTAIN DEFINITIONS

In order for the present disclosure to be more readily understood, certain terms are first defined below. Additional definitions for the following terms and other terms are set forth throughout the specification.

A device, composition, system, or method described herein as "comprising" one or more named elements or steps is open-ended, meaning that the named elements or steps are essential, but other elements or steps may be added within the scope of the composition or method. To avoid prolixity, it is also understood that any device, composition, or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any device, composition, or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

As used herein, "a" or "an" with reference to a claim feature means "one or more," or "at least one."

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Affinity: As is known in the art, "affinity" is a measure of the tightness with which two or more binding partners associate with one another. Those skilled in the art are aware of a variety of assays that can be used to assess affinity, and will furthermore be aware of appropriate controls for such assays. In some embodiments, affinity is assessed in a quantitative assay. In some embodiments, affinity is assessed over a plurality of concentrations (e.g., of one binding partner at a time). In some embodiments, affinity is assessed in the presence of one or more potential competitor entities (e.g., that might be present in a relevant—e.g., physiological—setting). In some embodiments, affinity is assessed relative to a reference (e.g., that has a known affinity above a particular threshold [a "positive control" reference] or that has a known affinity below a particular threshold [a "negative control" reference" ]. In some embodiments, affinity may be assessed relative to a contemporaneous reference; in some embodiments, affinity may be assessed relative to a historical reference. Typically, when affinity is assessed relative to a reference, it is assessed under comparable conditions.

Amino acid: in its broadest sense, as used herein, refers to any compound and/or substance that can be incorporated into a polypeptide chain, e.g., through formation of one or more peptide bonds. In some embodiments, an amino acid has the general structure $H_2N$—$C(H)(R)$—$COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Antibody, Antibody polypeptide: As used herein, the terms "antibody polypeptide" or "antibody", or "antigen-binding fragment thereof", which may be used interchangeably, refer to polypeptide(s) capable of binding to an epitope. In some embodiments, an antibody polypeptide is a full-length antibody, and in some embodiments, is less than full length but includes at least one binding site (comprising at least one, and preferably at least two sequences with structure of antibody "variable regions"). In some embodiments, the term "antibody polypeptide" encompasses any protein having a binding domain which is homologous or largely homologous to an immunoglobulin-binding domain. In particular embodiments, "antibody polypeptides" encompasses polypeptides having a binding domain that shows at least 99% identity with an immunoglobulin binding domain. In some embodiments, "antibody polypeptide" is any protein having a binding domain that shows at least 70%, 80%, 85%, 90%, or 95% identity with an immuglobulin binding domain, for example a reference immunoglobulin binding domain. An included "antibody polypeptide" may have an amino acid sequence identical to that of an antibody that is found in a natural source. Antibody polypeptides in accordance with the present invention may be prepared by any available means including, for example, isolation from a natural source or antibody library, recombinant production in or with a host system, chemical synthesis, etc., or combinations thereof. An antibody polypeptide may be monoclonal or polyclonal. An antibody polypeptide may be a member of any immunoglobulin class, including any of the human classes: IgG, IgM, IgA, IgD, and IgE. In certain embodiments, an antibody may be a member of the IgG immunoglobulin class. As used herein, the terms "antibody polypeptide" or "characteristic portion of an antibody" are used interchangeably and refer to any derivative of an antibody that possesses the ability to bind to an epitope of interest. In certain embodiments, the "antibody polypeptide" is an antibody fragment that retains at least a significant portion of the full-length antibody's specific binding ability. Examples of antibody fragments include, but are not limited to, Fab, Fab', F(ab')2, scFv, Fv, dsFv diabody, and Fd fragments. Alternatively or additionally, an antibody fragment may comprise multiple chains that are linked together, for example, by disulfide linkages. In some embodiments, an antibody polypeptide may be a human antibody. In some embodiments, the antibody polypeptides may be a humanized. Humanized antibody polypeptides include may be chimeric immunoglobulins, immunoglobulin chains or antibody polypeptides (such as Fv, Fab, Fab', F(ab')2 or other antigen-binding subsequences of antibodies) that contain minimal sequence derived from non-human immunoglobulin. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Backbone, peptide backbone: As used herein, the term "backbone," for example, as in a backbone or a peptide or polypeptide, refers to the portion of the peptide or polypeptide chain that comprises the links between amino acid of the chain but excludes side chains. In other words, a backbone refers to the part of a peptide or polypeptide that would remain if side chains were removed. In certain embodiments, the backbone is a chain comprising a carboxyl group of one amino acid bound via a peptide bond to an amino group of a next amino acid, and so on. Backbone may also be referred to as "peptide backbone". It should be understood that, where the term "peptide backbone" is used, it is used for clarity, and is not intended to limit a length of a particular backbone. That is, the term "peptide backbone" may be used to describe a peptide backbone of a peptide and/or a protein.

Biologic: As used herein, the term "biologic" refers to a composition that is or may be produced by recombinant DNA technologies, peptide synthesis, or purified from natural sources and that has a desired biological activity. A biologic can be, for example, a protein, peptide, glycoprotein, polysaccharide, a mixture of proteins or peptides, a mixture of glycoproteins, a mixture of polysaccharides, a mixture of one or more of a protein, peptide, glycoprotein or polysaccharide, or a derivatized form of any of the foregoing entities. Molecular weight of biologics can vary widely, from about 1000 Da for small peptides such as peptide hormones to one thousand kDa or more for complex polysaccharides, mucins, and other heavily glycosylated proteins. In certain embodiments, a biologic is a drug used for treatment of diseases and/or medical conditions. Examples of biologic drugs include, without limitation, native or engineered antibodies or antigen binding fragments thereof, and antibody-drug conjugates, which comprise an antibody or antigen binding fragments thereof conjugated directly or indirectly (e.g., via a linker) to a drug of interest, such as a cytotoxic drug or toxin. In certain embodiments, a biologic is a diagnostic, used to diagnose diseases and/or medical conditions. For example, allergen patch tests utilize biologics (e.g., biologics manufactured from natural substances) that are known to cause contact dermatitis. Diagnostic biologics may also include medical imaging agents, such as proteins that are labelled with agents that provide a detectable signal that facilitates imaging such as fluorescent markers, dyes, radionuclides, and the like.

In vitro: The term "in vitro" as used herein refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Native, wild-type (WT): As used herein, the terms "native" and "wild-type" are used interchangeably to refer to biological structures and/or computer representations thereof that have been identified and demonstrated to exist in the physical, real world (e.g., as opposed to in computer abstractions). The terms, native and wild-type may refer to structures including naturally occurring biological structures, but do not necessarily require that a particular structure be naturally occurring. For example, the terms native and wild-type may also refer to structures including engineered structures that are man-made, and do not occur in nature, but have nonetheless been created and (e.g., experimentally) demonstrated to exist. In certain embodiments, the terms native and wild-type refer to structures that have been characterized experimentally, and for which an experimental determination of molecular structure (e.g., via x-ray crystallography) has been made.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the patient is receiving or has received certain therapy to diagnose and/or to treat a disease, disorder, or condition.

Peptide: The term "peptide" as used herein refers to a polypeptide that is typically relatively short, for example having a length of less than about 100 amino acids, less than about 50 amino acids, less than about 40 amino acids less than about 30 amino acids, less than about 25 amino acids, less than about 20 amino acids, less than about 15 amino acids, or less than 10 amino acids.

Polypeptide: As used herein refers to a polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Target: As used herein, the terms "target," and "receptor" are used interchangeably and refer to one or more molecules or portions thereof to which a binding agent—e.g., a custom biologic, such as a protein or peptide, to be designed—binds. In certain embodiments, the target is or comprises a protein and/or peptide. In certain embodiments, the target is a molecule, such as an individual protein or peptide (e.g., a protein or peptide monomer), or portion thereof. In certain embodiments, the target is a complex, such as a complex of two or more proteins or peptides, for example, a macromolecular complex formed by two or more protein or peptide monomers. For example, a target may be a protein or peptide dimer, trimer, tetramer, etc. or other oligomeric complex. In certain embodiments, the target is a drug target, e.g., a molecule in the body, usually a protein, that is intrinsically associated with a particular disease process and that could be addressed by a drug to produce a desired therapeutic effect.

In certain embodiments, a custom biologic is engineered to bind to a particular target. While the structure of the target remains fixed, structural features of the custom biologic may be varied to allow it to bind (e.g., at high specificity) to the target.

Treat: As used herein, the term "treat" (also "treatment" or "treating") refers to any administration of a therapeutic agent (also "therapy") that partially or completely alleviates, ameliorates, eliminates, reverses, relieves, inhibits, delays onset of, reduces severity of, and/or reduces incidence of one or more symptoms, features, and/or causes of a particular disease, disorder, and/or condition. In some embodiments, such treatment may be of a patient who does not exhibit signs of the relevant disease, disorder and/or condition and/or of a patient who exhibits only early signs of the disease, disorder, and/or condition. Alternatively, or additionally, such treatment may be of a patient who exhibits one or more established signs of the relevant disease, disorder and/or condition. In some embodiments, treatment may be of a patient who has been diagnosed as suffering from the relevant disease, disorder, and/or condition. In some embodiments, treatment may be of a patient known to have one or more susceptibility factors that are statistically correlated with increased risk of development of a given disease, disorder, and/or condition. In some embodiments the patient may be a human.

Machine learning module, machine learning model: As used herein, the terms "machine learning module" and "machine learning model" are used interchangeably and refer to a computer implemented process (e.g., a software function) that implements one or more particular machine learning algorithms, such as an artificial neural networks (ANN), convolutional neural networks (CNNs), random forest, decision trees, support vector machines, and the like, in order to determine, for a given input, one or more output values. In some embodiments, machine learning modules implementing machine learning techniques are trained, for example using curated and/or manually annotated datasets. Such training may be used to determine various parameters of machine learning algorithms implemented by a machine learning module, such as weights associated with layers in neural networks. In some embodiments, once a machine learning module is trained, e.g., to accomplish a specific task such as determining scoring metrics as described herein, values of determined parameters are fixed and the (e.g., unchanging, static) machine learning module is used to process new data (e.g., different from the training data) and accomplish its trained task without further updates to its parameters (e.g., the machine learning module does not receive feedback and/or updates). In some embodiments, machine learning modules may receive feedback, e.g., based on user review of accuracy, and such feedback may be used as additional training data, for example to dynamically update the machine learning module. In some embodiments, a trained machine learning module is a classification algorithm with adjustable and/or fixed (e.g., locked) parameters, e.g., a random forest classifier. In some embodiments, two or more machine learning modules may be combined and implemented as a single module and/or a single software application. In some embodiments, two or more machine learning modules may also be implemented separately, e.g., as separate software applications. A machine learning module may be software and/or hardware. For example, a machine learning module may be implemented entirely as software, or certain functions of a ANN module may be carried out via specialized hardware (e.g., via an application specific integrated circuit (ASIC), field programmable gate arrays (FPGAs), and the like).

Substantially: As used herein, the term "substantially" refers to the qualitative condition of exhibiting total or near-total extent or degree of a characteristic or property of interest.

Scaffold Model: As used herein, the term "scaffold model" refers to a computer representation of at least a portion of a peptide backbone of a particular protein and/or peptide. In certain embodiments, a scaffold model represents a peptide backbone of a protein and/or peptide and omits detailed information about amino acid side chains. Such scaffold models, may, nevertheless, include various mechanisms for representing sites (e.g., locations along a peptide backbone) that may be occupied by prospective amino acid side chains. In certain embodiments, a particular scaffold models may represent such sites in a manner that allows determining regions in space that may be occupied by prospective amino acid side chains and/or approximate proximity to representations of other amino acids, sites, portions of the peptide backbone, and other molecules that may interact with (e.g., bind, so as to form a complex with) a biologic having the peptide backbone represented by the particular scaffold model. For example, in certain embodiments, a scaffold model may include a representation of a first side chain atom, such as a representation of a beta-carbon, which can be used to identify sites and/approximate locations of amino acid side chains. For example, a scaffold model can be populated with amino acid side chains (e.g., to create a ligand model that represents at least a portion of protein and/or peptide) by creating full representations of various amino acids about beta-carbon atoms of the scaffold model (e.g., the beta-carbon atoms acting as 'anchors' or 'placeholders' for amino acid side chains). In certain embodiments, locations of sites and/or approximate regions (e.g., volumes) that may be occupied by amino acid side chains may be identified and/or determined via other manners of representation for example based on locations of an alpha-carbons, hydrogen atoms, etc. In certain embodiments, scaffold models may be created from structural representations of existing proteins and/or peptides, for example by stripping amino acid side chains. In certain embodiments, scaffold models created in this manner may retain a first atom of stripped side chains, such as a beta-carbon atom, which is common to all side chains apart from Glycine. As described herein, retained beta-carbon atoms may be used, e.g., as a placeholder for identification of sites that can be occupied by amino acid side chains. In certain embodiments, where an initially existing side chain was Glycine, the first atom of glycine, which is hydrogen, can be used in place of a beta-carbon and/or, in certain embodiments, a beta carbon (e.g., though not naturally occurring in the full protein used to create a scaffold model) may be added to the representation (e.g., artificially). In certain embodiments, for example where hydrogen atoms are not included in a scaffold model, a site initially occupied by a Glycine may be identified based on an alpha-carbon. In certain embodiments, scaffold models may be computer generated (e.g., and not based on an existing protein and/or peptide). In certain embodiments, computer generate scaffold models may also include first side chain atoms, e.g., beta carbons, e.g., as placeholders of potential side chains to be added.

DESCRIPTION

Reference will now be made in detail to the present disclosed embodiments, one or more examples of which are illustrated in the accompanying drawing. The detailed description uses numerical and/or letter designations to refer to features in the drawing. Like or similar designations in the drawing and description have been used to refer to like or similar parts of the present embodiments.

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are provided for the convenience of the reader—the presence and/or placement of a header is not intended to limit the scope of the subject matter described herein.

Computer-aided design of candidate molecules for use as new drugs can facilitate the drug discovery process, increasing the speed at which new drugs are identified, tested, and brought to market and reducing costs associated with, e.g., experimental trial-and-error. Such in-silico molecule design approaches are, however, challenging and limited in their accuracy, especially when applied to design of large molecules, such as proteins and/or peptides. These molecules are typically on the order of several kilo-Daltons (kDa) in terms of molecular weight, and have complex and hierarchical three-dimensional structures that influence their behavior, making functionality difficult to predict computationally. Accordingly, success rates of existing computational approaches to design of large molecules, such as proteins and peptides, is limited, and extensive experimental verification is often required.

In certain embodiments, technologies described herein provide, among other things, systems, methods, and architectures that address challenges associated with generating accurate predictions of structural features, properties, and functions of large molecules, thereby providing an improved toolkit for in-silico design of biologics, for example proteins and peptides. In particular, in certain embodiments, systems and methods described herein include artificial intelligence (AI)—based software modules that can accurately predict performance of candidate biomolecules and/or portions thereof (e.g., amino acid backbones, sub-regions of interest, etc.) with respect to particular design criteria. In certain embodiments, design criteria and performance metrics that are evaluated by AI-powered modules described herein are tailored based on structural biology considerations relevant to large molecule design, for example, reflecting hierarchical organization of protein and peptide structures. In this manner, technologies described herein provide an improved toolkit for in-silico biomolecule design, thereby increase a likelihood of generating viable options for use in real world applications such as in disease treatment, prevention, and diagnosis. Accordingly, approaches described herein can reduce experimentation costs and cycle time associated with verifying biomolecule properties.

A. In-Silico Design and Engineering of Custom Biomolecules

In certain embodiments, designing a particular biologic structure (e.g., protein and/or peptide) with various desired structural features and, e.g., ultimately, properties in-silico involves using computer-generated predictions to examine how changes to structural features of the biologic impact desired functionality and properties and, for example, making adjustments according to achieve desired performance.

A variety of structural features may be varied and examined. These include, for example, without limitation, amino acid sequences in various regions of the biologic, rotamer variations for one or more amino acids, post-translational modifications (PTMs) and conformations of a protein and/or peptide molecule's peptide backbone. Structural features may also include properties that relate to a way the biologic interacts with other molecules. For example, as described in further detail herein, approaches that aim to design biologics for binding to particular targets (e.g., molecules and/or complexes formed thereof), a three-dimensional orientation of the biologic with respect to a particular target (referred to herein as a "pose") molecule may be varied so as to allow different poses of the biologic in relation to the target to be evaluated. Accordingly, especially for large, biologic structures, a wide range of structural features, both of the biologic itself as well as in relation to how it orients and forms a complex with respect to another, e.g., target, molecule exist and can be adjusted to influence performance. The landscape of variations in and/or combinations of these structural features creates an extensive search space to be explored in order to identify and design features of a prospective custom biologic structure that will result in desired properties and functionality. Doing so in an efficient manner presents a significant challenge.

Moreover, in certain embodiments, navigating this search space to identify those favorable structural features that create performance improvements in silico relies on use of computational tools to generate predictions, for example, of how changing one or more particular structural features influences a desired property, such as binding affinity to a particular target, thermal stability, aggregation, etc. For example, in designing a biomolecule for binding to a particular target, a computer generated prediction of binding affinity may be used as a performance metric to compare different biomolecule structure designs.

Accordingly, the ability to (i) efficiently explore a vast search space of structural features of large molecules and (ii) generate accurate predictions of how changes in structural features of a biologic design impact properties and performance with respect to desired design criteria are key capabilities that allow for successful in silico design of biologic molecules.

In particular, managing the size of the potential search space is non-trivial. First, in certain embodiments, intelligent sampling techniques are typically used in order to optimize an objective function that measures performance with respect to a desired design criteria. Brute force, e.g., random, sampling approaches may not viable in certain embodiments. For example, brute force approaches exhaustively explore a search space. When a search space is large, its exploration via a brute force approach can become intractable. Accordingly, in certain embodiments, approaches such as simulated annealing may be used in connection with tools described herein. Second, additionally or alternatively, in certain embodiments, approaches described herein may leverage insight based on structural biology considerations to reduce sizes and/or dimensionality of potential search spaces. For example, as described herein, in certain embodiments, tools described herein utilize and/or provide for a step-wise, modular approach whereby, particular structural features—such as backbone orientation and amino acid sequences—are optimized separately, one after the other. In certain embodiments, this modular approach reflects a hierarchical organization of protein and/or peptide structures.

Additionally or alternatively, accurately predicting performance of structures in a manner that allows different structural designs scored in a quantifiable (or objective) fashion and, accordingly, compared, is also challenging. In certain embodiments, tools described herein address limitations of physics-based, empirical, and knowledge-based (for example, machine learning optimized around one or more handpicked features) approaches by leveraging a deep learning approach that utilizes AI-computed scoring functions.

In particular, in certain embodiments, for example, tools described herein leverage insight that computed scores need not necessarily correspond to experimentally measurable performance metrics. For example, in certain embodiments, levels of similarity between key features prospective custom biologic structures and those of pre-existing, successful biological structures and assemblies can be useful and accurate predictors of success. Moreover, in certain embodiments, machine learning models can be used to accurately identify these key features, and determine levels of similarity in a quantitative fashion. Accordingly, in certain embodiments, approaches such as AI-based classification and/or regression can be used to create scoring functions that accurately measure a likelihood that particular designs will be successful.

Accordingly, approaches described herein may utilize computational tools such as artificial intelligence (AI), neural networks, artificial neural networks (ANN), convolutional neural networks (CNN), generative adversarial networks (GAN), deep learning models, and others to explore the search space and generate predictions for large molecule and other biomolecule function, structure, and/or properties. As machine learning techniques typically rely on training procedures in order to establish model parameters (e.g., weights) and allow models to make accurate predictions, embodiments described herein, may utilize a variety of data sources for training, such as, without limitation, public databases such as the protein databank (PDB), publicly available binding affinity databases, data from other biological databases, proprietary databases, as well examples generated from other sources of data including laboratory data, academic research, and open literature. As described in further detail herein, approaches described herein may also include data augmentation approaches and use of computer generated training examples to supplement data on pre-existing structures and to tailor training data sets to a particular types of structural features (e.g., backbone conformation, amino acid sequence, etc.) and/or performance being evaluated by a particular model.

B. Example Pipeline for Designing Custom Binders

Figure 1:
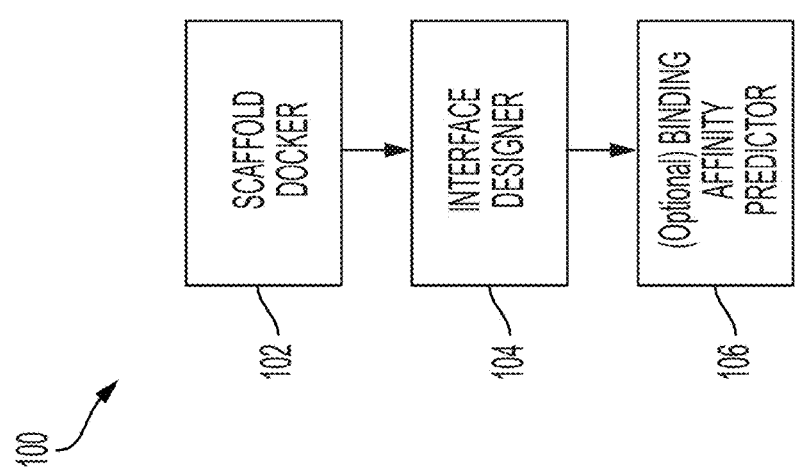
FIG. 1 is a block flow diagram of an example process for designing custom biologic structures for binding to a target, according to an illustrative embodiment.

FIG. 1 illustrates an example process 100 for designing a custom biologic structure for binding to a target. Example process 100 shown in FIG. 1 utilizes a scaffold docker module 102, an interface designer module 104, and, optionally, a binding affinity predictor module 106. In example process 100, scaffold docker module 102, interface designer module 104, and binding affinity predictor module 106 are arranged sequentially, in a pipeline, with results obtained from scaffold docker module 102 used as input for interface designer module 104. Other arrangements of these and/or other modules are also possible and are contemplated by the present disclosure.

As explained in further detail herein, each of the three modules (scaffold docker module 102, interface designer module 104, and binding affinity predictor module 106) utilizes a particular machine learning model to evaluate and score certain structural features of a prospective custom biologic with respect to particular performance metrics.

In particular, in certain embodiments, scaffold docker 102 may be used to first identify particular designs of peptide backbones and ways in which they can be oriented, with respect to the target, that are favorable for binding. Once identified, such favorable backbones can be populated with amino acids to create a custom biologic structures (e.g., in silico, via use of various computer representations and approaches described herein) via downstream modules, e.g., reflecting the hierarchical manner of protein structures.

In particular, in certain embodiments, scaffold docker module 102 evaluates candidate scaffolds models and particular three-dimensional orientations—referred to herein as poses—thereof for predicted suitability (e.g., a likelihood of success) in binding to a particular target. Candidate scaffold models are representations of candidate peptide backbones, which can be populated with amino acids to create a custom biologic structures. Scaffold docker module 102 generates a plurality of prospective scaffold-target complex models, each representing a particular candidate peptide backbone positioned at a particular pose with respect to the target. Scaffold docker module 102 utilizes a machine learning algorithm to compute scaffold-pose scores for the prospective scaffold-target complex models. As explained in further detail herein, a scaffold-pose score for a prospective scaffold-target complex model is a value that provides a measure of suitability of the particular candidate peptide backbone and pose represented by the prospective scaffold target-complex model. Accordingly, scaffold docker module 102 uses computed scaffold-pose scores to select a subset of prospective scaffold-target complex models, each representing a particular candidate peptide backbone at a particular pose determined (e.g., based on the scaffold-pose scores) to be suitable for binding to the target.

In certain embodiments, prospective scaffold-target complex models determined via scaffold docker module 102 can be used as a starting point for interface designer module 104, which populates candidate peptide backbones with amino acids to generate candidate interfaces comprising various combinations of amino acid types and rotamers at sites located in proximity to the target (e.g., the target molecule and/or e.g., in the case of a complex, one or more constituent molecules thereof)(e.g., hotspot locations and/or context locations). In this manner, interface designer module 104 generates a plurality of prospective ligand-target complex models, each representing a particular candidate peptide backbone positioned at a particular pose with respect to the target (e.g., as determined by scaffold docker module 102) and having a particular amino acid interface. Interface designer module 104 generates and evaluates prospective ligand-target complex models to determine interface designs likely to be successful for binding to the target. In particular, interface designer module 104 utilizes a machine learning algorithm to compute an interface score for each prospective ligand-target complex model. Interface scores are described in further detail herein, and provide a measure of suitability of a particular interface design for binding to the target. Interface designer module 104 selects a subset of the prospective ligand-target complex models based on the computed interface scores, thereby identifying ligand structures predicted to be successful for binding to the target. These identified ligand structures, or portions thereof (e.g., sub-regions in proximity to the target) can be used to create custom biologics.

In certain embodiments, a binding affinity predictor module 106 may also be used to predict binding affinities between designer biologic structures and the target. In certain embodiments, binding affinity predictor module 106 may be used to evaluate and/or refine prospective ligand-target complex models determined via interface designer module 104. For example, in certain embodiments, binding affinity module 106 may receive a set of candidate ligand-target complex models from interface designer module 104 and generate binding affinity predictions based on the set of candidate ligand-target complex models. As described in further detail herein, these predicted binding affinities can be used, for example, to sort and/or identify a subset of candidate designs, as well as to refine and/or modulate structural designs further.

C. Dataset Creation and Data Representation Techniques i. Dataset Creation

In certain embodiments, scaffold-docker module 102, interface designer module 104, and binding affinity predictor module 106 each utilize a machine learning model as a scoring function that predicts performance of various structural modifications and designs en route to creating a custom biologic structure.

Turning to FIG. 2, in certain embodiments, each machine learning model is trained, for example, using structural data (e.g., representing experimentally determined crystallographic structures) for existing biological complexes obtained from public databases or elsewhere. As described in further detail herein, depending on a particular type of structural feature and/or scoring function to be evaluated, examples of existing biological complexes may be supplemented with computer generated representations of artificial biological complexes that have not been demonstrated to exist physically.

FIG. 2 shows an example training and validation workflow 200 used in certain embodiments. Method 200 may be used to develop a machine learning model that can be used as a scoring function, for example to predict performance of particular design elements of a custom biologic being created, for use in various modules described herein (e.g., scaffold docker module, interface designer module, binding affinity predictor module, etc.). In certain embodiments, training various machine learning models described herein may generally include one or more data preparation steps 210, including, for example, collection of an initial dataset 212 (e.g., from various databases) and data augmentation steps 214. These data preparation steps 210 may be used to create a robust and/or non-biased) training dataset that includes, for example, a sufficient number and/or variety of examples to allow a machine learning model to be trained to make accurate assessments of structural designs and their predicted performance. As illustrated in FIG. 2, in certain embodiments, a portion of examples may be set aside or split off 216 to create a testing dataset 218*b*, distinct from training dataset 218*a*. Training dataset 218*b* may be used for training (e.g., to establish weights) 220 and create a trained machine learning model 222. Testing dataset 218b can be used to validate a trained machine learning model 222, for example to identify and/or avoid overfitting.

Figure 3:
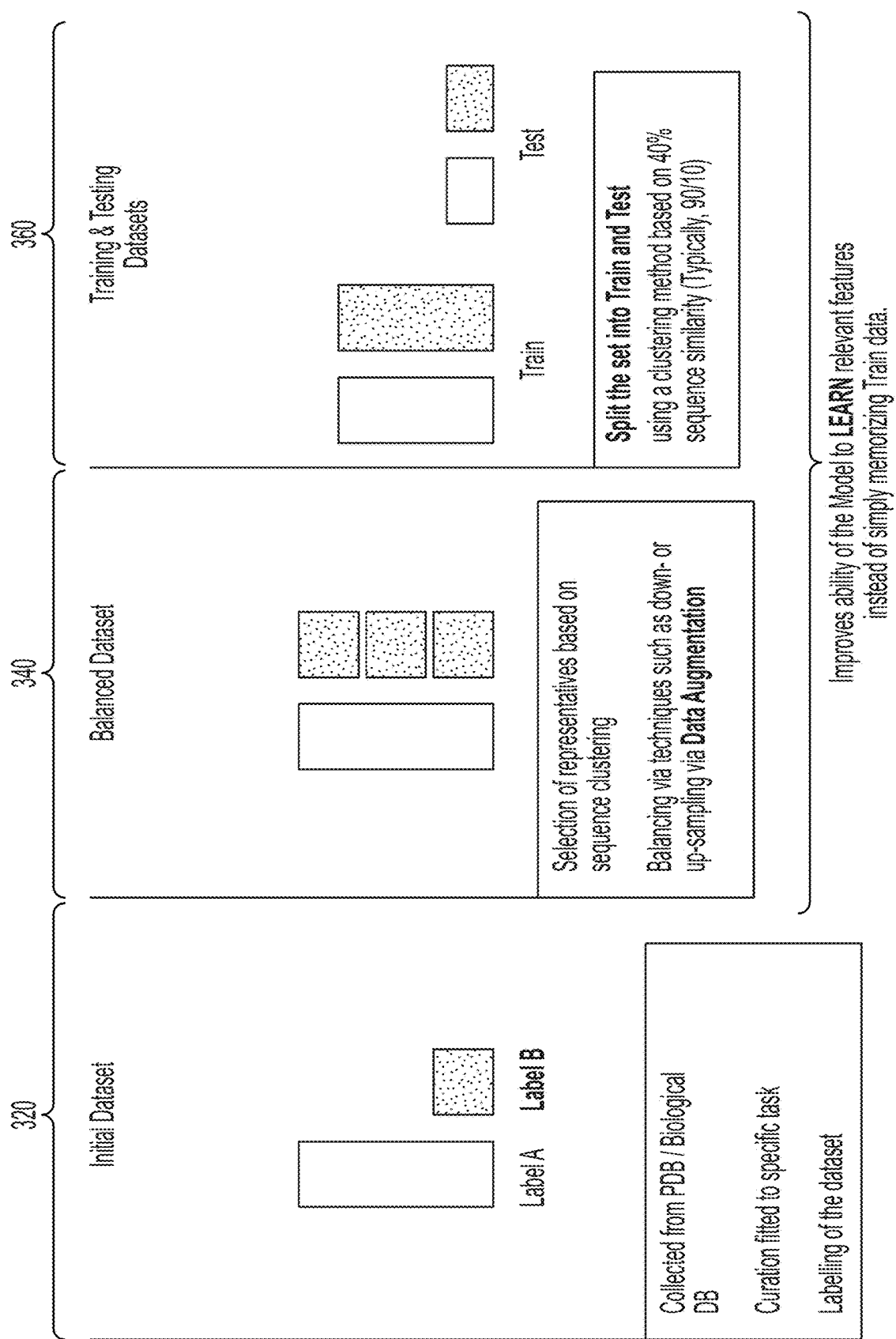
FIG. 3 is a schematic illustration of various example data preparation steps used in various embodiments described herein.

FIG. 3 illustrates various data preparation steps in further detail. For example, a step of collecting an initial dataset 320, may include collecting data, for example, from one or more public databases such as the protein databank (PDB) and/or other biological databases) as well as curating an initial dataset based on a specific task or goal. In certain embodiments, data curation may include filtering the data based on various criteria, such as a minimum resolution (e.g., such that structures for which a resolution is above a particular threshold value are not included). For example, various datasets in example implementations of embodiments described herein were created using resolutions better than 2.7 Å. Individual data elements may be pre-labeled and/or assigned labels, for example to identify each data element as belonging to a particular class. In certain embodiments, various steps may be performed to produce a balanced dataset 340 from an initial dataset. For example, sequence clustering may be performed to identify clusters of similar examples, and a subset (e.g., smaller, limited number) of representative examples from each cluster be selected for inclusion in a balanced data set. Additionally or alternatively, in certain embodiments, balancing techniques including up-sampling and down-sampling, may be used.

In certain embodiments, balancing may include a data augmentation step 214. For example, in certain embodiments, neural networks require a large amount of training data. In certain cases, datasets that are available (e.g., initial datasets) are small, e.g., and may not be of sufficient size for training. Accordingly, in certain embodiments, data augmentation techniques can be used to artificially generate more data from an existing (e.g., initial) dataset. Additionally or alternatively, in certain embodiments, available datasets may be imbalanced. For example, in certain embodiments, binding affinity datasets may contain many examples of complexes with mid-range affinities whereas high and low affinity complexes may be under-represented. In certain embodiments, data augmentation may also be used to balance a dataset. Classes can be differentially augmented to try to limit class imbalance. Additionally or alternatively, in certain embodiments, data augmentation utilized herein may apply rotations to structural data used. For example, in certain embodiments, various machine learning models utilized herein comprise convolutional neural networks (CNNs). CNN's may 'perceive' rotated versions of otherwise identical structures differently. Accordingly, generating multiple training examples from one structure by rotating it in different ways can be used to avoid inadvertently training a CNN to learn to differentiate otherwise identical structures on the basis of rotational variations. In certain embodiments, to generate rotational examples for data augmentation, sampling is performed via a Hopf Fibration, e.g., using a HEALPix grid, since sampling along a conventional three-axis grid may produce non-uniform sampling of rotational vectors. Hopf Fibration is described in Gorski et al. arXiv: astro-ph/0409513. 2005 and Yershova et al. Int J Rob Res. 2010 Jun. 1; 29(7): 801-812.

In certain embodiments, a dataset (e.g., a balanced dataset 340) may be divided 216 into training sets 218a and testing sets 218b (e.g., collectively, 360) for training and validating a machine learning model. For example, where individual data elements represent biologic structures, a dataset may be split into training and testing datasets based on sequence similarities. For example, in certain embodiments a data set may be split such that there is from about 20% to about 80% sequence similarity between the training and testing sets. In some embodiments, the sequencing similarity may be from about 10% to about 90%, or from about 25% to about 70%, or from about 30% to about 60%, or from about 35% to about 50%, or from about 35% to about 45%.

Figure 4:
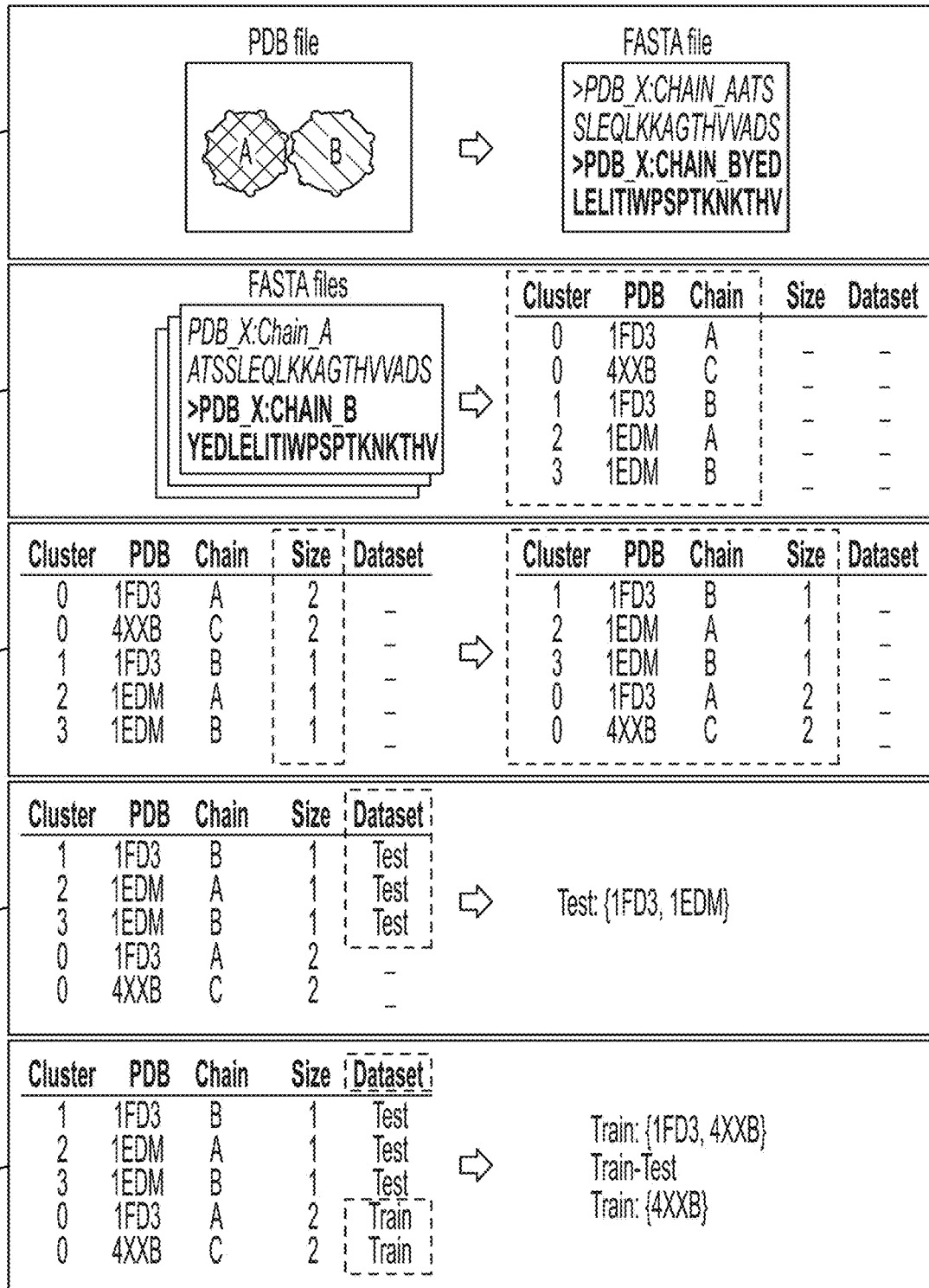
FIG. 4 is a diagram of an example procedure for splitting a dataset comprising biological data into training and testing datasets, according to an illustrative embodiment.

An example process 500 for splitting a dataset comprising examples of protein and/or peptide complexes (e.g., interfaces) based on sequence clustering is shown in FIG. 4. An approach such as example process 500, and/or variations thereof may be used in various embodiments of training procedures described herein. Other approaches for splitting a dataset may also be utilized in accordance with embodiments described herein.

ii. Data Representations

In certain embodiments, various modules (e.g., a scaffold docker module 102, an interface designer module 104, a binding affinity predictor module 106) and/or machine learning models (e.g., utilized by various modules) described herein operate on and analyze representations of biologic structures and compute values of scoring functions based thereon. In certain embodiments, representations include structural models of a biologic, or portion thereof (e.g., a scaffold model, representing a peptide backbone of a protein and/or peptide). In certain embodiments, representations may also include models of a biologic or portion thereof together with one or more other molecules, such as a target, in a complex.

For example, in certain embodiments various technologies and tools described herein utilize, manipulate, evaluate, etc., structural models of proteins and/or peptides. In certain embodiments, such structural models include models of proteins and/or peptides in complex with other molecules. In certain embodiments, these include models of a ligand and a receptor, and are referred to as a ligand-receptor complex model, which comprises a ligand model—a computer representation of at least a portion of the ligand—and a receptor model—a computer representation of at least a portion of the receptor.

In certain embodiments, various modules and approaches described herein may utilize a scaffold model representation that represents a peptide backbone of a particular protein and/or peptide. In certain embodiments, scaffold models may be created from structural representations of existing proteins and/or peptides, for example by stripping amino acid side chains. In certain embodiments, while scaffold models omit detailed amino acid side chain structure, they may nevertheless retain a first atom of a side chain, such as a beta-carbon atom, which is common to all side chains apart from Glycine, and may be used, e.g., as a placeholder for identification of sites that can be occupied by amino acid side chains. In certain embodiments, where an initially existing side chain was Glycine, the first atom of glycine, which is hydrogen, can be used in place of a beta-carbon. In certain embodiments, scaffold models may be computer generated (e.g., and not based on an existing protein and/or peptide). In certain embodiments, computer generate scaffold models may also include first side chain atoms, e.g., beta carbons, e.g., as placeholders of potential side chains to be added.

Accordingly, in certain embodiments, rather than represent an entire ligand of a particular biological complex, a scaffold model can be used in combination with a model of a receptor, creating a scaffold-receptor complex model.

Various structural models described herein may be implemented in a variety of manners, via a variety of data representations. In certain embodiments, a structural model may be represented as a listing of types and coordinates of various atoms in space, such as, for example, PDB files. In certain embodiments, structural models may include additional information, such as an indication of which atoms belong to which particular amino acid residue or portion of peptide backbone, an indication of secondary structure motifs, etc.

Figure 5:
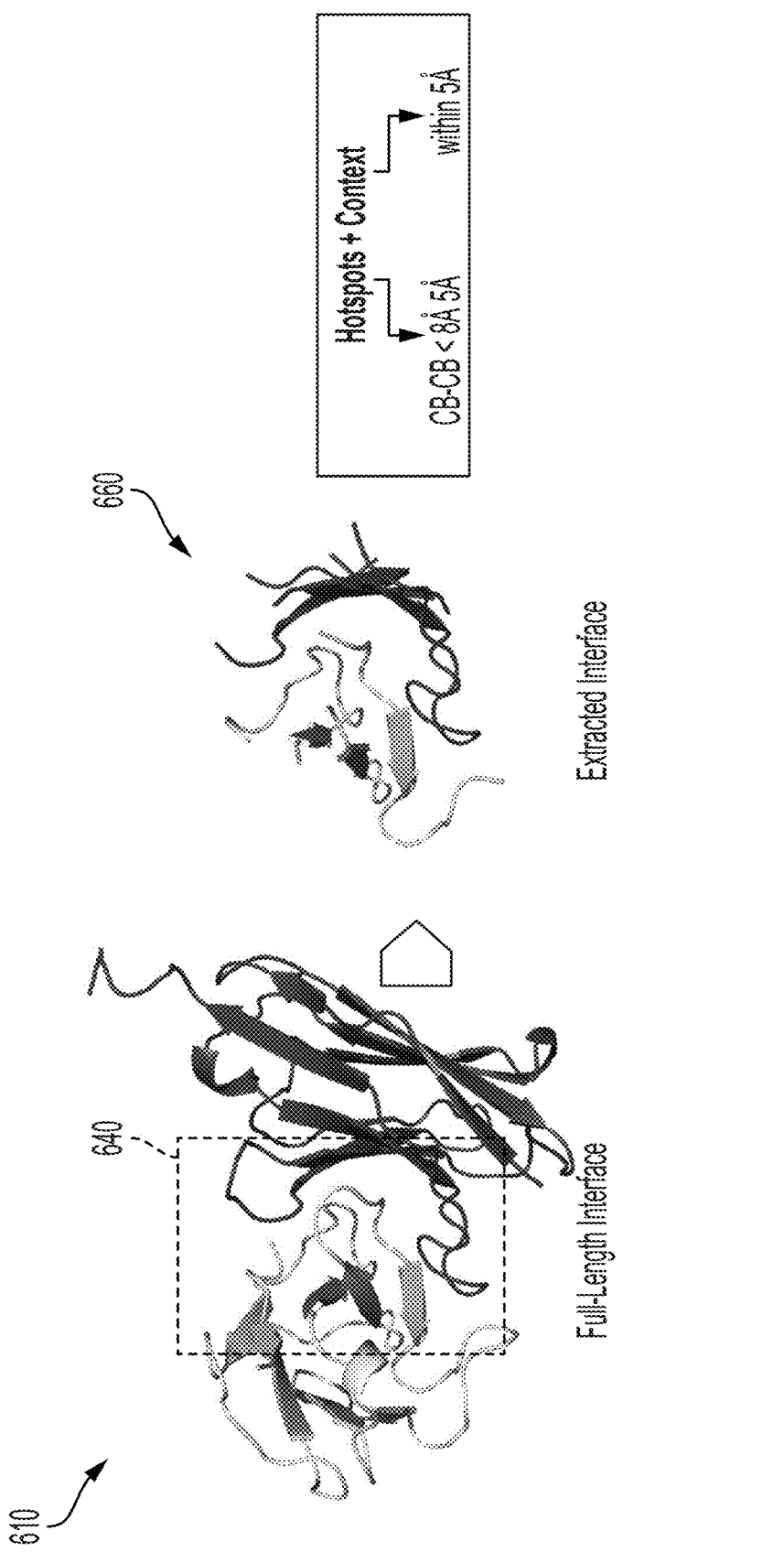
FIG. 5 is a schematic of an example approach for identifying and/or extracting an interface sub-region of a model of a biological complex, according to an illustrative embodiment.

Turning to FIG. 5, in certain embodiments, while an overall complex comprising, for example, a ligand and a receptor molecule may be large, behavior such as binding may be influenced primarily by a smaller sub-region 640 of the complex, about an interface where atoms and/or amino acid side chains of the ligand and receptor are located in proximity to each other. Accordingly, in certain embodiments, approaches described herein include and/or utilize various interface extraction steps, used to identify interface sub-regions comprising portions of a ligand and/or receptor of a complex. Representations (e.g., complex models) 660 of identified interface sub-regions may be utilized, e.g., as opposed to models of a larger portion 610 (e.g., though not necessarily entire) of a complex, for (e.g., to facilitate) further processing, such as identifying particular amino acid sites to limit sequence design to, and/or to provide more manageable input to a machine learning model.

For example, in certain embodiments, interface extraction may be based on and/or include steps of identifying particular amino acid sites of a ligand and/or receptor determined to be relevant to influencing binding. For example, in certain embodiments, sites referred to as "hotspots" may be identified on a ligand and/or receptor. For a ligand, hotspots refer to sites which, when occupied by an amino acid side chain, place at least a portion of the amino acid side chain in proximity to one or more side chains and/or atoms of the receptor. Likewise, for a receptor, hotspots are sites which, when occupied via an amino acid side chain, place at least a portion of the amino acid side chain in proximity to one or more side chains and/or atoms of the ligand.

In certain embodiments, for example since size, geometry, and orientation of various acid side chains may vary, hotspots may be identified based on distances between beta carbon (C$\beta$) atoms of a ligand and receptor of a complex. For example, a ligand hotspot may be identified as a particular site on the ligand that, when occupied by an amino acid side chain, will place a C$\beta$ atom of the side chain located at the site within a threshold distance of a C$\beta$ atom of the receptor. Receptor hotspots may be identified analogously. Since C$\beta$ atoms are common to every amino acid side chain apart from Glycine, this approach provides a uniform criteria for identifying hotspots, independent of a particular amino acid that occupies a particular site. In certain embodiments, in the singular case where a Glycine residue occupies a particular site, Glycine's hydrogen atom may be used in place of a C$\beta$, but hotspots identified in an otherwise identical fashion. Additionally or alternatively, in certain embodiments, distances between alpha-carbons (C$\alpha$) associated with amino-acid sites may be determined, e.g., in a similar manner to which distances between C$\beta$ atoms are determined. In this manner, C$\alpha$ distances may be compared with various threshold values to identify hotspots.

Various threshold distances may be used for identification of hotspots. For example, in certain embodiments, a hotspot threshold distance of 8 Å (i.e., 8 Angstroms) is used. In some embodiments, other thresholds may be used for defining a hotspot (such as less than 3 Å, less than 4 Å, less than 5 Å, less than 6 Å, less than 7 Å, less than 9 Å, less than 10 Å, less than 12 Å, less than 15 Å, less than 20 Å, as well as other suitable thresholds).

In certain embodiments, hotspots may be identified based on comparison of values computed by various functions—e.g., of one or both of a C$\alpha$ and C$\beta$ distance—with one or more threshold values. Such functions may take into account features such as bond angles, surface area, etc.

Additionally, or alternatively, approaches described herein may also identify sites referred to as context sites, which are not hotspots themselves, but are located near (e.g., and on a same peptide or polypeptide chain) hotspots. In certain embodiments, for a particular hotspot, one or more context sites about the hotspot are identified as those sites for which a C$\beta$ atom of a residue located at the site (or H atom, where the residue is Glycine) is within a threshold distance (e.g., a context threshold distance) of a C$\beta$ atom (or H atom) of a residue occupying the particular hotspot. In this manner, for a particular hotspot, one or more associated context sites may be identified.

In certain embodiments, as with hotspot threshold distances, various context threshold distances may be used to identify context sites. For example, as shown in FIG. 5, in certain embodiments, a context threshold distance of 5 Å (i.e., 5 Angstroms) is used. In some embodiments, other thresholds may be used for defining a hotspot (such as less than 3 Å, less than 4 Å, less than 5 Å, less than 6 Å, less than 7 Å, less than 9 Å, less than 10 Å, less than 12 Å, less than 15 Å, less than 20 Å, as well as other suitable thresholds). In certain embodiments, a context threshold distance is less than a hotspot threshold distance.

In certain embodiments, hotspot and context site identification (and, accordingly, interface extraction) may be performed for scaffold models as well as ligand models. For example, as described herein, scaffold models may retain first side chain atoms—beta carbons and/or hydrogens—and, accordingly, hotspot and context site identification as described herein may be performed for ligand and scaffold models alike.

In certain embodiments, interface extraction may be used to identify certain portions of a computer representation of a biological complex comprising at least a portion of ligand and a receptor. For example, in certain embodiments, portions of a biological complex model (e.g., representations of amino acid side chains, voxels of a three dimensional grid or matrix, etc.) corresponding to hotspot and/or context sites may be identified. For example, in certain embodiments, an interface portion of a biological complex model may include representations of amino acid side chains located at hotspot and/or context sites, and exclude other portions of the complex model. In certain embodiments, an interface portion may include representations of portions of a peptide backbone of a ligand and/or receptor that are associated with hotspot and/or context sites. For example, an interface portion may include representations of side chains located at hotspot and/or context sites as well as adjacent atoms of a peptide backbone (e.g., alpha carbon, hydrogen, and peptide bond). In certain embodiments, an interface portion may include portions of a complex model corresponding to locations within a continuous volume comprising identified hotspot and/or context sites, such as a smallest rectangular volume comprising identified hotspot and/or context sites.

Figure 6:
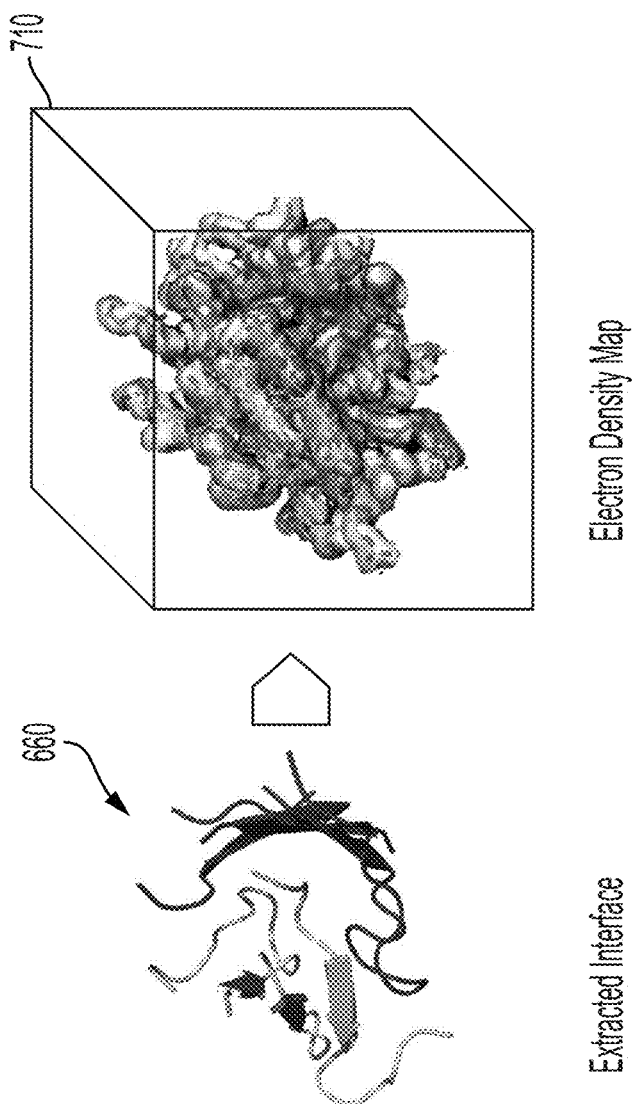
FIG. 6 is a schematic of an example process for creating a volumetric representation of an interface sub-region of a biological complex model, according to an illustrative embodiment.

Turning to FIG. 6, in certain embodiments, biological molecules and/or complexes thereof may be represented via structural models that, among other things, identify types and locations of atoms in physical space, for example via coordinate files such as those used for PDB entries. In certain embodiments, approaches described herein may also utilize volumetric representations, whereby a three-dimensional data representation (e.g., matrix) is used to represent a physical three-dimensional space. In certain embodiments, approaches described herein create, as a volumetric representation of a particular biological molecule and/or complex, a three dimensional electron density map (EDM) 710. In certain embodiments, a 3D EDM may be created from a structural model, for example, by simulating x-ray diffraction and scattering. For example, in certain embodiments, approaches described herein generate 3D EDMs from structural models (e.g., atomic coordinates) based on a five-term Gaussian approximation and atomic scattering factors as found in International Tables for X-ray Cryst. Vol. IV. A similar approach is implemented in CCP4 (see, e.g., ccp4.ac.uk). In certain embodiments, other Gaussian approximations, such as a two-term Gaussian approximation, may be used. In certain embodiments, such EDM representations, as described and utilized herein, may have a size of 64×64×64 Å$^3$ (i.e., cubic Angstroms) with a 1 Å (one Angstrom) grid spacing, though various embodiments and implementations may utilize other input sizes and resolution.

Figure 7:
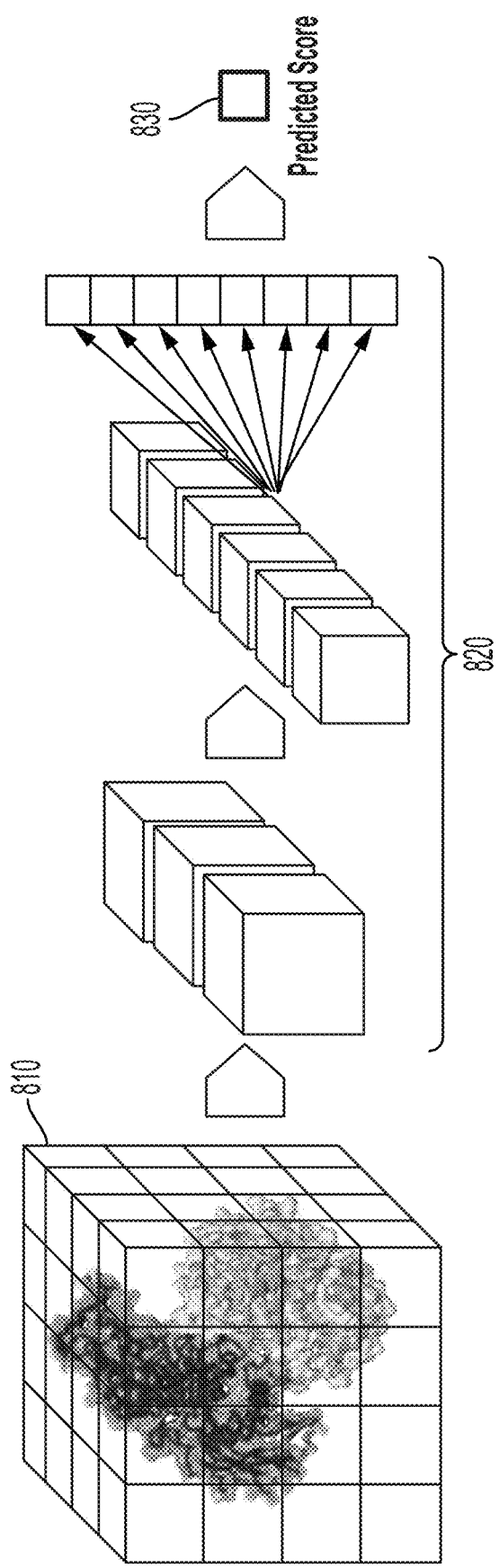
FIG. 7 is a schematic of a machine learning model that determines a scoring function used for evaluating performance of a particular biological complex model, according to an illustrative embodiment.

Turning to FIG. 7, in certain embodiments, volumetric representations, such as EDMs 810, are used as input to machine learning models 820 used to evaluate and score various structural designs for creating custom biologics as described herein. In this manner, in certain embodiments, a machine learning model 820 receives a 3D EDM representing at least a portion of a biological complex (e.g., a sub-region about an interface) and determines, as output a score 830. In certain embodiments, the score quantifies a measure of similarity between the biological complex and native and/or otherwise successful complexes, as determined by the machine learning model. In certain embodiments, the score is a predicted physical property, such as a predicted binding affinity. In certain embodiments, machine learning models as described herein are trained using thousands of curated example representations of biological complexes, allowing them to make accurate inferences and predictions.

Without wishing to be bound to any particular theory, it is believed that use of 3D EDMs as input to machine learning models as described herein may be advantageous in that it allows for use of CNNs and facilitates incorporation of three-dimensional spatial relationships into AI-based learning procedures. Additionally or alternatively, electron density maps provide an accurate way of representing three dimensional structure, as well as physical and chemical properties, of biological complexes, such as receptors-ligand complex and/or, more particularly, complexes formed by prospective custom biologic designs intended for binding to target molecules and/or target complexes as described herein.

In certain embodiments, among other things, use of 3D EDMs as volumetric input to a machine learning model is distinct from other approaches, which convert atomic coordinates to abstract representations of each atom and interpolate their positions into 3D grids.

In certain embodiments, for example as shown in FIG. 6, interface extraction may be used to identify an interface portion of a biological complex model, and the identified interface portion 660 (e.g., rather than the entire biological complex model) used to generate a 3D EDM 710 for use as input to a machine learning model.

D. Scaffold Docker Module

Figure 8:
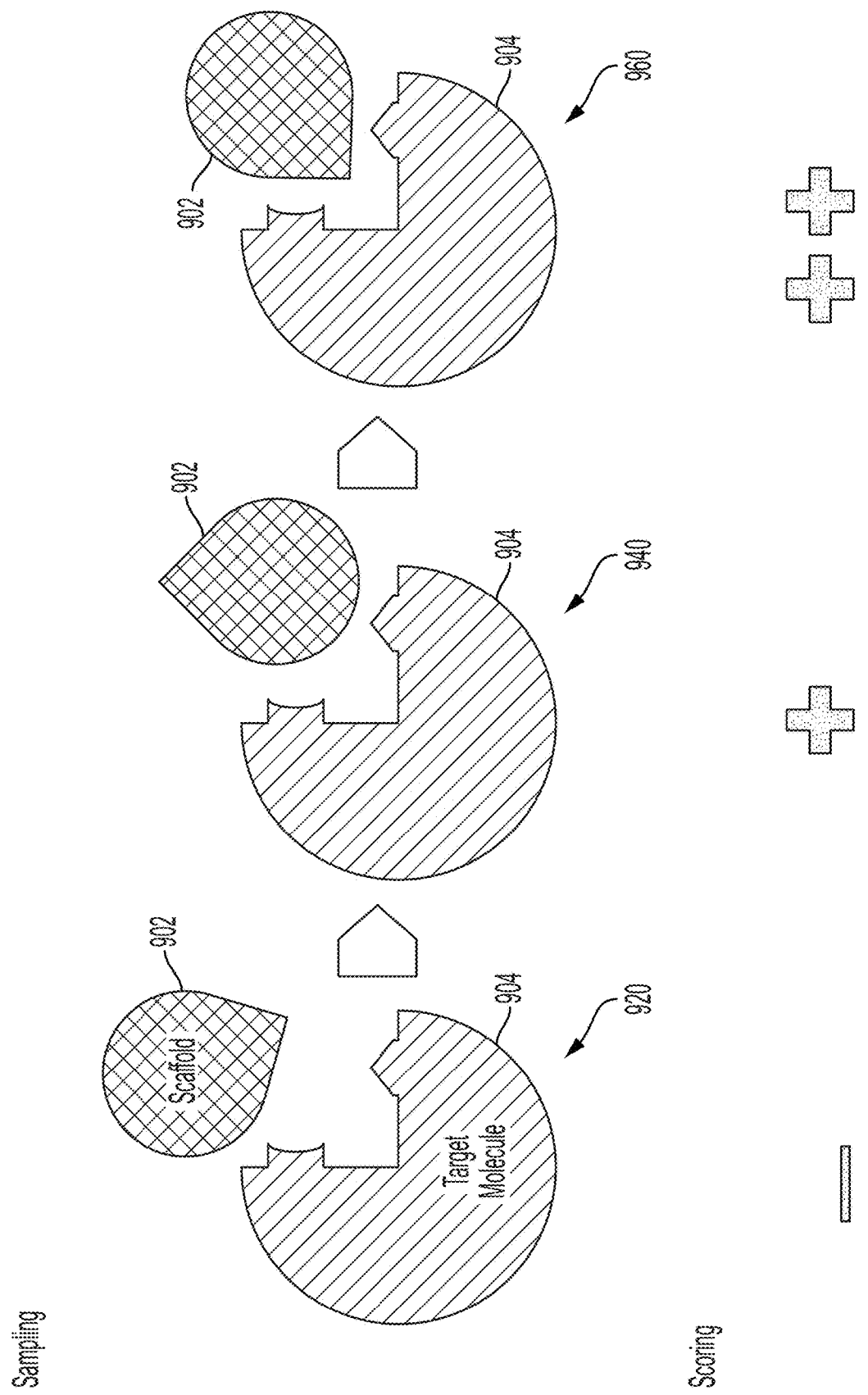
FIG. 8 is a schematic illustration of a scaffold docking approach, according to an illustrative embodiment.

FIG. 8 is a schematic illustration of a scaffold docking approach, which, in certain embodiments, may be performed by a scaffold docker module 102 as described herein. As shown in FIG. 8, a large molecule, such as a biologic may present to a particular target at a wide variety of different three-dimensional orientations—i.e., poses. Different poses place different portions of the biologic in proximity to the target, and, among other things, certain orientations may be favorable for binding and forming a complex with the target, while others are not. Without wishing to be bound to any particular theory, in certain embodiments, depending on a particular biologic's peptide backbone, certain poses may orient particular sub-regions, e.g., having particular local geometries, in a favorable manner with respect to a target or binding pocket thereof, so as to, for example, place a sufficient and/or maximal number of amino acid in proximity to atoms of the target. Moreover, due to, for example, particular amino acid sequences at various portions of the target, various physiochemical properties and/or features may be present and, accordingly, may influence interaction with backbone structures and potential amino acid interfaces created thereon in a complex fashion.

Accordingly, in certain embodiments, designing a custom biologic suitable for binding to a particular target begins with identifying one or more candidate peptide backbones and, for each, determining which, if any, poses provide favorable orientations for binding to the target. Candidate peptide backbones and poses thereof that are identified as favorable can then be used as a starting point—for example, a molecular scaffold—for downstream design steps that tailor amino acid side chain sequences to optimize molecular interactions with the target and design a binding interface of the custom biologic.

Figure 9:
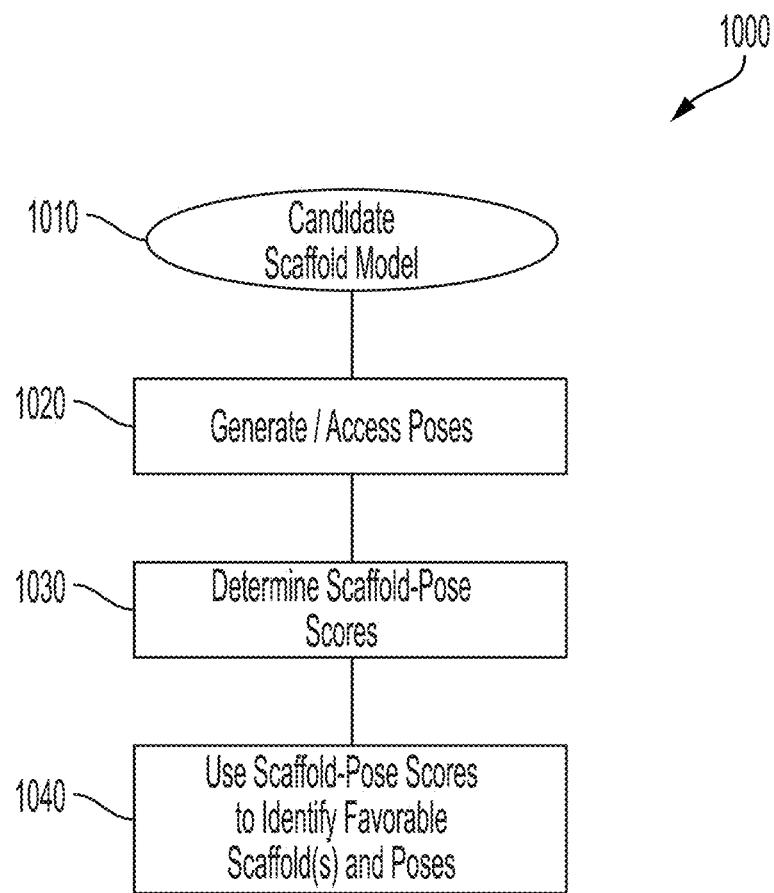
FIG. 9 is a block flow diagram of an example process for identifying favorable peptide backbones and poses thereof (e.g., for use in connection with a scaffold docking module as described herein), according to an illustrative embodiment.

Accordingly, in certain embodiments, custom biologic design tools described herein include and/or provide for a scaffold docker module that can be used to identify favorable candidate peptide backbones and poses thereof for binding to a desired target. Turning to FIG. 9, in certain embodiments, a scaffold docker module receives as input, accesses, or otherwise obtains structural models that represent candidate ligands and/or their peptide backbones 1010. In certain embodiments, structural models utilized by a scaffold docker module represent (e.g., solely) a peptide backbone of a protein or peptide molecule, omitting amino acid side chains, and are referred to herein as scaffold models.

In certain embodiments, scaffold docker module generates and evaluates multiple poses for a particular candidate peptide backbone by creating and/or accessing a plurality of scaffold-target complex models 1020. Each scaffold-target complex model comprises a corresponding candidate scaffold model and structural model of the target and represents the candidate peptide backbone at a particular pose with respect to the target. In certain embodiments, scaffold-target complex models to be evaluated are generated by applying three-dimensional rotation and/or translation operations to scaffold model to represent various poses. Rotation and/or translation operations to be applied to a scaffold model may be determined, for example, via a random sampling approach, or, additionally or alternatively, in certain embodiments, via certain pose generation processes described herein. In certain embodiments, rotation is homogeneously sampled, for example via sampling along a (e.g., fixed) interval (e.g., 5 degrees, 10 degrees, 15 degrees, 20 degrees, etc.). In certain embodiments, a particular rotational space, such as using a Hopf Fibration, as described herein, is used. In certain embodiments, use of a Hopf Fibration does not rely on degrees, but rather on the number of points that will homogeneously sample a rotation sphere.

In certain embodiments, scaffold docker module may evaluate generated scaffold-target complex models and determine 1030 scaffold-pose scores—e.g., numerical values that provide a quantitative measure of suitability or favorability of particular complex models and the poses that they represent. Based on the determined scaffold-pose scores, a scaffold docker module may then select a subset of scaffold-target complex models, e.g., as representing favorable candidate peptide backbones and poses thereof 1040. A selected subset may then be provided to and/or used a starting point for other modules, such as an interface designer module as described herein.

For example, as shown in FIG. 8, both position and orientation of a particular candidate scaffold model 902 with respect to the target 904 may be varied, to generate multiple candidate poses and thereby sample a search space of three dimensional orientations and positions of the candidate scaffold model with respect to the target. In certain embodiments, one or more regions of interest of the target are identified and candidate poses are generated and evaluated so as to orient and assess viability/potential performance, as described in further detail herein, of the candidate scaffold model with respect to the one or more regions of interest of the target. These target regions of interest may be, for example, putative binding sites and may be, in certain embodiments, pre-selected by a user and/or automatically identified, e.g., based on known binding sites, structural features, output of other modules, etc.

The scaffold docker module computes scores based on the sampled poses, in order to identify those most favorable for binding. For example, as illustrated in FIG. 9, a low score is computed for pose 920 (e.g., in pose 920, neither the location nor orientation of scaffold model 902 are favorable), an intermediate score is computed for pose 940 (e.g., in pose 940, a position of scaffold model 902 is favorable, but its orientation is not) and a high score computed for pose 960, e.g., due to a favorable orientation and position of the candidate scaffold.

In certain embodiments, a scaffold docker module utilizes an AI-based scoring approached whereby a machine learning model is used to evaluate prospective scaffold-target complex models and determine scaffold-pose scores. In this manner, approaches described herein leverage extensive structural data on existing native protein-protein and/or protein-peptide complexes along with tailored training procedures to create a scaffold predictor model that implements a trained machine learning algorithm to assess which candidate peptide backbones and poses thereof (as represented via scaffold-target complex models) are favorable for binding to a particular target.

i. Training Data Set Construction
Native and Artificial Scaffold-Receptor Complex Models
In certain embodiments, a scaffold predictor model is a machine learning model that receives, as input, a representation of at least a portion of a particular scaffold-target complex model and determines, as output, a scaffold pose score. In certain embodiments, a scaffold pose score is a numerical value, for example a probability value ranging from zero to one. In certain embodiments (e.g., where a binary classifier is used), scaffold pose score may further transformed into a Boolean value, e.g., based on a comparison of with a threshold value.

For example, in certain embodiments, as described herein, a scaffold predictor model may be trained to differentiate between and/or determine a measure of similarity between representations of native complexes (e.g., which have been demonstrated to be physically viable) and artificially generated complexes that have varying features, which may not be suitable for binding. In particular, in certain embodiments, in order to train a machine learning model in this manner, examples of both native and artificial are used as training data. Native complex examples may be obtained and curated from datasets of existing biological complexes. Representations of native complexes are, by definition, examples of physically viable complexes, and represent candidate peptide backbones and poses that are suitable for binding. In certain embodiments, for example to provide examples of complexes that have structural features of varying degrees of suitability for binding, artificial complex models are generated. As described herein, artificial complex models may be generated by perturbing native complex models. In certain embodiments, measures of an extent of the perturbation are determined. These measures, referred to as pose quality metrics, allow various artificial complex models to be labeled, selected, sorted, etc., based on their similarity to existing native complex models. Accordingly, together with examples of native complexes, creating and labeling artificial complex models in this manner provides for creation of a labeled dataset that can be used to train a machine learning model to differentiate between and/or quantify similarities between successful native complexes, native-like artificial complexes that may reflect successful features, and artificial complexes that are do not have features suitable for binding. Such a machine learning model, when presented with new data, such as a candidate scaffold-target complex model, may then be used to generate a scaffold-pose score that reflects the machine learning model's assessment of how 'native-like' the structure appears. In this manner, scaffold-pose scores can be utilized to identify and design candidate peptide backbones and poses that will be suitable for binding to a particular target.

Pose Quality Metrics
In certain embodiments, one or more pose quality metrics are computed for scaffold-target complex models used as training data. In certain embodiments, pose quality metrics are computed for native scaffold-target complex models as well as artificial scaffold-target complex models. As explained in further detail herein, pose quality metrics can be used to ensure training examples to be used to train the scaffold docker's machine learning model are sufficiently varied.

Figure 10:
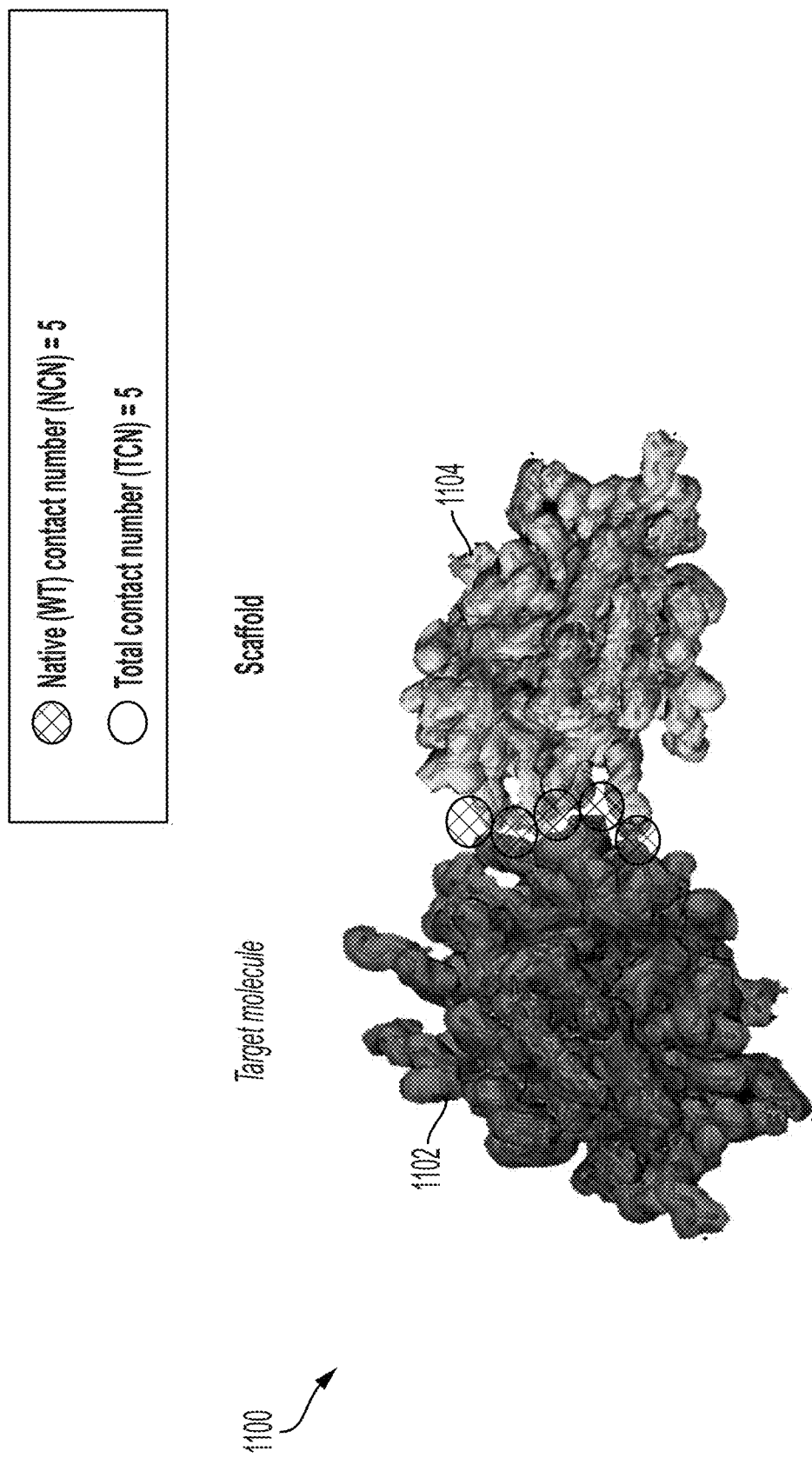
FIG. 10 is a schematic of a representation target (e.g., a particular receptor) in a complex with a scaffold model, according to an illustrative embodiment.
Figure 11:
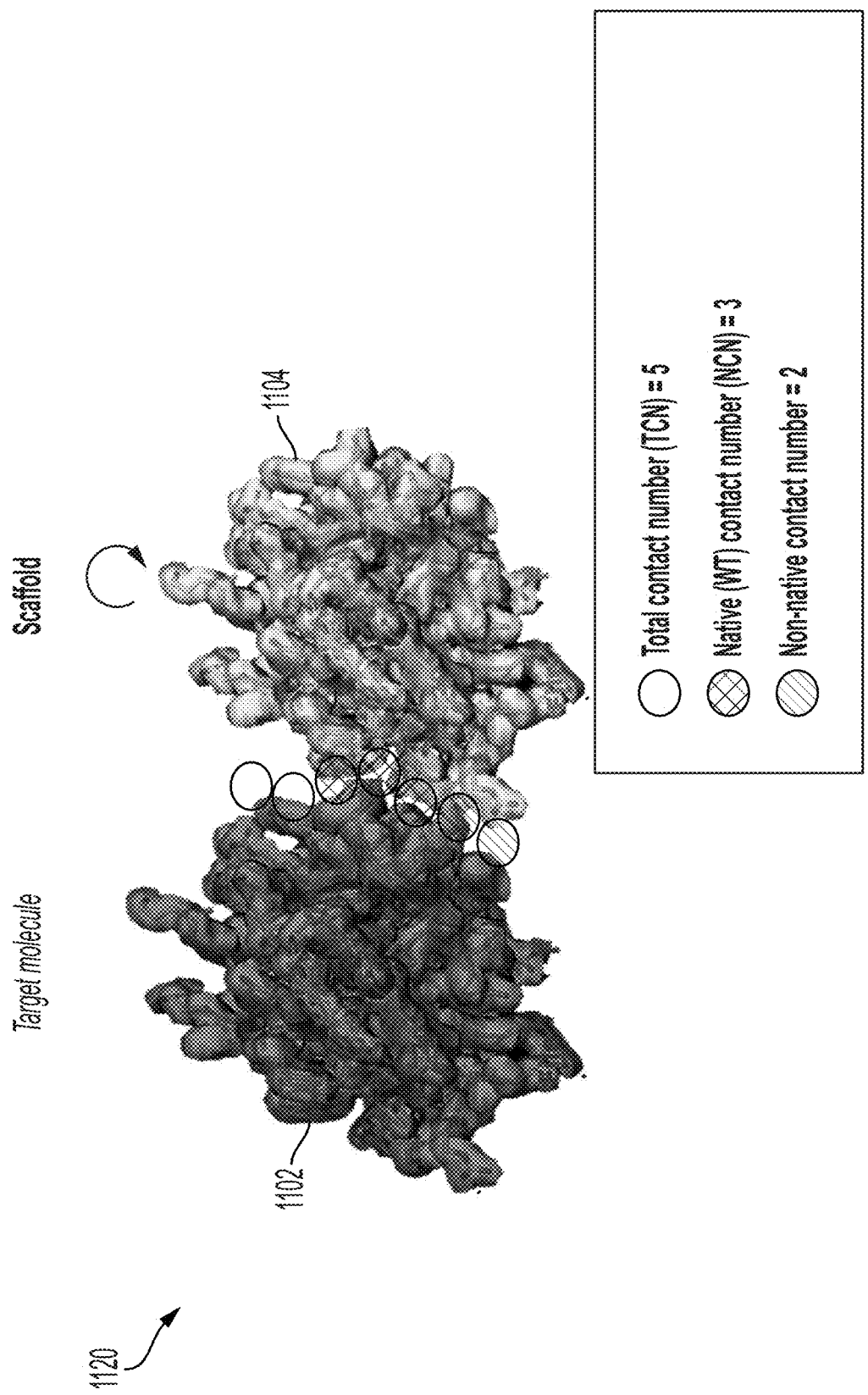
FIG. 11 is a schematic of a representation target molecule (e.g., a particular receptor) in a complex with a scaffold model, according to an illustrative embodiment.

Turning to FIGS. 10 and 11, in certain embodiments, pose quality metrics are determined based on a number of identified contact locations between a scaffold and target in a complex. In certain embodiments, contact locations may be identified as locations wherein a first side chain atom (e.g., beta carbon and/or hydrogen) of a scaffold is within a particular contact threshold distance of a first side chain atom of a target (e.g., contact locations do not necessarily refer to points of physical contact, but rather locations of sites on a scaffold and target that are in sufficient proximity to each other to be likely to influence binding). In certain embodiments, the contact threshold value is 8 Å (i.e., 8 Angstroms) is used. In some embodiments, other thresholds may be used for defining a contact (such as less than 3 Å, less than 4 Å, less than 5 Å, less than 6 Å, less than 7 Å, less than 9 Å, less than 10 Å, less than 12 Å, less than 15 Å, less than 20 Å, as well as other suitable thresholds). In certain embodiments, contact locations may be identified in a manner analogous to that described herein with respect to identification of hotspots.

In certain embodiments, a native contact number (NCN) is determined to quantify the number of native contacts in a particular scaffold-target complex model. As used herein, a native contact refers to a contact present in a native complex. In certain embodiments, a total contact number (TCN) is determined to quantify a total number of contacts in a particular scaffold-target complex model. FIG. 10 shows an example of a native scaffold-target complex model 1100. As shown in FIG. 10, five contacts (red circles) are identified between scaffold 1104 and target molecule 1102. Since FIG. 10 shows a native scaffold-target complex model 1100, each contact is a native contact, and both NCN and TCN for scaffold-target complex model 1100 equal five.

FIG. 11 shows an example of an artificial scaffold-target complex model 1120. Scaffold-target complex model 1120 is derived from native scaffold-target complex model 1100. In particular, it utilizes a same scaffold model 1104 and target 1102, but a pose of scaffold model 1104 is varied (e.g., by applying a random three-dimensional rotation and/or translation operation to scaffold 1104) to create a new, non-native pose. As shown in FIG. 10, with the new pose, three of the original, native contacts are maintained (red circles) and two native contacts are removed (open circles). The new pose also results in two new, non-native contacts (purple circles). Accordingly, NCN and TCN values for generated artificial scaffold-target complex model 1120 are three and five, respectively.

According, in certain embodiments, a training data set may be constructed by (i) obtaining native scaffold-target complex models based on experimentally derived structural data and (ii) generating artificial scaffold-target complex models, for example by rotating and/or translating scaffold models of native-scaffold-target complex models to generate new poses. In certain embodiments, values of pose quality metrics such as NCN and TCN can be computed for each (native and artificial) scaffold-target complex model.

Figure 12:
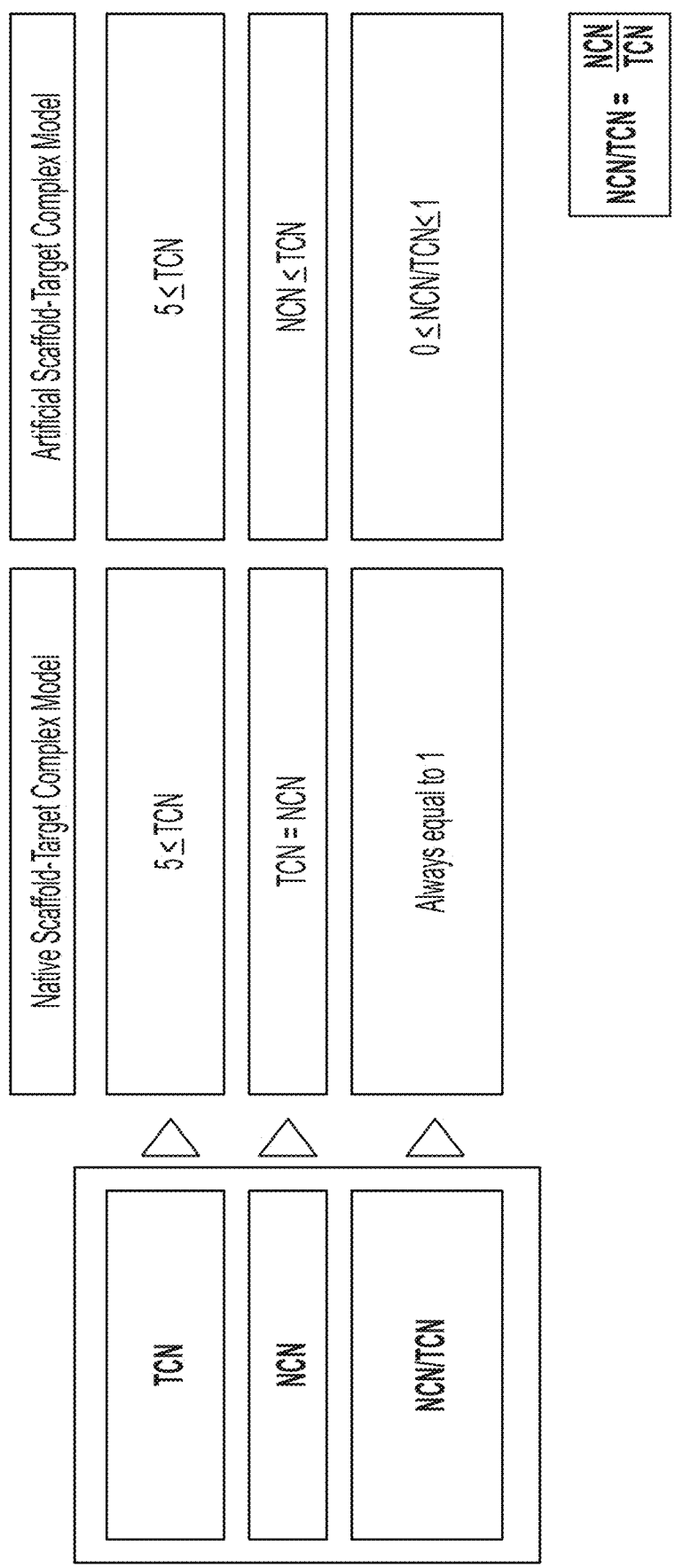
FIG. 12 is a diagram of comparing certain features of various pose quality metrics described herein, according to an illustrative embodiment.

For example, FIG. 12 summarizes and compares certain features of NCN and TCN values computed for native and artificial scaffold-target complex models. In certain embodiments, as shown in FIG. 12, pose quality metrics can be combined to yield additional metrics. For example, NCN and TCN may be combined into a single pose quality metric computed as the ratio, NCN/TCN. In certain embodiments, pose quality metrics such as NCN and TCN can be used to evaluate and select particular native and artificial scaffold-target complex models for inclusion and/or exclusion from a training data set. For example, as shown in FIG. 12, in one example, only scaffold-target complex models with TCN values above a threshold value (e.g., five) were selected for inclusion in the training data set. In this manner, potentially spurious native complex examples with a small number of contacts were filtered out. Other filtering approaches, threshold values, etc. based on NCN, TCN, NCN/TCN values as well as other pose quality metrics may be used additionally or alternatively.

Figure 13:
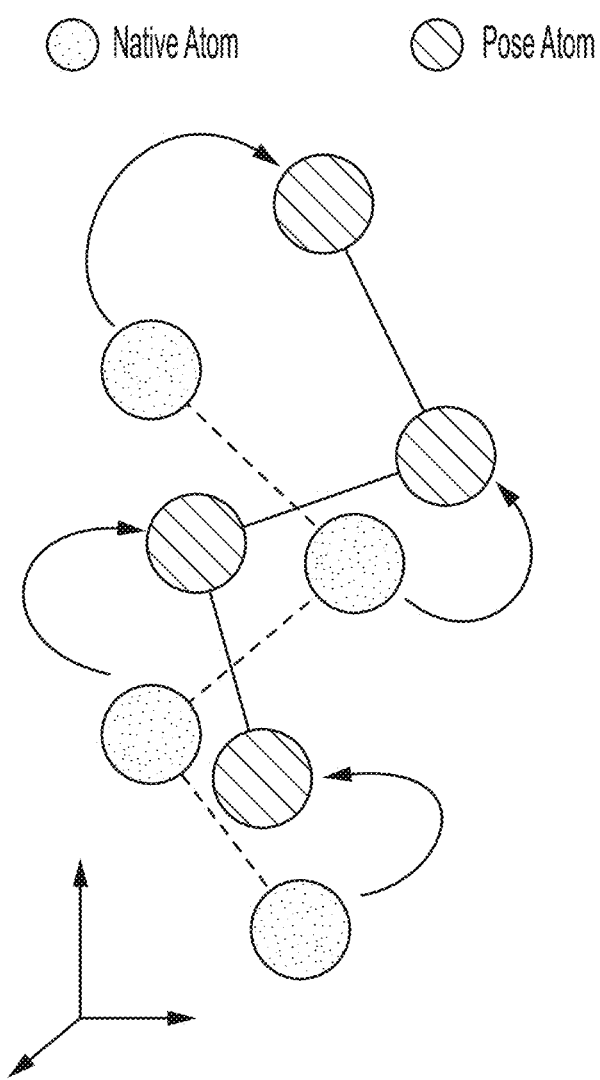
FIG. 13 is a schematic illustrating calculation of a root mean squared distance (RMSD) value, according to an illustrative embodiment.

In certain embodiments, a pose quality metric may provide a measure of similarity between an artificial scaffold-target complex model and a native scaffold-target complex model from which it is derived. For example, FIG. 13 illustrates calculation of a root mean squared distance (RMSD) between atoms of two structures. In certain embodiments, an RMSD between atoms of (i) a particular native scaffold-target complex model and (ii) a particular artificial scaffold-target complex model derived from the particular native scaffold-target complex model may be used as a pose quality metric. In particular, as explained herein, in certain embodiments an artificial scaffold-target complex model may be derived from a native scaffold-target complex model by applying three-dimensional rotations and/or translations to a scaffold model of the native-scaffold complex model in order to place it in a new, artificial pose relative to the target. Accordingly, in certain embodiments an RMSD (Native, Pose) value can be computed as follows:

$$RMSD(\text{Native, Pose}) = \sqrt{\frac{1}{n}\sum_{i=1}^{n} \|\text{Native}_i - \text{Pose}_i\|^2} =$$

$$\sqrt{\frac{1}{n}\sum_{i=1}^{n} (\text{Native}_{i,x} - \text{Pose}_{i,x})^2 + (\text{Native}_{i,y} - \text{Pose}_{i,y})^2 + (\text{Native}_{i,z} - \text{Pose}_{i,z})^2}$$

Accordingly, in certain embodiments, RMSD(Native, Pose) computes the average of the distances between locations of atoms of the initial, native complex model and their new, shifted locations, as they are in the new pose that the artificial complex model represents. In this manner, RMSD (Native, Pose) may provide a measure of similarity between an artificial scaffold-target complex model and a native scaffold-target complex model from which it was derived.

Accordingly, as illustrated in FIG. 14, in certain embodiments, pose quality metrics such as those described herein reflect quality of a particular pose represented by a scaffold-target complex model. In certain embodiments, a pose quality metric provides a numerical measure of similarity between a pose represented by a particular scaffold-target complex model and a native pose (e.g., "native-ness"). Pose quality metrics may vary with, or inversely to a level of similarity to a native pose. For example, schematic 1420 illustrates how pose quality or similarity to a native complex varies with NCN/TCN value. Pose quality metric NCN/TCN has values ranging from zero to one. A value of NCN/TCN increases, approaching one, with increasing similarity between a pose represented by a particular complex model and a native pose. As explained herein, since NCN=TCN for a native complex model, a NCN/TCN value of one indicates a native complex model. For example, schematic 1440 illustrates how pose quality or similarity to a native complex varies with RMSD value. As explained herein, RMSD reflects a relative geometric distance of atoms of a particular complex model to a native complex model. An RMSD of zero indicates a particular complex model is a native complex model. Increasing RMSD reflects increasing distance between molecular structures represented in an artificial complex model and their native positions and orientations. As explained in further detail herein, pose quality metrics such as RMSD and NCN/TCN can be used to label potential training examples. By virtue of this labeling approach, examples can be selected to sample a variety of RMSD and NCN/TCN values (e.g., a uniform sample across a particular range of values), thereby providing training data that exposes a machine learning model to a sufficient degree of variation in pose qualities.

In certain embodiments, values such as TCN, NCN, RMSD can be used in a preliminary filtering step, e.g., to filter out irrelevant poses. For example, in certain embodiments, structures (e.g., obtained from databases) having computed RMSD values above a particular threshold are excluded from further evaluation. Such filtering approaches may be used at various steps in processes described herein.

In certain embodiments, artificial scaffold-target complex models may be generated via approaches other than that described with respect to FIG. 11 and may be used additionally or alternatively to the approach described herein with regard to FIG. 11. For example, in certain embodiments, artificial scaffold-target complex models may be created by combining structural representations of two or more monomers, e.g., structural models representing native peptide and/or protein monomers, and, e.g., arranging each monomer at various poses with respect to each other. In certain embodiments, artificial scaffold-target complex models may be derived from native scaffold-target complex models by altering a scaffold model portion of the native scaffold-target complex model, to produce an artificial scaffold-target complex model wherein the scaffold portion represents a non-native (e.g., artificial), perturbed, backbone.

Training Dataset Generation

Figure 15:
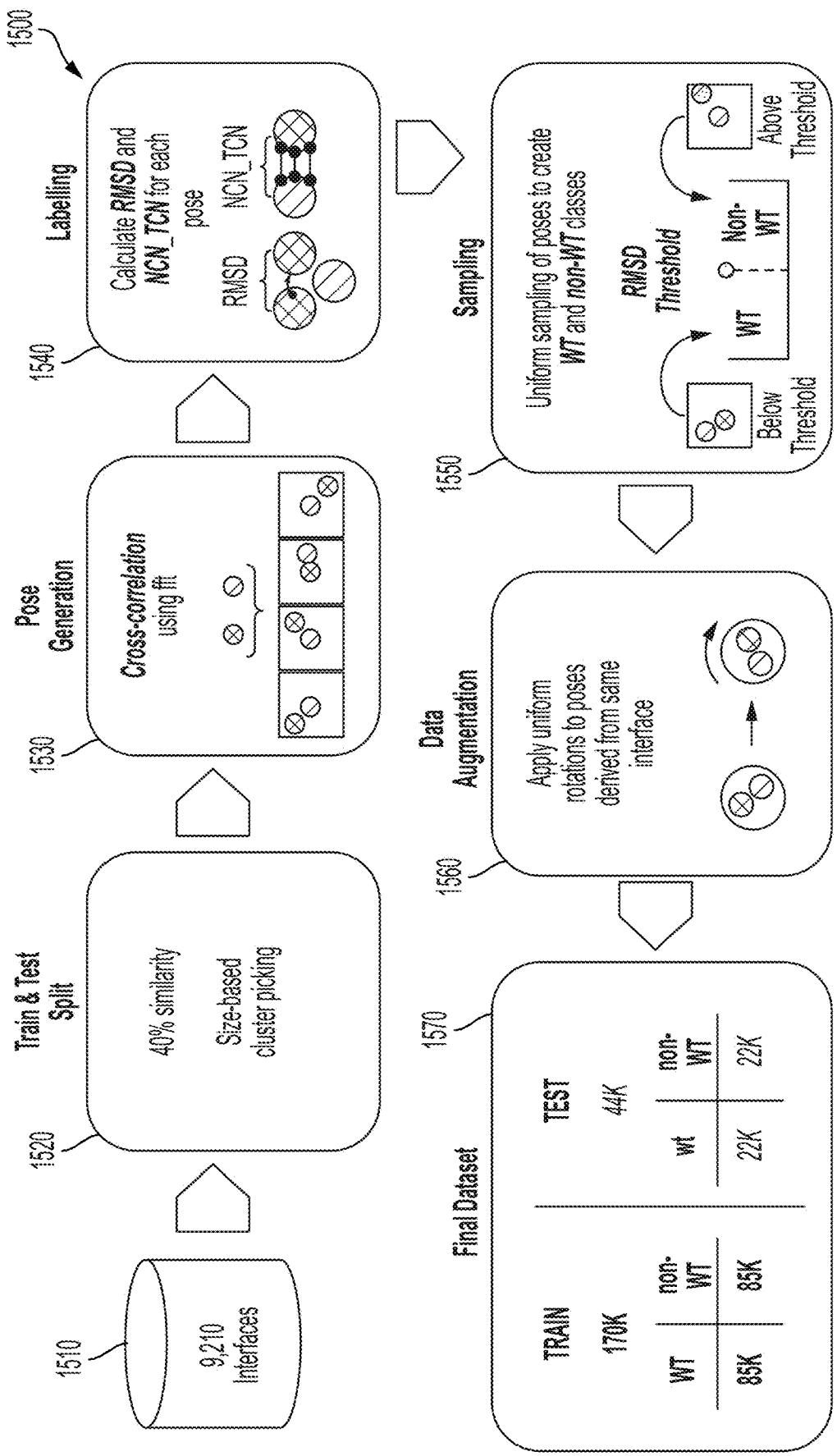
FIG. 15 is a block flow diagram of an example process for creation of a training dataset for use in training a machine learning model, according to an illustrative embodiment.

For example, FIG. 15 shows an example process 1500 for generating datasets for training and testing (e.g., validating) a machine learning model to determine scaffold pose scores, used in certain embodiments. Specific numbers and description (e.g., in boxes) in FIG. 15 describe values and steps carried out in a particular exemplary implementation of process 1500, but values and particular approaches may vary from implementation to implementation.

In example process 1500, an initial dataset (e.g., of native complex models) is obtained from one or more databases 1510, and the initial dataset may be split into initial training and testing datasets 1520, for example according to process 400 described herein. Complex models of the initial training and testing datasets may be used to create new, artificial complex models in a pose generation step 1530, for example by applying three dimensional rotation and/or translations to scaffold models of native complex models. In certain embodiments, pose generation step 1530 encompasses an initial filtering approach used to exclude poses that generate highly improbable and/or non-viable complexes, such as translations that would generate significant overlap between a scaffold model and target, or place them too far apart to interact/bind. One such approach is described in further detail below, with regard to FIGS. 16A and 16B (e.g., process 1600). In certain embodiments, one or more pose quality metrics are calculated for complex models generated via pose generation step 1530 and computed pose quality metrics are used to label the generated complex models 1540. Complex models may then be selected for inclusion in final training and/or testing data sets according to computed pose quality metrics via a sampling step 1550. For example, in certain embodiments, complex models are selected so as to uniformly sample a range of one or more particular pose quality metrics, such as NCN/TCN and/or RMSD.

In certain embodiments, in sampling step 1550, complex models are also assigned to two or more classes and labelled accordingly. For example, for a machine learning model that performs a binary classification function, complex models may be assigned to one of two classes (e.g., each complex model identified as an example of one class or another), and used to train the machine learning model to differentiate between the two classes. In certain embodiments, more than two classes may be used, for example to train a machine learning model that performs non-binary classification. In certain embodiments, complex models are assigned to two or more classes based on threshold values for one or more pose quality metrics. In certain embodiments, complex models are not sorted into classes, but instead labeled with a numerical value, for example determined from (e.g., including equal to) a pose quality metric. Such an approach may be used, for example, to train a regression model type of machine learning model.

In certain embodiments, an additional, data augmentation step 1560 is performed. In certain embodiments, as described herein, data augmentation step 1560 creates additional versions of examples of complex models by rotating entire models in three dimensions. As described herein, this approach can be used to account for the propensity of CNNs to perceive rotated versions of otherwise identical structures differently.

In this manner, final training and testing datasets may be generated 1570 and used to establish weights of a machine learning model for use in evaluating candidate scaffold-target complex models.

Example Training Dataset Construction Implementations

Figure 16A:
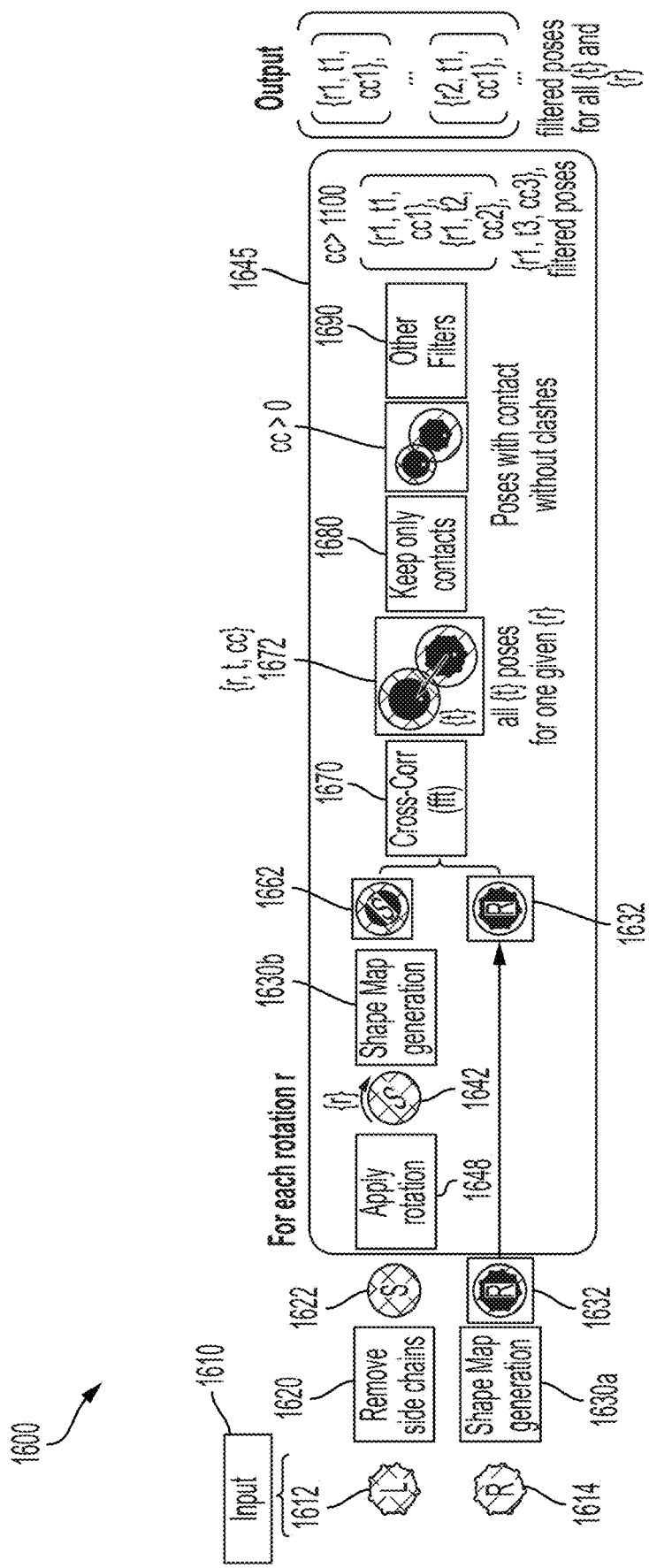
FIG. 16A is a block flow diagram of an example pose generation process, according to an illustrative embodiment.
Figure 17:
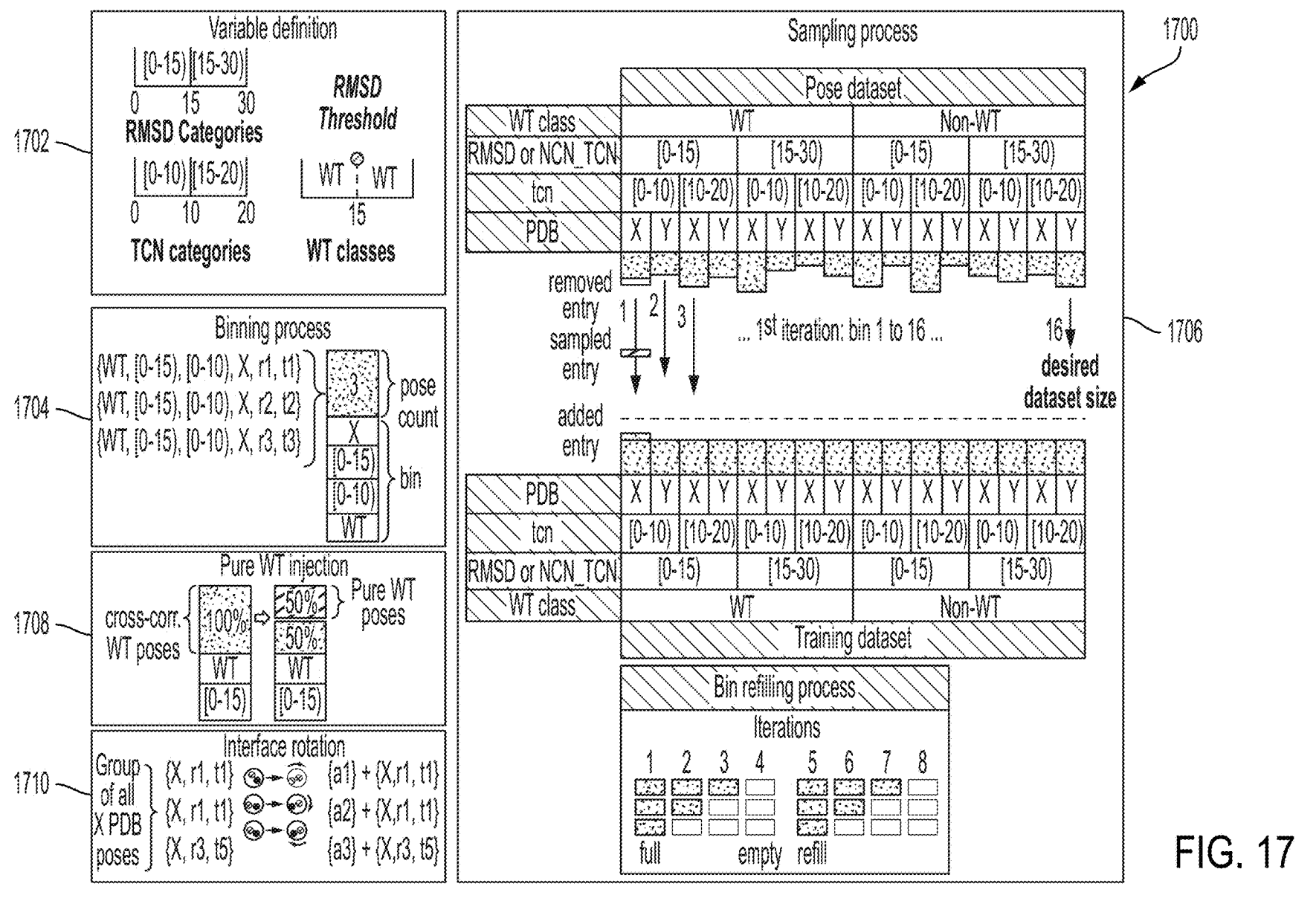
Figure 18:
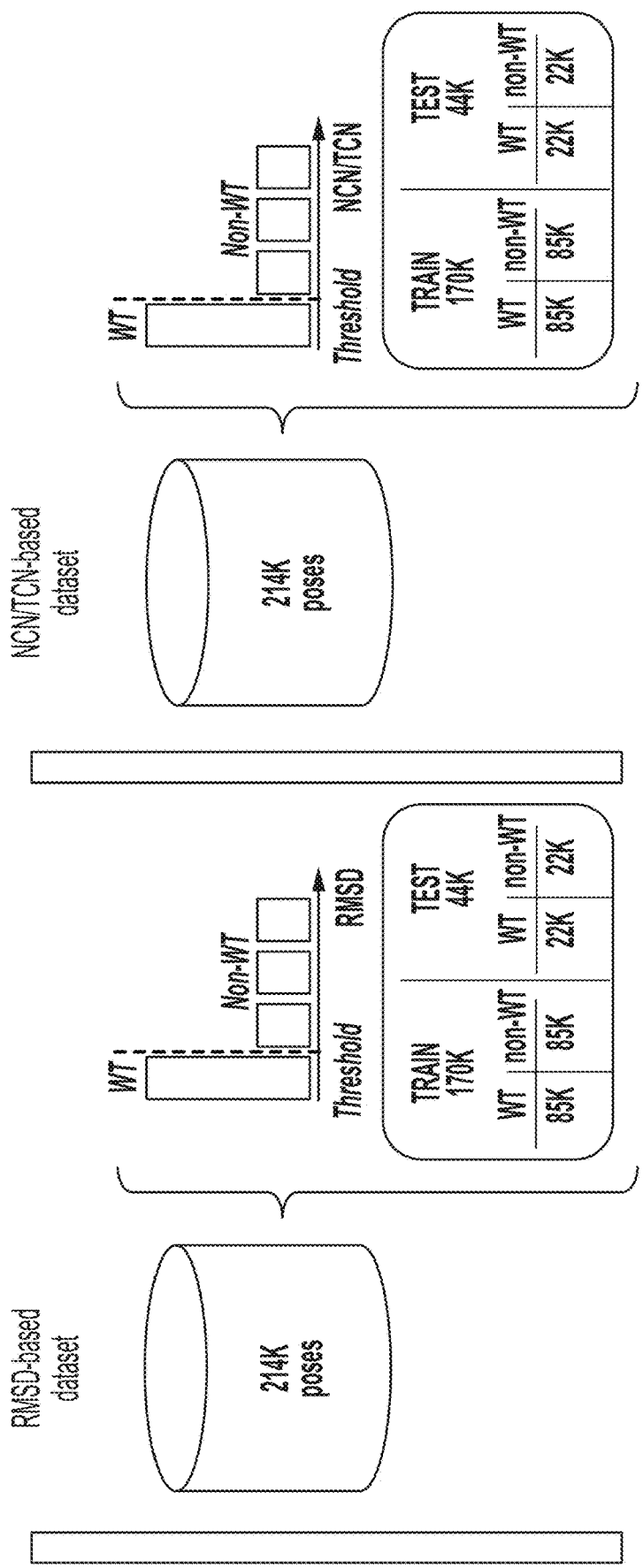
FIG. 18 is a schematic illustrating an example approach to creation of various datasets comprising labeled examples of two classes, based on pose quality metrics, according to an illustrative embodiment.

FIGS. 16A to 20 show exemplary implementations of various steps in process 1500, for building training datasets. The implementation shown in FIGS. 16A to 20 is used to generate training data in which complex models are assigned to two classes, and was used to train a binary classifier machine learning model to distinguish between complex models that were likely to represent native complex, and complex models that were likely to represent artificial structures, as perceived via the machine learning model. As described in further detail herein, FIGS. 16A and 16B show an example approach for generating poses, suitable for use at step 1630, and filtering to exclude those that would produce highly non-physical complexes in a rapid and efficient manner. FIG. 17 describes a particular implementation of sampling step 1550, which may be used in certain embodiments. FIG. 18 describes an approach for assigning complex models to two classes.

Figure 16B:
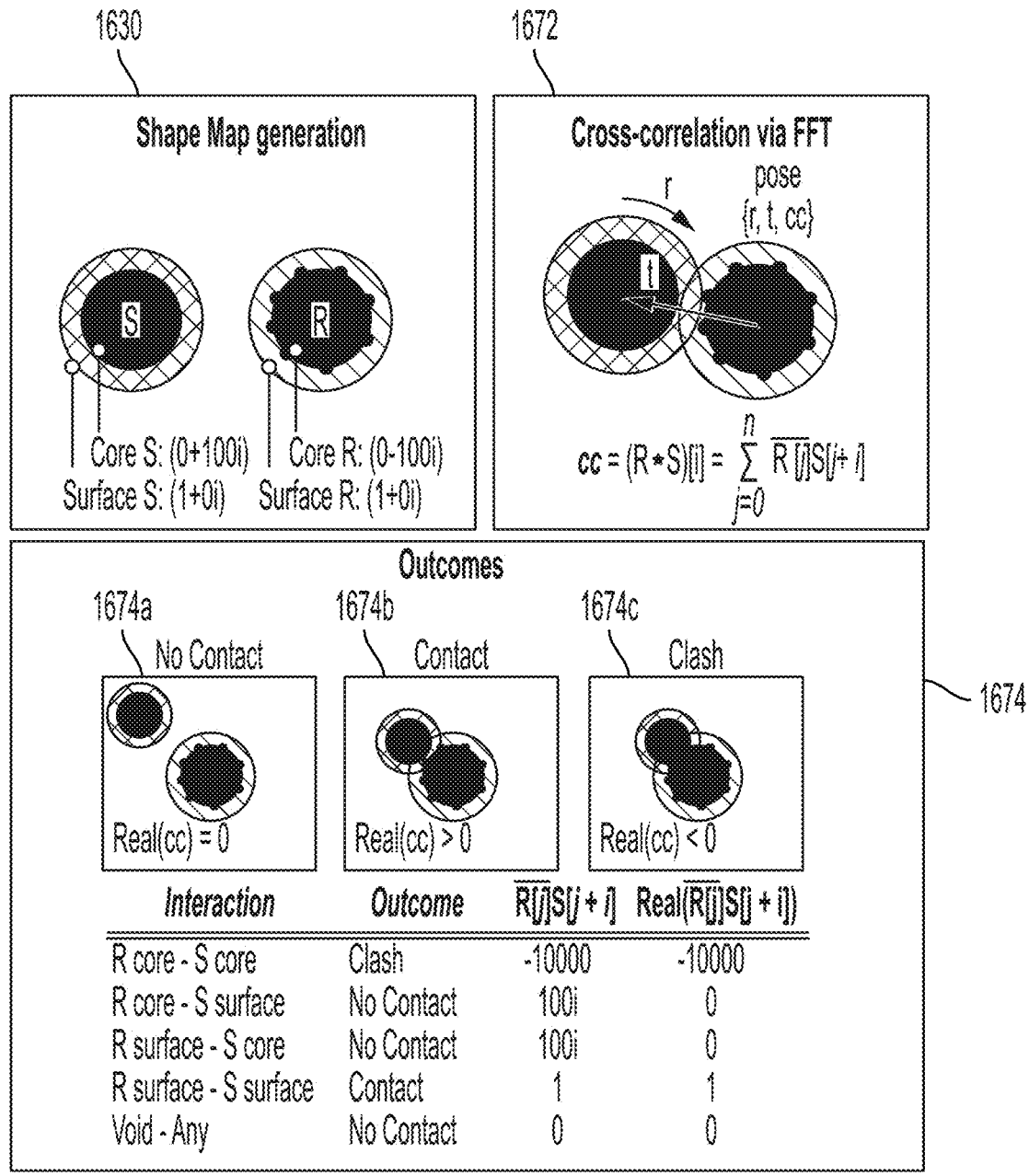
FIG. 16B is a schematic illustrating an approach to pose generation, according to an illustrative embodiment.

FIGS. 16A and 16B illustrate an example process 1600, whereby ligand and receptor models can be represented via matrices (e.g., 3D matrices or tensors) of complex numbers, and an efficient cross-correlation approach used to identify poses that are predicted to place molecule surfaces in sufficient proximity for binding, and filter out those that likely create non-physical clashes and/or place a receptor and ligand too far apart for binding to occur. In certain embodiments, process 1600 begins with receiving and/or accessing, as input 1610, a ligand model 1612 and a receptor model 1614. In certain embodiments, amino acid side chains are removed 1620 from ligand model 1612 to create a scaffold model 1622.

In certain embodiments, a shape map representation 1632 is created from receptor model 1614 via shape map generation step 1630a. In certain embodiments, as shown in FIG. 16B, a shape map representation may be created from a particular constituent partner (e.g., a ligand or receptor) of a biological complex by labeling each atom in the particular partner as surface or core according to their solvent-accessible surface area (SASA) value. A shape map representation is then created 1630 by representing the particular partner as centered on a three-dimensional grid (e.g., matrix), and for each labelled atom, assigning a complex number to grid points within a pre-defined radius (e.g., surrounding the atom). In certain embodiments, the pre-defined radius for a particular atom is or is based on a Van Der Waals radius for the particular atom. In certain embodiments, the particular complex number assigned to grid points associated with a particular is determined based on a label of the particular atom. For example, in certain embodiments, grid points associated with core and surface atoms of a scaffold model representing a backbone of a ligand are assigned values of 0+100i and 1+0i, respectively. In certain embodiments, grid points associated with core and surface atoms of a receptor model representing a receptor of a complex are assigned values of 0-100i and 1+0i, respectively.

Turning to FIG. 16A, in this manner, receptor shape map 1632 may be created from receptor model 1614. Scaffold model 1622 may then be rotated via a rotation {r} 1640 to create a rotated scaffold model 1642, from which a shape map representation—rotated scaffold shape map 1662—is then created 1630*b*.

In certain embodiments, rotated scaffold shape map 1662 and receptor shape map 1632 are then cross correlated 1672. In certain embodiments, cross-correlation 1672 is performed via a Fast Fourier Transform (FFT). In certain embodiments, cross correlation scans rotated scaffold shape map 1662 and receptor shape map 1632 across each other, calculating a cross-correlation value at a particular translation {t} of rotated scaffold shape map 1662 relative to receptor shape map 1632. In this manner, for a particular rotation {r}, cross-correlation 1672 samples a range of possible translations, computing, for each rotation-translation pair, {$r_i, t_j$}, a corresponding cross-correlation value $cc_{ij}$. In particular, in certain embodiments, cross-correlation step 1672 outputs a grid where each point corresponds to a different translation of a same rotated pose and holds a cross-correlation (cc) value.

In certain embodiments, a cross-correlation value calculated for a particular rotation-translation pair can be used to infer whether a particular pose represented by the particular rotation-translation pair would result in one of three outcomes 1674—no contact 1674*a*, contact 1674*b*, or a clash 1674*c*. As illustrated in FIG. 16B, a no contact 1674*a* outcome indicates that a complex model formed by orienting scaffold model 1622 according to the particular rotation-translation pair with respect to receptor model 1614 would place the two too far apart for binding to be feasible (e.g., sufficiently likely). In certain embodiments, a no contact 1674*a* outcome can be identified via a cross-correlation value having a real part equal to zero. In certain embodiments, clash outcomes 1674*c* have a large real negative contribution to their corresponding cross-correlation value, while contact outcomes 1674*b* have small real positive contribution. As illustrated in FIG. 16B, clash outcomes indicate placements of a scaffold model and a receptor model that cause excessive overlap, which would also not likely result in a viable complex. Contact outcomes are indicative of poses that place a scaffold model in sufficient proximity (e.g., not necessarily perfect physical contact) to a receptor model to correspond to a complex with potential for binding to occur. Accordingly, contact outcomes are desirable, while clashes and no contact outcomes are not.

Accordingly, in certain embodiments, {r,t} pairs that result in clash and/or no contact outcomes are filtered out, and only contact outcomes are retained 1680. In certain embodiments, other filters may also be utilized 1690, for example to retain poses with a high likelihood of being successful. For example, in certain embodiments a threshold value may be determined empirically, for example by evaluating cross-correlation values obtained from shape map representations of successful native complex models. For example, in one embodiment, it was found that an empirically determined threshold of 1100 captured 90% of WT Poses. Accordingly, by filtering poses ({r,t} pairs) having real parts of their cross-correlation value below 1100, only poses closely resembling native poses can be retained. Accordingly, in this manner, for a particular rotation, a set of filtered poses can be generated. In certain embodiments, as illustrated in FIG. 16B, this approach (e.g., steps 1640 through 1690) can be iteratively applied to multiple rotations 1645 to generate, for each rotation, a set of filtered poses. Sets of filtered poses generated in this manner can then be combined to create a final set of filtered poses for multiple rotations and translations.

FIG. 17 illustrates an example sampling approach, used in certain embodiments. In example sampling process 1700, at a variable definition step, examples are labeled wildtype (WT) or non-wildtype (non-WT) based on a threshold RMSD variable, or other pose quality metrics as described herein. During a binning process poses may be grouped into classes according to one or more of the WT variable definition, a RMSD category, a TCN category, and a protein database (PDB) category, among other possible categories. During a sampling process, a single pose from each bin is sampled sequentially, one at a time, alternating between bins, and not returning to a given bin until each of the other bins have been sampled from in the interim. This sampling process continues until a given bin is empty, at which point it may be refilled with its original dataset. The alternating of bins during model training prevents the model from becoming overly constrained and/or "over-tuned" to a specific sub-set of the overall dataset. During pure-wild type injection, about 50% (e.g., or from about 40% to 60%, or from about 30% to about 70%, e.g., up to 100%) of the cross-correlated generated poses in the WT class may be replaced with WT poses (i.e., the original, native, poses). During interface rotation, poses may be grouped by PDB category and may be assigned a homogenously sampled augmentation rotation that may be applied to the entire pose.

Without wishing to be bound to any particular theory, it is believed this type of sampling procedure removes biases, promotes generalization and prevents undesired correlation. For example, this approach may decorrelate contacts seen by model (TCN) and label (e.g., native/wild-type or non-native/non-wild-type), so that the model does not learn to count contacts and/or is not biased by a size of molecules. In particular, as described herein, the label is a metric that represents the quality of the pose—e.g., how likely it is to be a pose with native like interface properties and therefore how likely it is for the receptor and the ligand to bind. The model needs to predict this by learning a set of features from the data (e.g., training data). The TCN metric is essentially a number of contacts between a receptor and ligand in a particular pose. It is believed that the model should in theory learn this feature quite easily as it will "see" that there are many atoms close to each other (i.e. in contact) at the interface. It is believed that a CNN models will be quite good at identifying this type of feature.

Again, without wishing to be bound to any particular theory, a model may, in certain embodiments, learn to identify TCN and to use it (e.g., alone, excessively) to predict the label. However, predicting a label based, for example solely on a learned correlation between a TCN feature and label and/or excessively weighting/relying on the TCN feature may be undesirable.

In particular, non-native poses can have both large and small interface contact areas, so it is not a predictive feature of how native the interface is. Moreover, large molecules tend to have larger contact area than small molecules and by correlating the TCN and the label the model will tend to predict higher label values for large molecules (e.g., without regard to whether they are a native or non-native pose). Accordingly, more accurate predictions and performance are obtained by avoiding and/or limiting an extent to which a model learns this correlation, as it can lead to unintended biases.

Accordingly, in certain embodiments, approaches described herein address this challenge by creating datasets in which these two metrics are purposely uncorrelated (at least to the extent to which this is possible given the data at hand). Such training data set provide examples of poses with high TCN and low label, high TCN and high label, low TCN and high label, etc. By providing multiple combinations in examples where, e.g., high TCN is not necessarily associated with a high label value, it is believed that the model does not learn to correlate high TCN with label, and rather learns other more relevant features to make an appropriate prediction.

Additionally or alternatively, the approach aims to reduce PDB category redundancy to prevent memorization of specific PDB categories by the model, and uniformly distributes labels to prevent bias in the model predictions. For example, it is believed that having a dataset with a uniform label distribution prevents the model from learning biases during training.

In certain embodiments, a labeled dataset constructed in this fashion may be combined with one or more additional labeled datasets, e.g., created via other sampling procedures. For example, an additional labeled dataset may be created by random sampling (e.g., of bins).

FIG. 18 illustrates an approach to generating various training datasets, used in certain embodiments. In particular, in certain embodiments, training examples may be labeled as native-like (e.g., also referred to as wild-type) and non-native (e.g., also referred to as non-wild type) based on one or more pose quality metrics, such as RMSD and NCN/TCN. For example, in certain embodiments, various complex models to be used training examples can be labeled as native-like or non-native by comparing their RMSD values to a particular RMSD threshold value. In certain embodiments, structures may be discarded from the training dataset based on a comparison with a (e.g., different, higher) exclusion threshold. For example, in the RMSD-based dataset shown in FIG. 18, structures having an RMSD value above a 74 Å. threshold were discarded. In certain embodiments, complex models to be used training examples can be labeled as native-like or non-native by comparing their NCN/TCN values to a particular NCN/TCN threshold value. As described in further detail herein, in one implementation multiple training datasets were generated in this manner and used to train and test multiple machine learning models for evaluating scaffold-pose scores. For example, as shown in FIG. 18, in one implementation 214,000 example poses (e.g., represented by scaffold-receptor complex models) were used to create training and testing datasets of 170,000 and 44,000 examples, respectively.

ii. Example Machine Learning Model Architecture

Figure 19A:
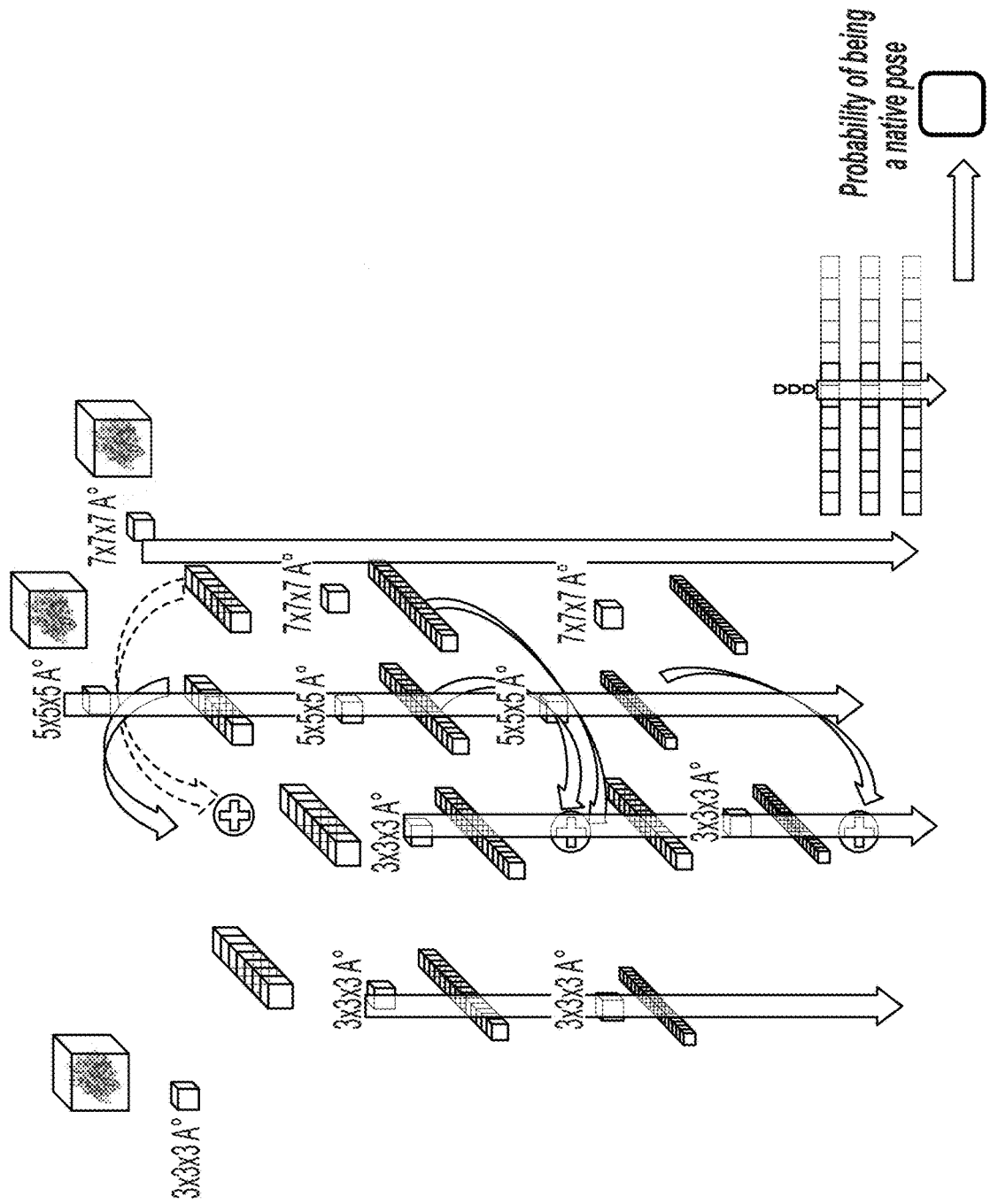
FIG. 19A is a schematic illustrating a spinal cord model (SCM) machine learning architecture, according to an illustrative embodiment.
Figure 19B:
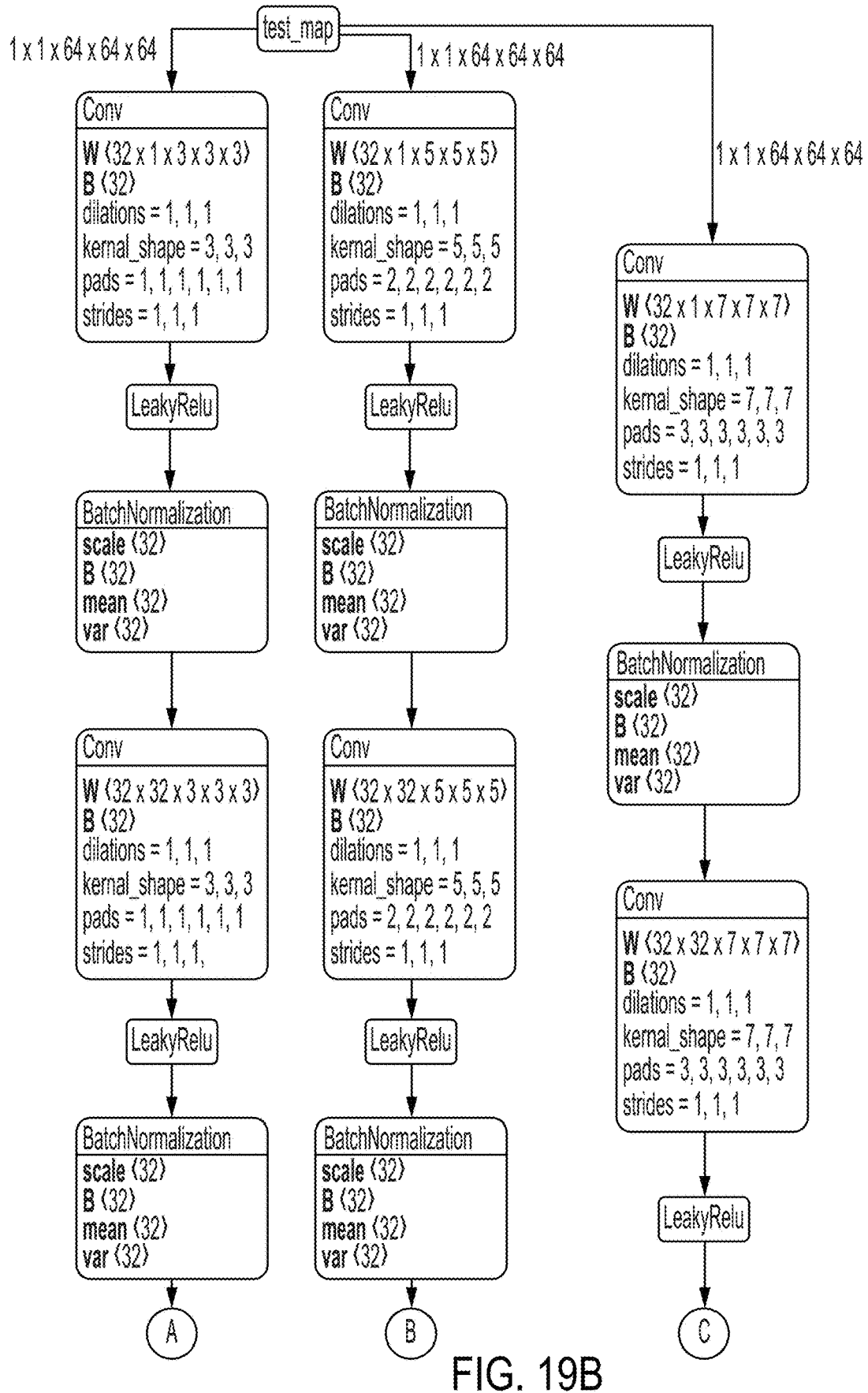
FIG. 19B is portion of a network diagram of an example SCM architecture, according to an illustrative embodiment.
Figure 19C:
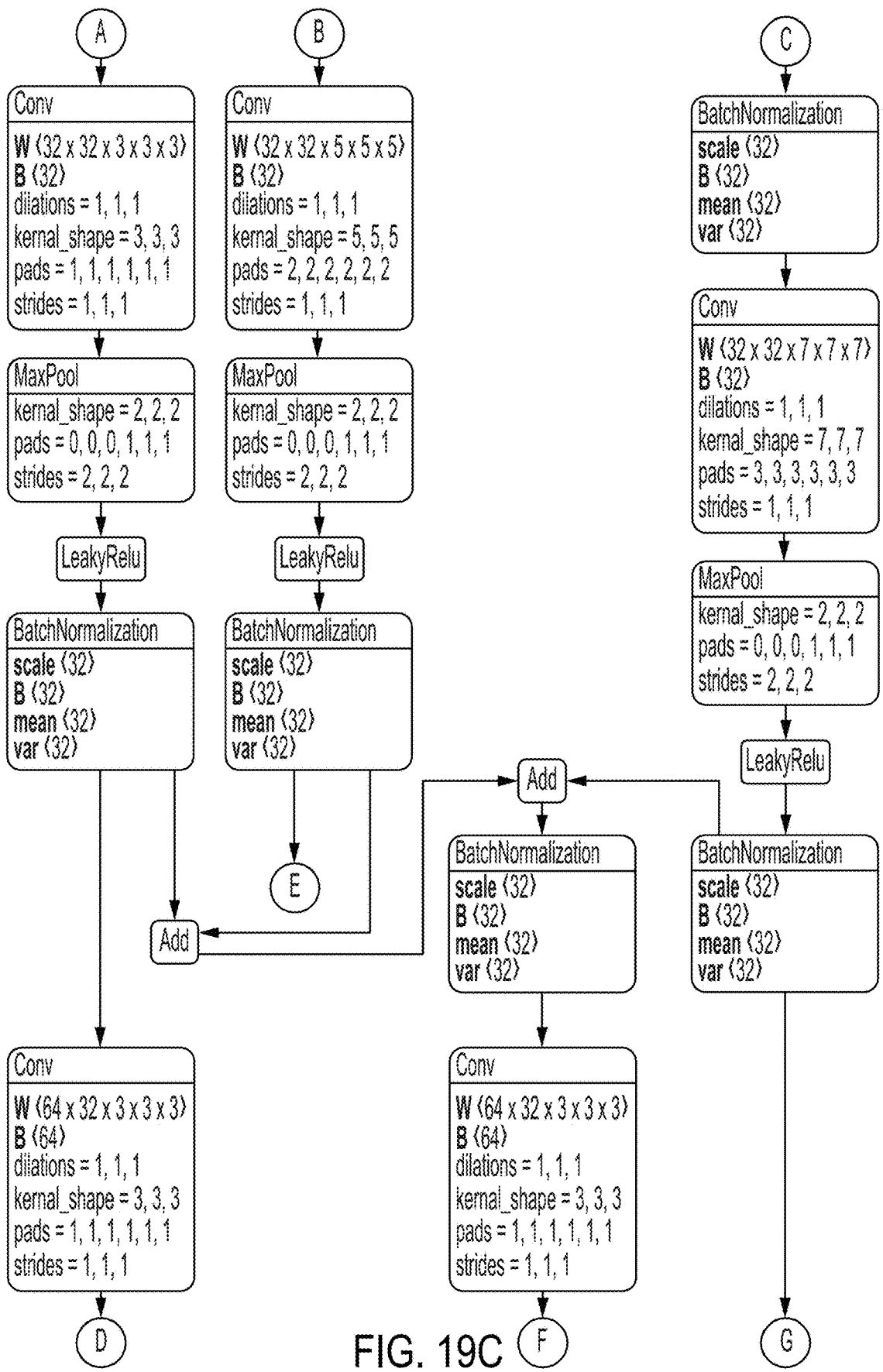
FIG. 19C a portion of the network diagram of the example SCM architecture, according to an illustrative embodiment.
Figure 19D:
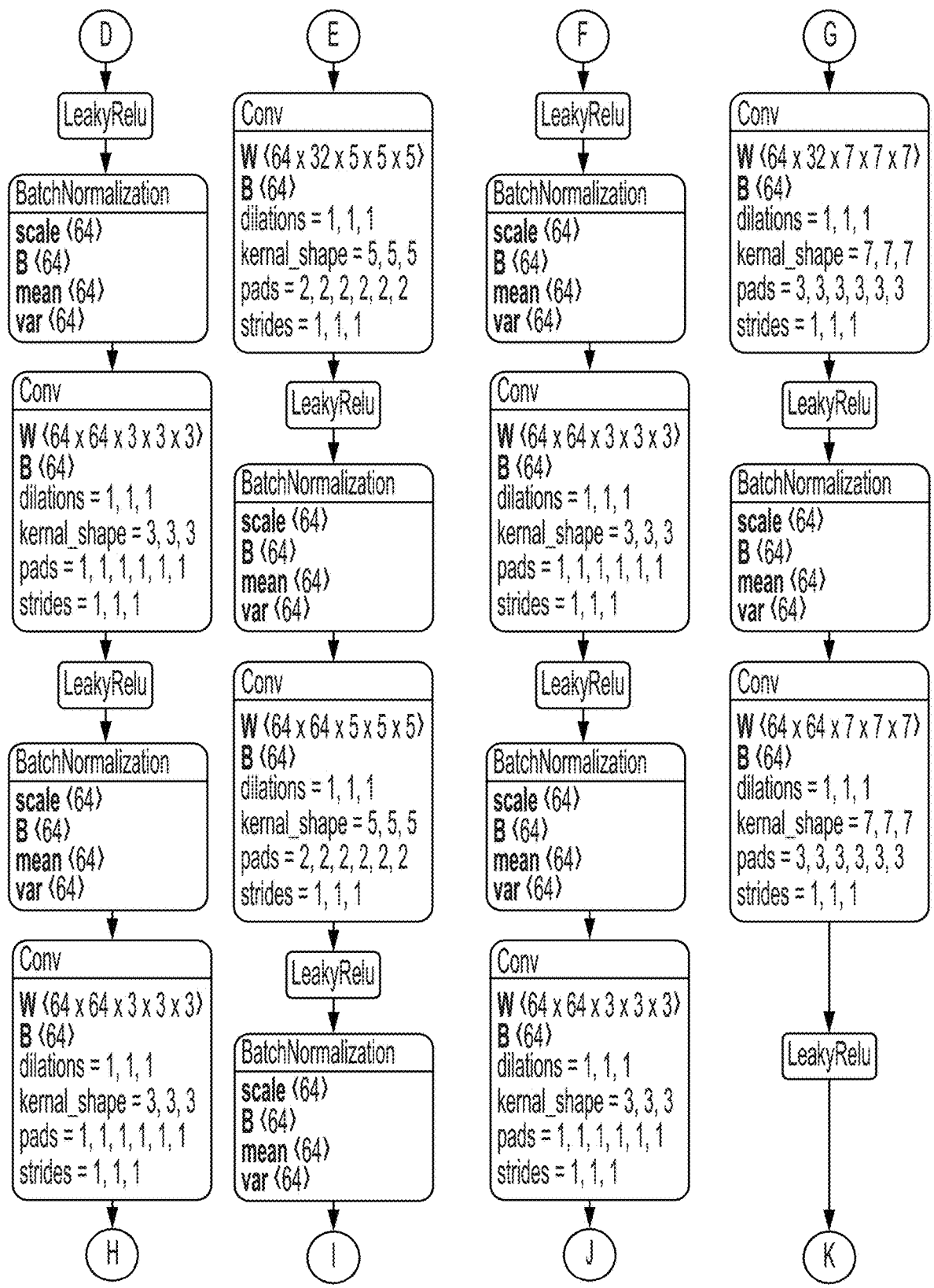
FIG. 19D a portion of the network diagram of the example SCM architecture, according to an illustrative embodiment.
Figure 19E:
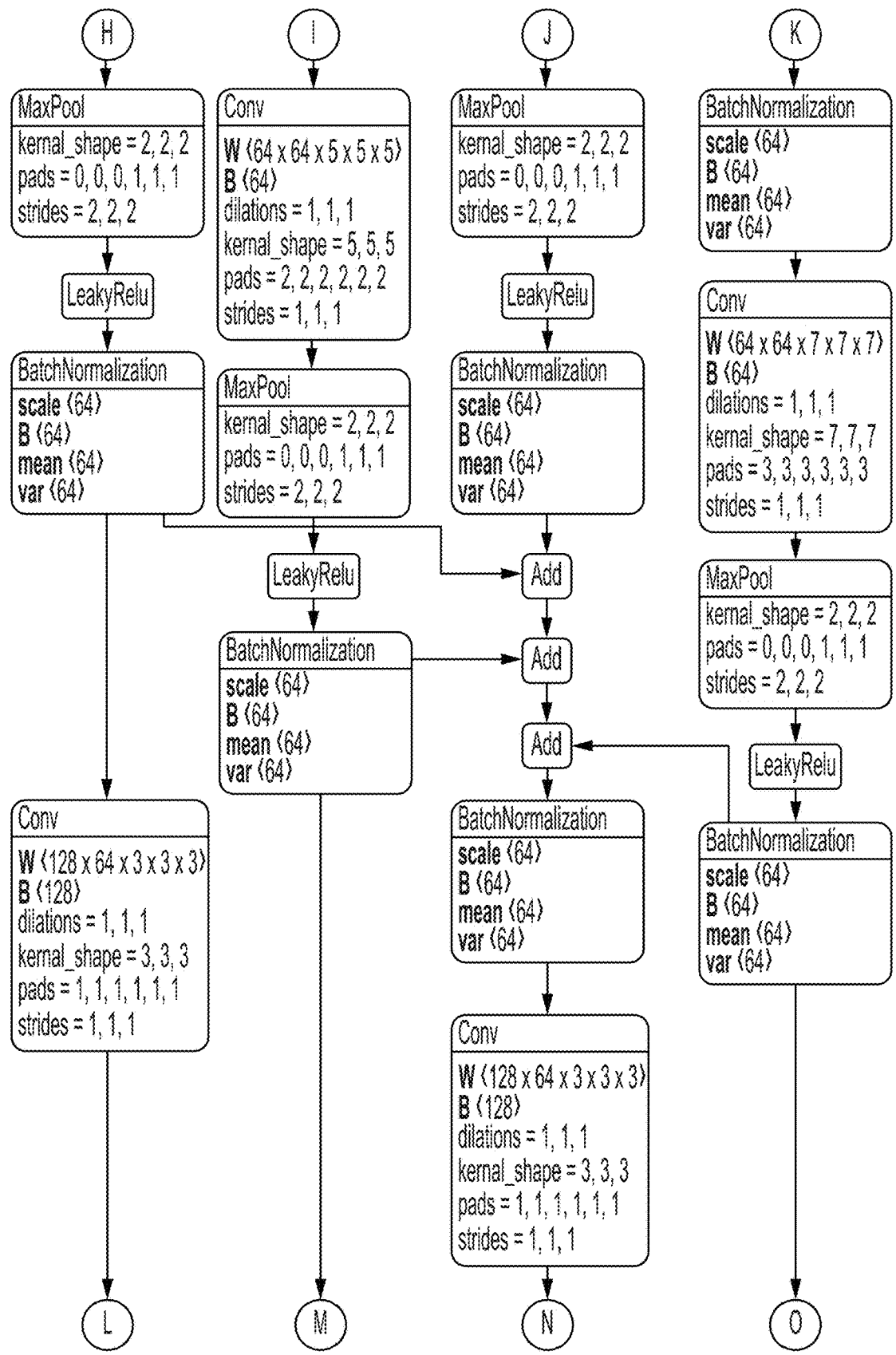
FIG. 19E a portion of the network diagram of the example SCM architecture, according to an illustrative embodiment.
Figure 19F:
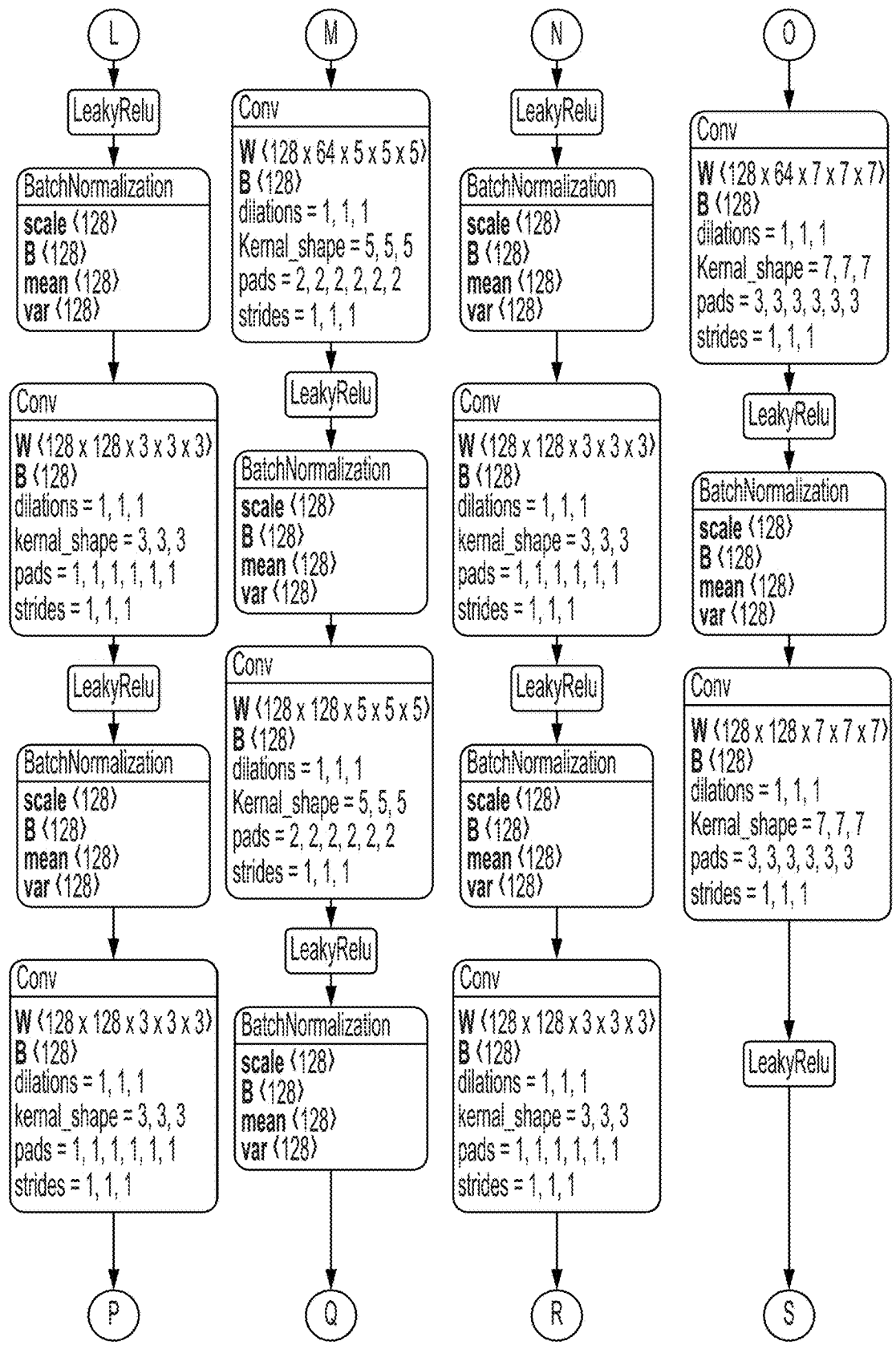
FIG. 19F a portion of the network diagram of the example SCM architecture, according to an illustrative embodiment.
Figure 19G:
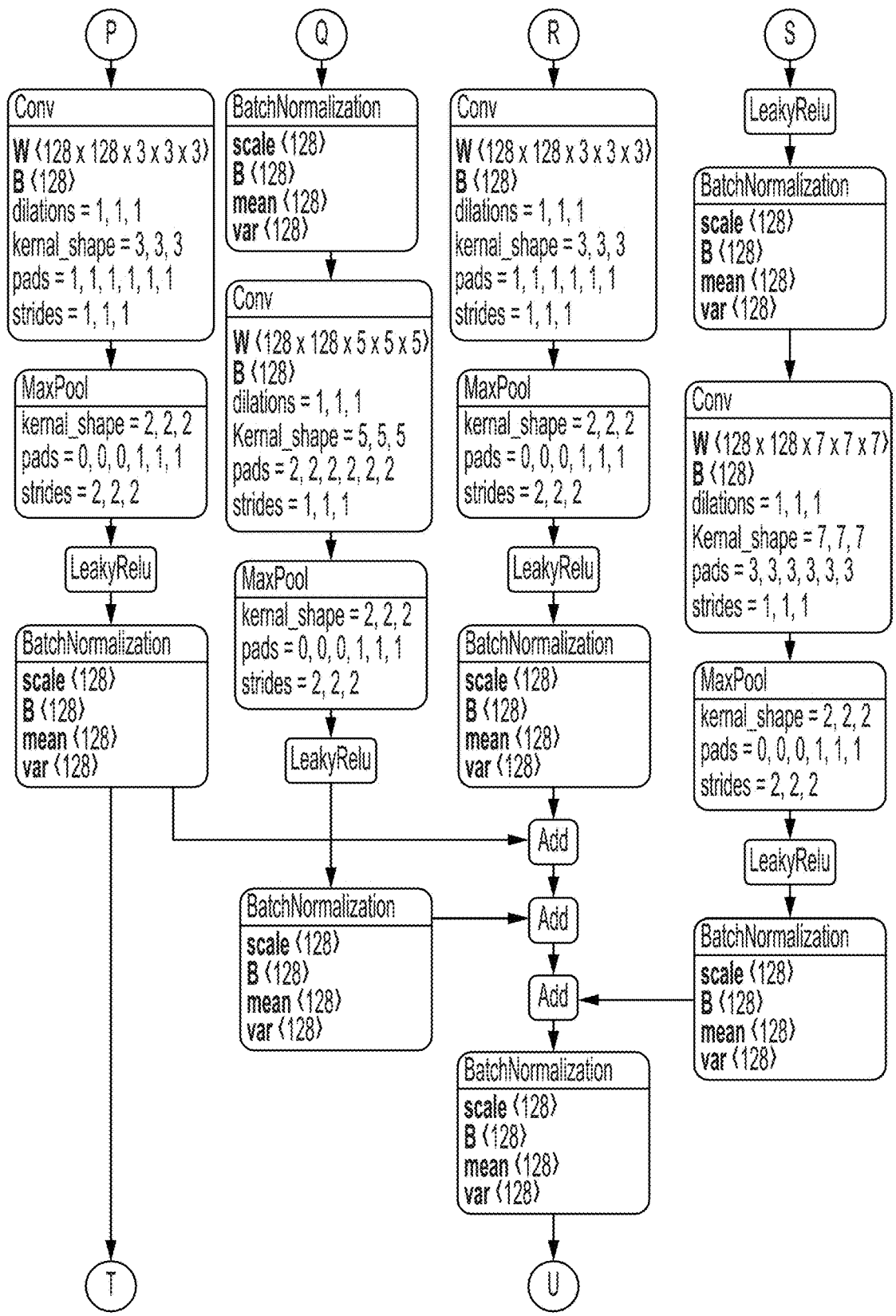
FIG. 19G a portion of the network diagram of the example SCM architecture, according to an illustrative embodiment.
Figure 19H:
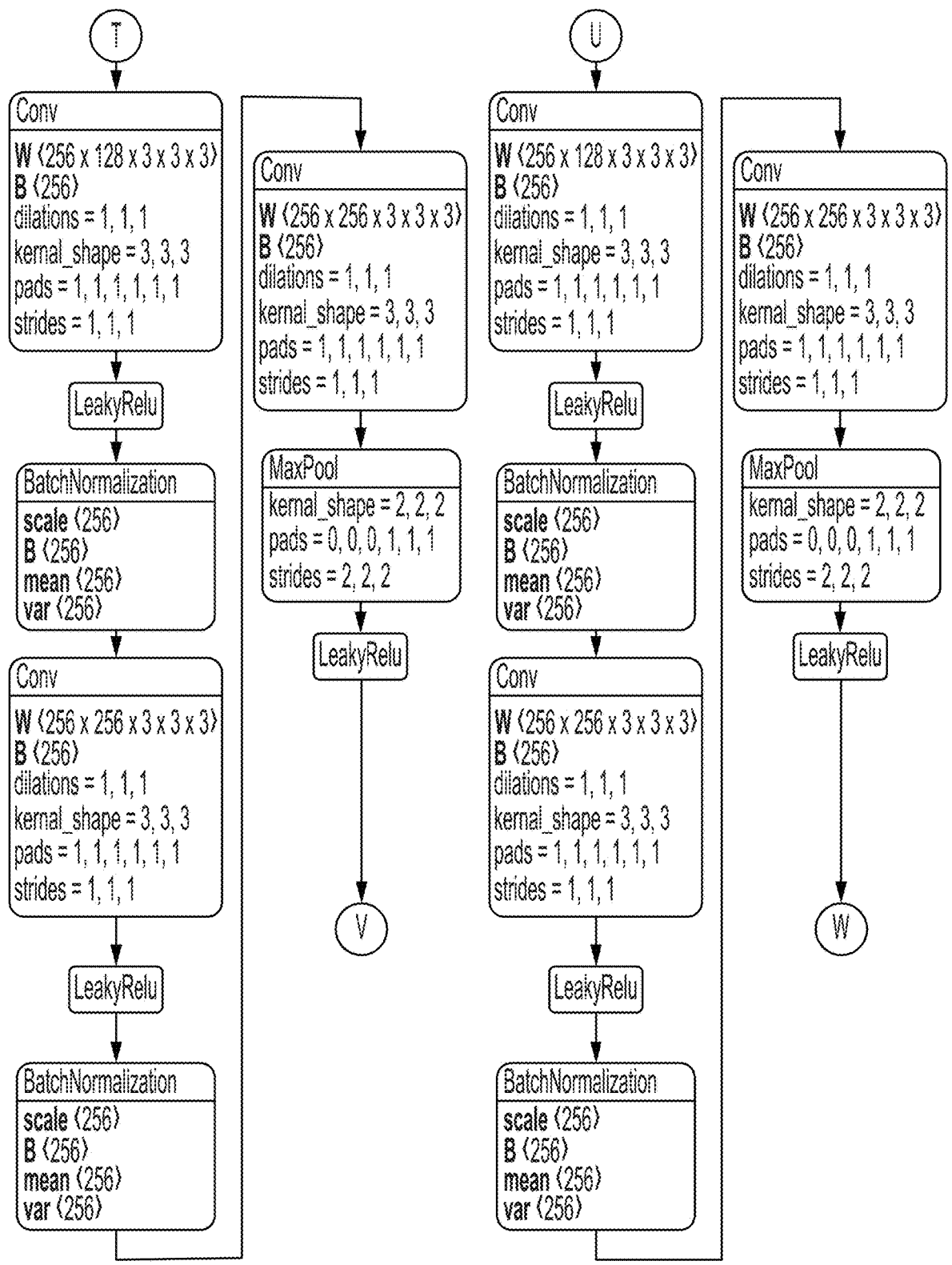
FIG. 19H a portion of the network diagram of the example SCM architecture, according to an illustrative embodiment.
Figure 19I:
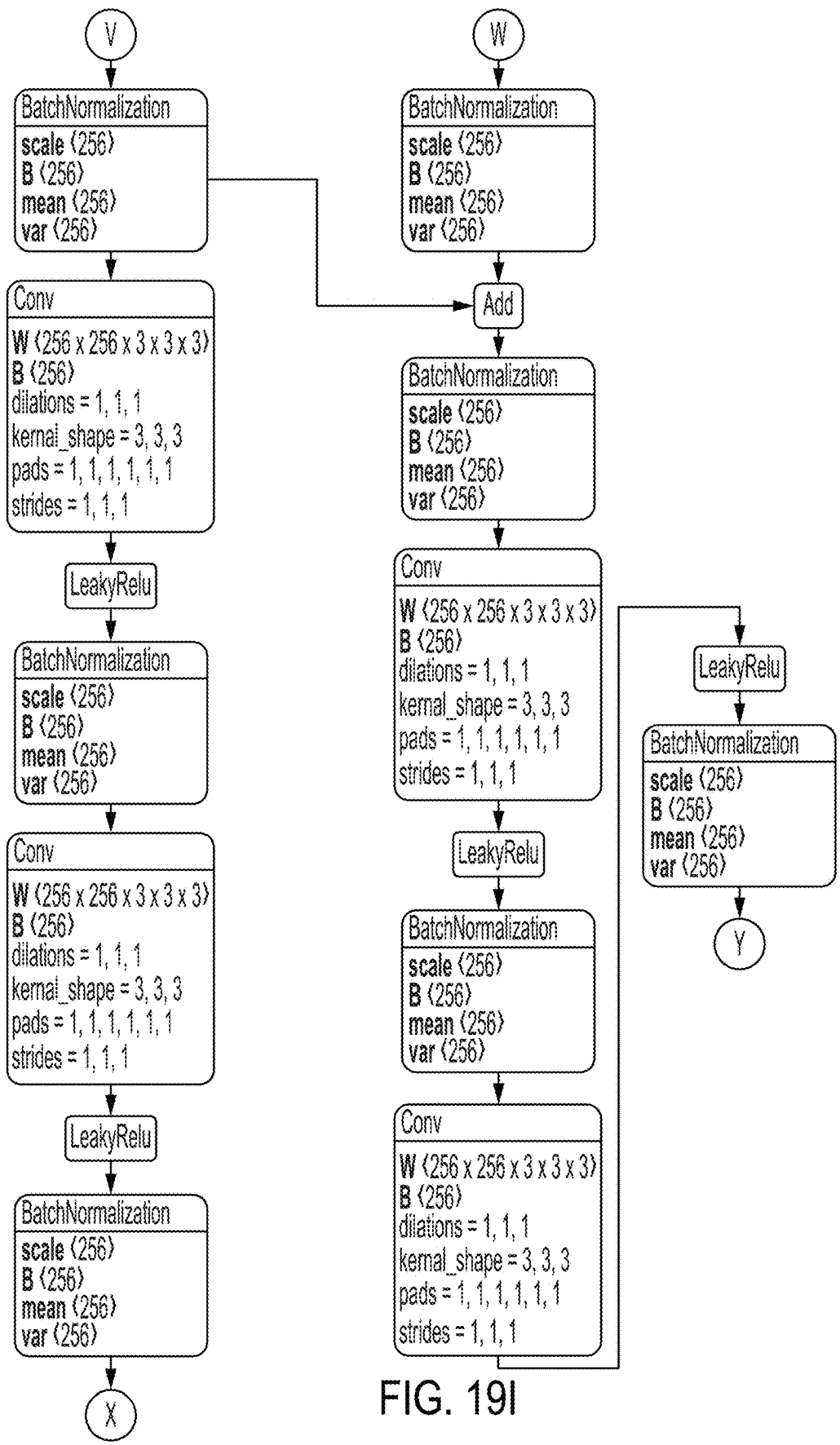
FIG. 19I a portion of the network diagram of the example SCM architecture, according to an illustrative embodiment.
Figure 19J:
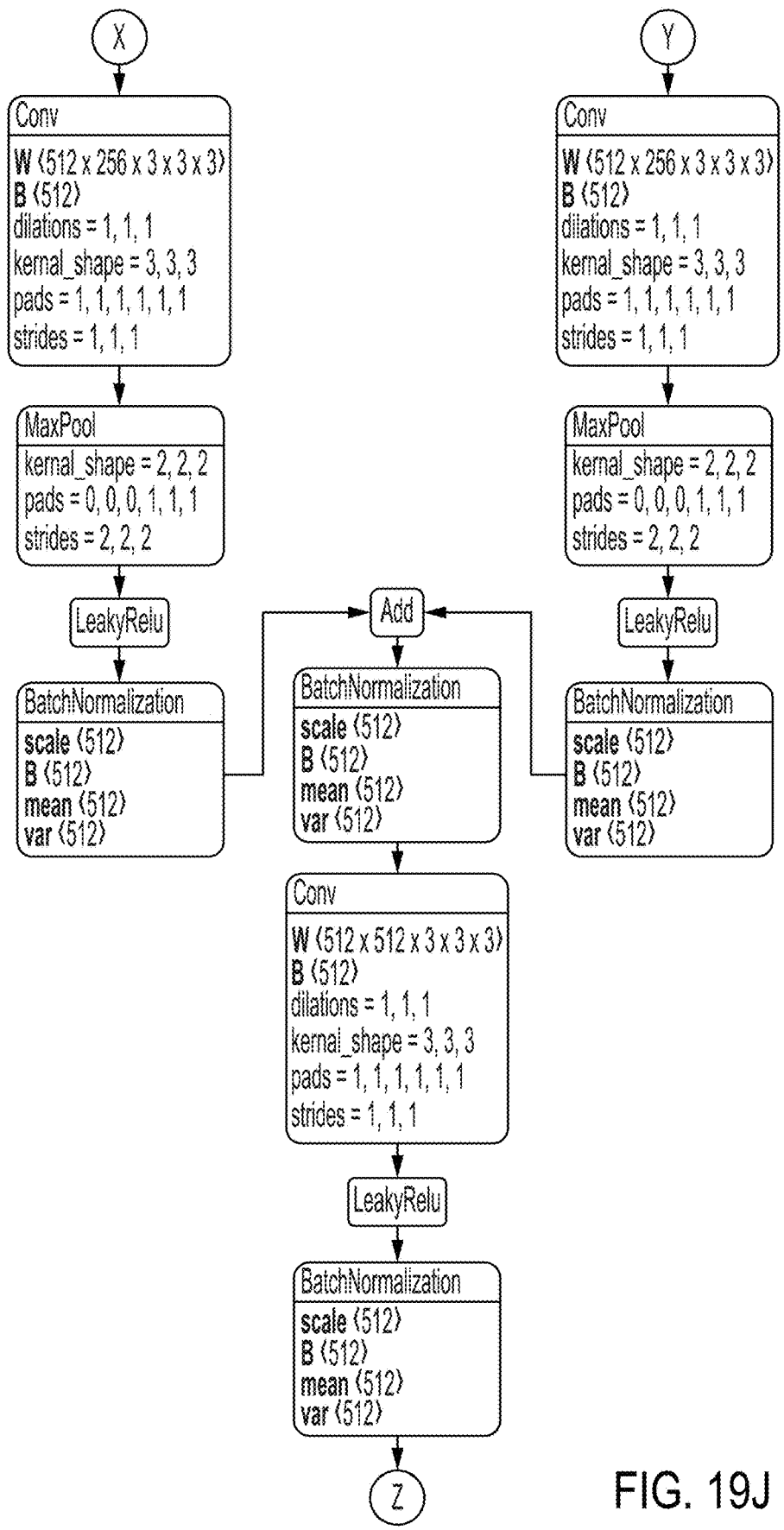
FIG. 19J a portion of the network diagram of the example SCM architecture, according to an illustrative embodiment.
Figure 19K:
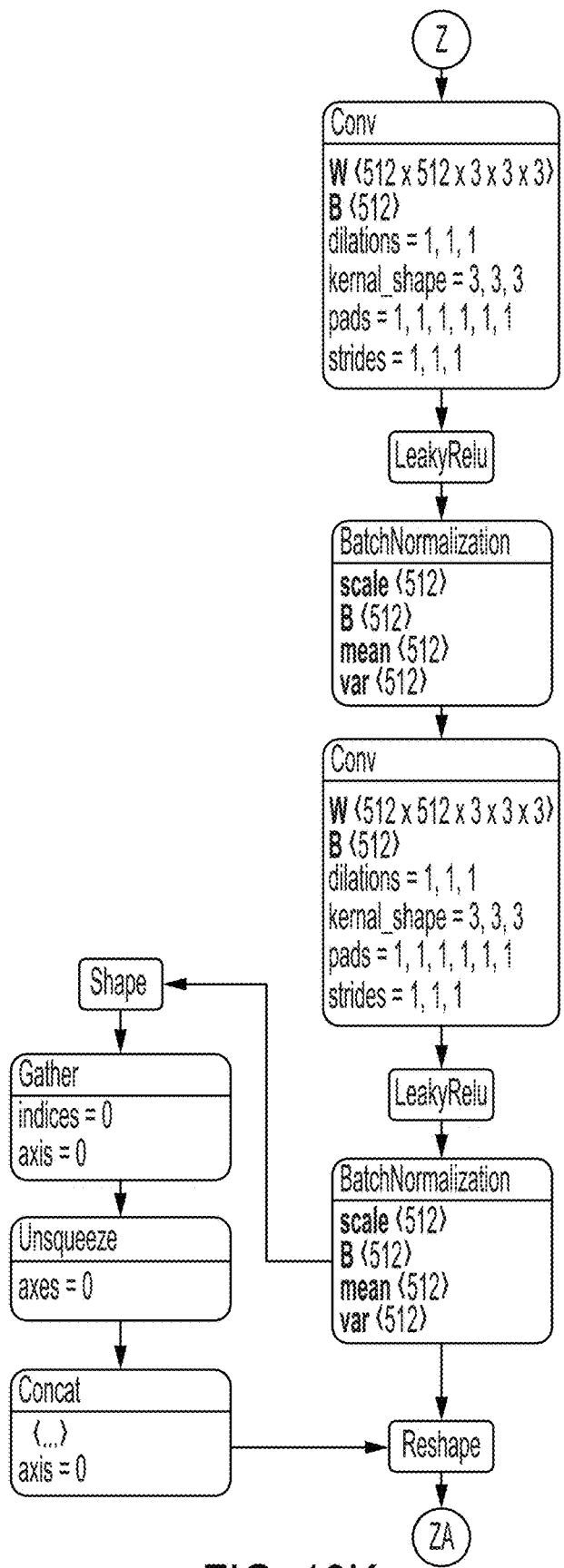
FIG. 19K a portion of the network diagram of the example SCM architecture, according to an illustrative embodiment.
Figure 19L:
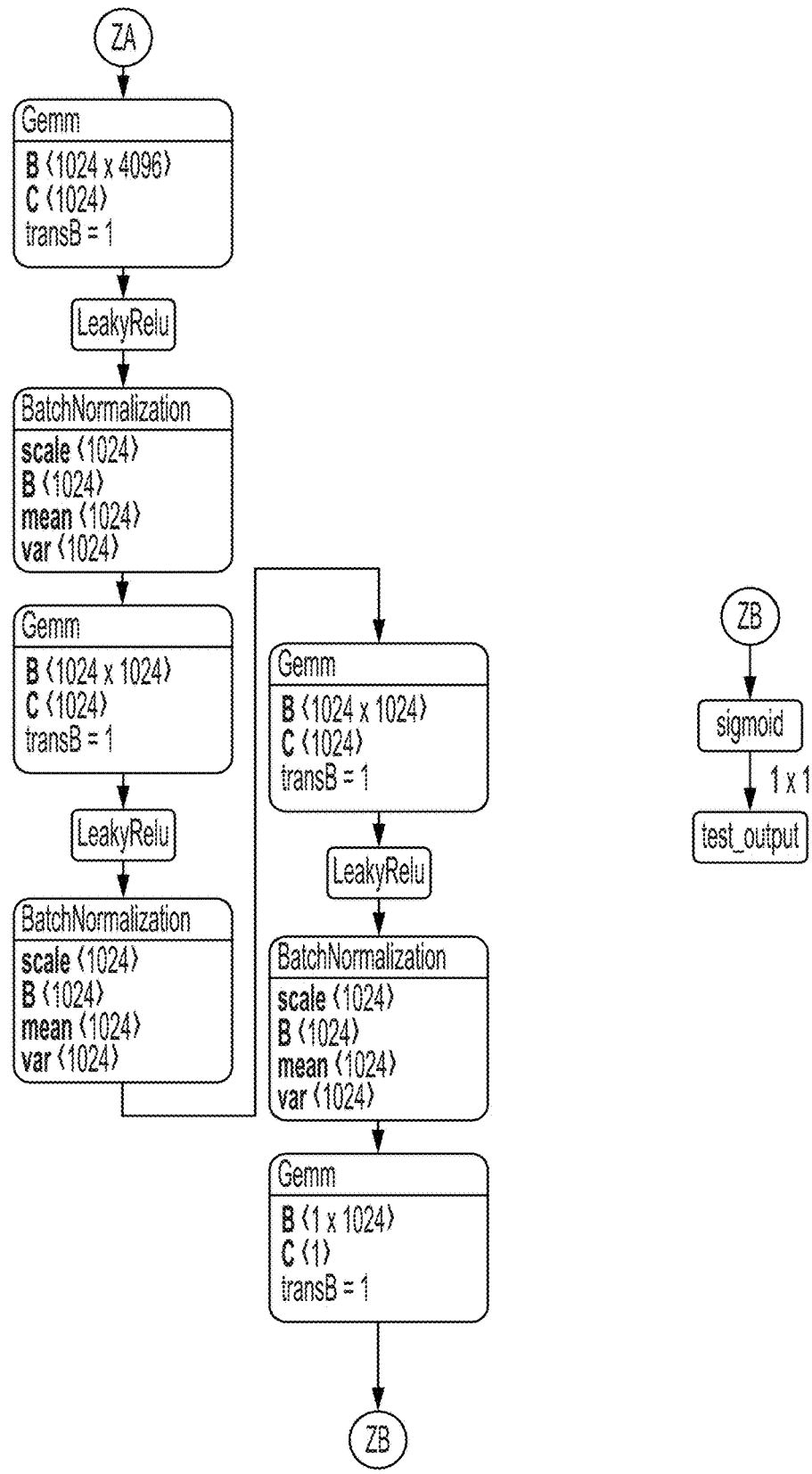
FIG. 19L a portion of the network diagram of the example SCM architecture, according to an illustrative embodiment.

Turning to FIG. 19A, machine learning models of AI-powered modules described herein implement a variety of different architectures, including various artificial neural networks (ANN), convolutional neural networks (CNN), and others. In certain embodiments, a machine learning model utilized herein implements a spinal cord model architecture (SCM, which may be considered a type of CNN). In certain embodiments, a machine learning model used within scaffold docker module to compute scaffold-pose scores as described herein implements a SCM architecture.

FIG. 19A illustrate an example SCM architecture that receives a three-dimensional EDM as input (e.g., a 64×64×64 EDM) and includes three parallel convolutional networks, each of which uses a different kernel size. In particular, in SCM, a first convolutional network utilizes a 3 Å resolution kernel, a second convolutional network utilizes a 5 Å kernel, and a third convolutional network utilizes a 7 Å kernel. In certain embodiments, multiple kernel sizes are utilized in this manner to capture short-, middle- and long-range features of an interface region. SCM may also include a main central network that integrates the respective outputs of the 3 parallel networks at each layer. Without wishing to be bound to any particular theory, this approach may be considered similar to a spinal cord integrating information from peripheral nerves. In certain embodiments, main central network also features 3×3×3 kernels. In certain embodiments, parallel layer level operations performed by the three parallel convolutional network and integration performed by the main central network are treated as a group—e.g., corresponding to single a "vertebra."

In certain embodiments, this "vertebra" grouping is repeated, resulting in multiple integrations from parallel networks. For example, in certain embodiments, a vertebra pattern is repeated up to 6 times, resulting in up to five integrations from parallel networks. The SCM may include any suitable number of iterations including 1, 2, 3, 4, 5, 6, 7, 8, 9, 10, 20, 50, 100, 1000, 10,000, 100,000, 1,000,000, and more than 1,000,000 iterations, as well as other numbers and subranges of iterations therebetween. In certain embodiments, fully connected layers further reduce a shape of output from 1024 to 1 (i.e., a single numerical value). In certain embodiments, this last (output) value represents a probability of the input pose to feature native-like properties. A detailed network architecture diagram of an exemplary SCM in accordance with embodiments described herein is shown in FIGS. 19B-L.

iii. Example Transfer Learning Training Procedure

Figure 20:
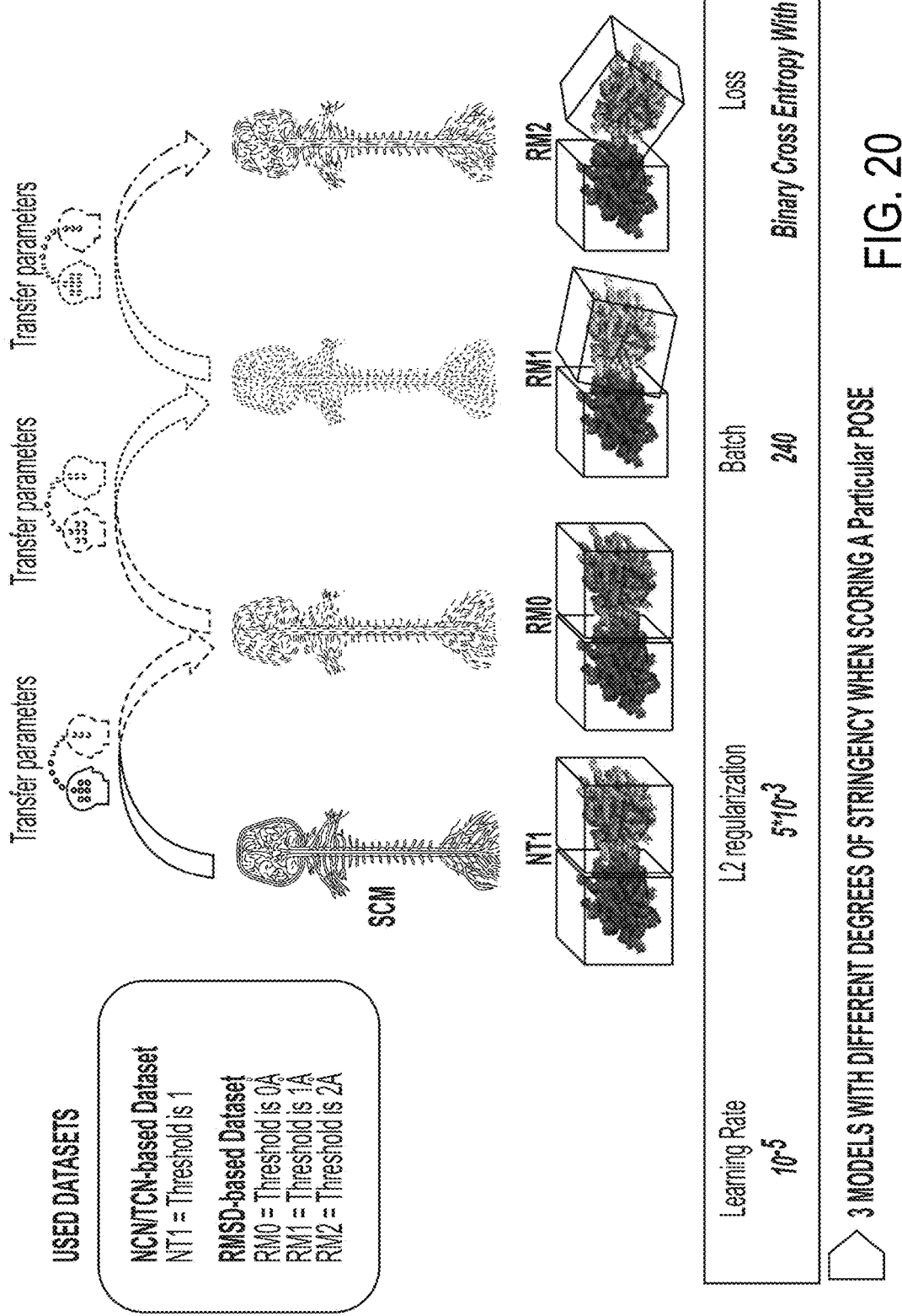
FIG. 20 is a schematic illustrating an example transfer learning approach for training a machine learning model, according to an illustrative embodiment.

Turning to FIG. 20, in certain embodiments multiple (e.g., two or more) machine learning models are trained. For example, as shown in FIG. 20, multiple models may be trained utilizing different training datasets. In certain embodiments, a transfer learning approach is used. For example, FIG. 20 illustrates an example approach that utilizes a four-stage transfer learning approach wherein four models are trained in successive fashion, each using a different training dataset. In the example shown in FIG. 20, each machine learning model shares a common architecture—a SCM—and performs binary classification. In particular, each machine learning model is trained to evaluate an input representation—such as 3D EDM—of a scaffold-target complex model and output a value that represents a probability that the input represents a native complex. In this manner, the machine learning model output can be used as a scaffold pose score that measures a degree of similarity between structural features of the complex represented by the input and those of native or native-like complexes that the machine learning model has been provided as training data.

Accordingly, each training data set used in the example shown in FIG. 20 comprises a plurality of complex models that are assigned to one of two classes—a native-like class and a non-native class. In the four training datasets, values of pose quality metrics computed for each complex are compared to a threshold value in order to sort example complex models into the two classes. A first training data set, "NT1", utilizes the NCN/TCN value and assigns complex models to the native-like class if their NCN/TCN value is one. The second, third, and fourth datasets—"RM0," "RM1," and "RM2," respectively—are created by assigning complex models to the native-like or non-native class according to their computed RMSD values, based on a comparison with a particular threshold value. In a particular RMSD dataset, complex models having a RMSD value below the threshold value are assigned to the native-like class, and those with RMSD values above the RMSD value are assigned to the non-native class. Each dataset uses a different threshold value—RM0 uses a threshold of OA, RM1 uses a threshold of 1 Å, and RM2 uses a threshold of 2 Å. In this manner, training different models using different datasets can be used to create models that impose varying degrees of stringency when scoring a particular input representation.

Figure 21:
FIG. 21 shows three tables presenting results demonstrating performance of three trained machine learning models created in accordance with certain embodiments described herein.
Figure 22A:
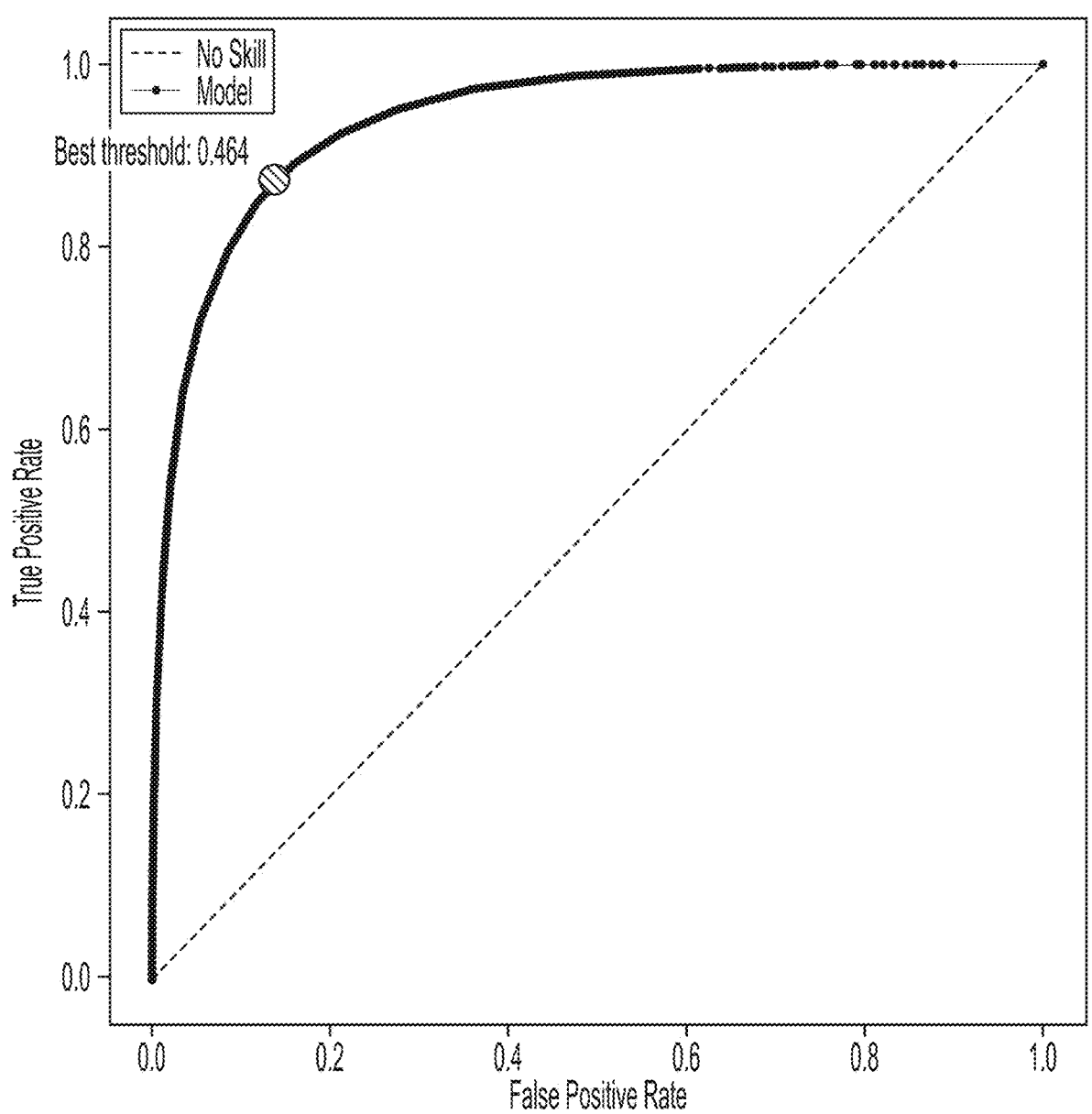
FIG. 22A is a graph showing receiver operating characteristic (ROC) curves for one of the three machine learning models of FIG. 21.
Figure 22B:
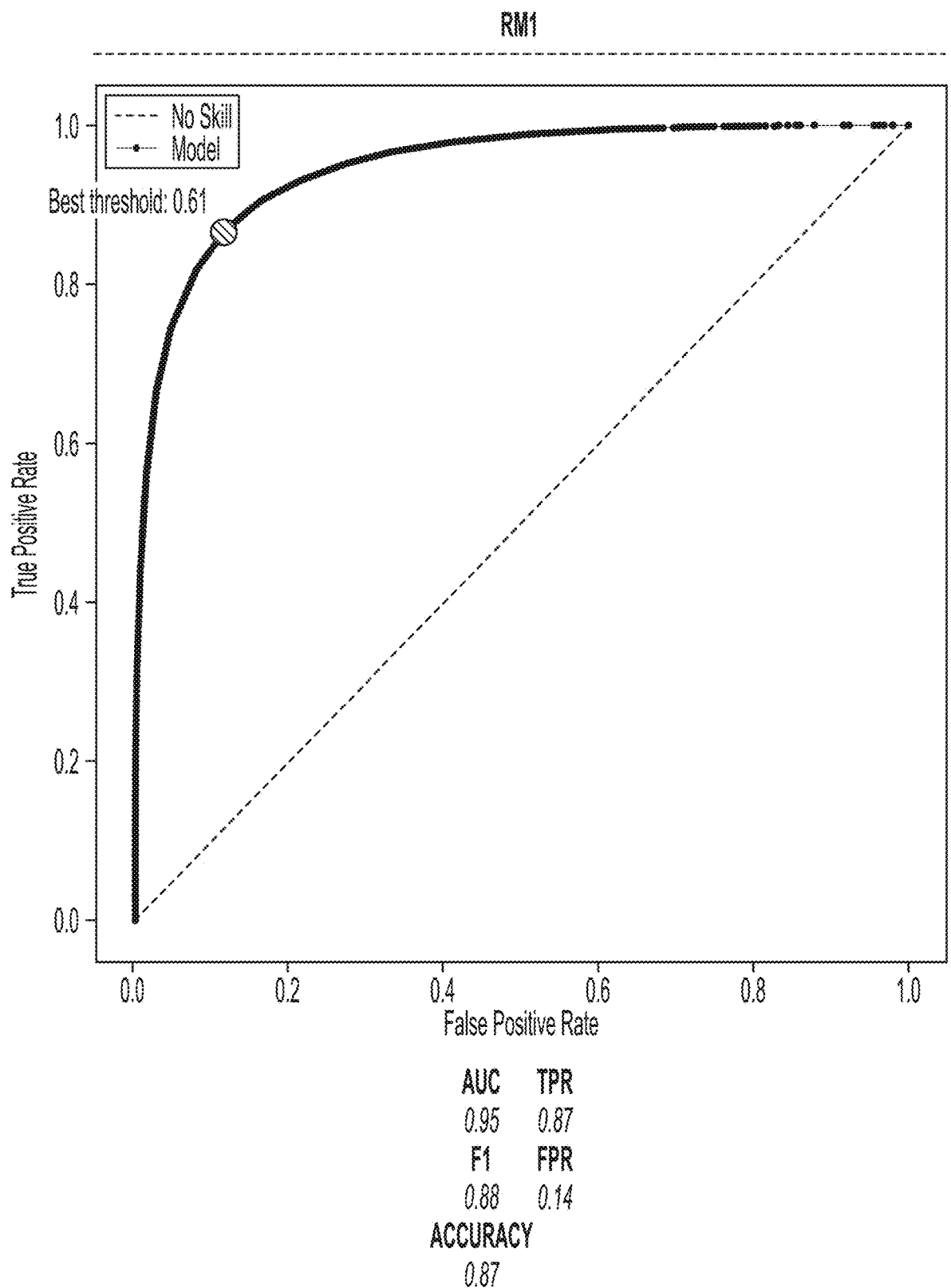
FIG. 22B is a graph showing receiver operating characteristic (ROC) curves for one of the three machine learning models of FIG. 21.
Figure 22C:
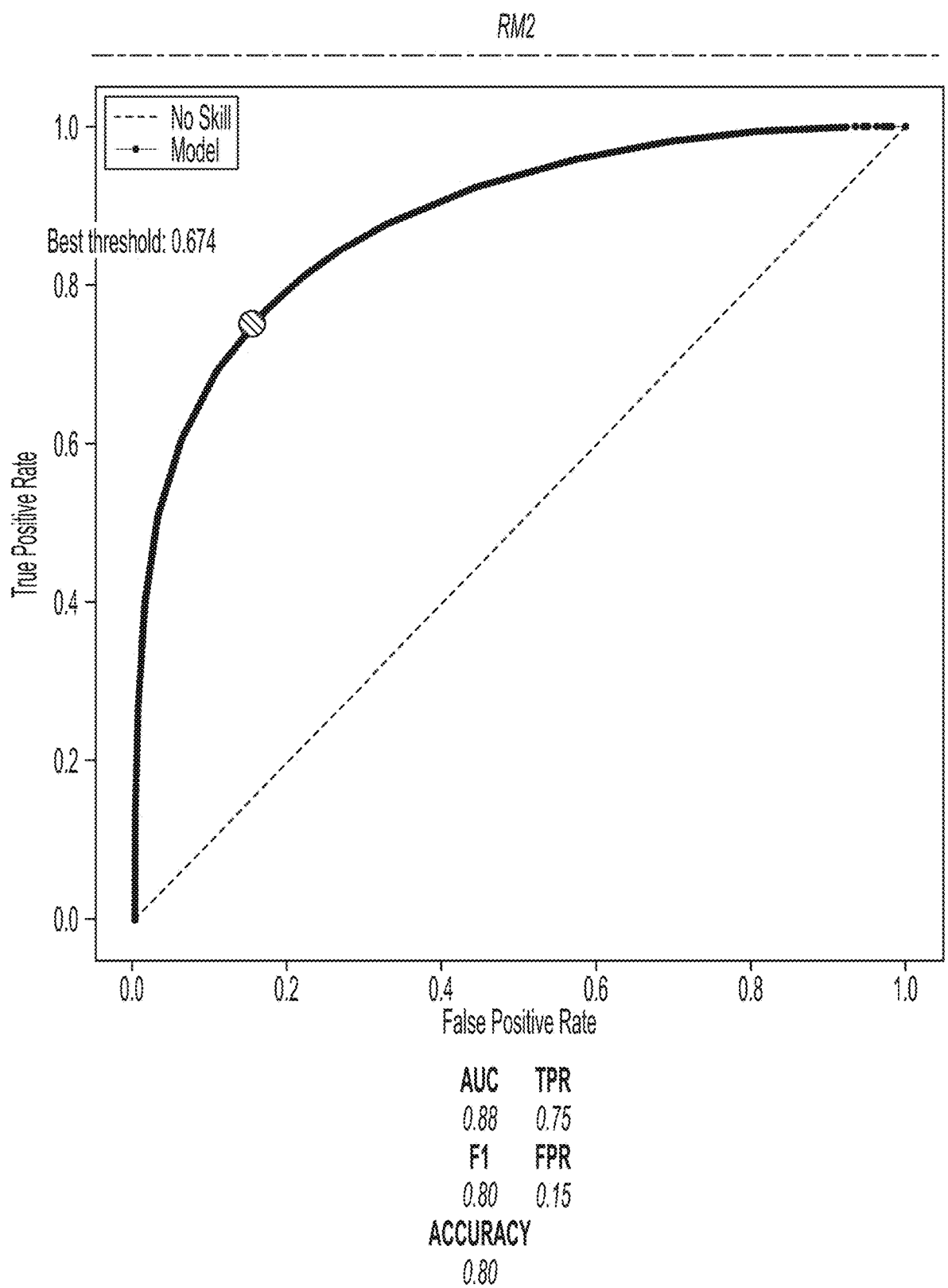
FIG. 22C is a graph showing receiver operating characteristic (ROC) curves for one of the three machine learning models of FIG. 21.

In certain embodiments, training multiple models in this fashion may utilize a transfer learning approach, whereby model parameters (e.g., weights) determined via training one model are used as initial starting points for training another. For example, as shown in FIG. 20, the four models are trained in succession, with more stringent models trained first, and their parameters utilized as starting points for increasingly relaxed models. Once trained, the three RMSD-based models were validated using testing datasets as described herein. Validation results for each of the three RMSD models are shown in FIGS. 21 and 22A-C. FIG. 21 provides tables of performance metrics and FIGS. 22A-C compares ROC curves for each of the three models. As shown in FIG. 21 and FIGS. 22A-C: for the RM0 model, an Area under the Curve (AUC) of 0.94 was obtained, along with a true positive rate (TPR) of 0.87, a false positive rate (FPR) of 0.14, an F1 score of 0.87 and an accuracy of 0.87; for the RM1 model, an AUC of 0.95, TPR of 0.87, FPR of 0.14, F1 score of 0.88, and accuracy of 0.87 were obtained; and for the RM2 model, an AUC of 0.88, TPR of 0.75, FPR of 0.15, F1 score of 0.80 and accuracy of 0.80 were obtained.

iv. Example Scaffold Docking Process

In certain embodiments, trained machine learning models as described herein are utilized in a scaffold docker module in order to evaluate candidate scaffold models and poses thereof for use in designing a custom biologic for binding to a target. As described herein, a scaffold docker module aims to identify favorable peptide backbones (represented by scaffold models) and orientations thereof that can be used as molecular scaffolds and populated with amino acids to design a binding interface.

Figure 23:
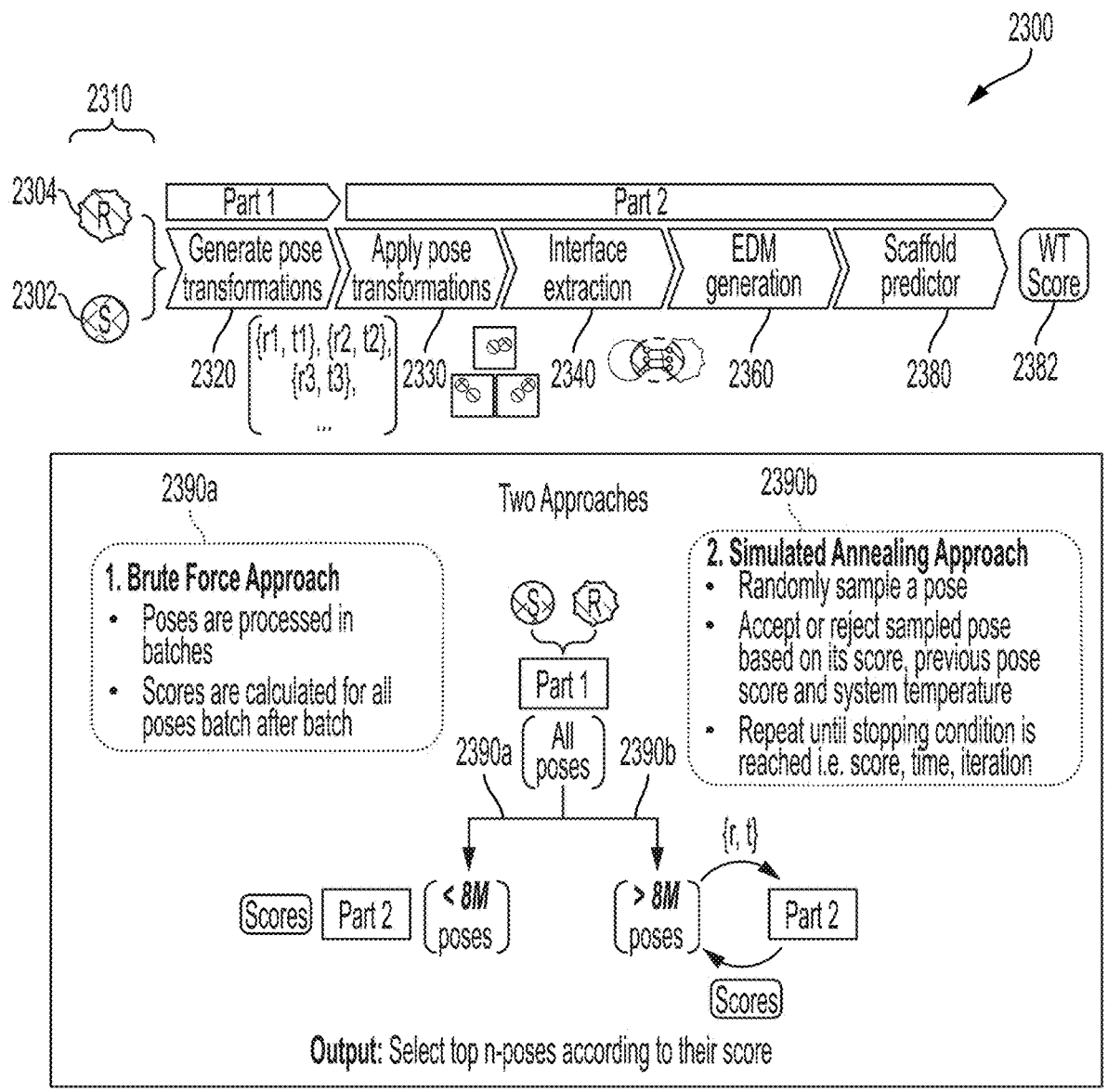
FIG. 23 is a schematic showing an example process for evaluating candidate scaffold model poses, according to an illustrative embodiment.

FIG. 23 illustrates an example process 2300 for identifying favorable candidate scaffold models and poses thereof. In certain embodiments, a candidate scaffold model 2302 representing a particular candidate peptide backbone and a structural model of a target (e.g., a particular receptor; e.g., a target molecule or target complex) 2304 are received as input 2310. Pose transformations are generated 2320 (e.g., via process 1600) and applied 2330 to scaffold model 2302 to orient and position it in different poses with respect to target 2304. In certain embodiments, this approach creates a plurality of candidate scaffold-target complex models, each representing a complex comprising the particular candidate peptide backbone oriented at a particular pose with respect to the target.

In certain embodiments, for example in addition or alternatively to orienting and/or positioning a scaffold model in different poses with respect to a target, generation of scaffold-target complex models may also include adjustments the scaffold model and/or portions thereof. Such adjustments may, for example, be used to account for and/or model backbone flexibility, wherein certain sub-regions of peptide backbones may, naturally, move, flex, etc. in space.

In certain embodiments, scaffold-target complex models generated in this manner are then evaluated and scored by a machine learning model—scaffold predictor model 2380. In particular, in certain embodiments, for each scaffold-target complex model, an interface extraction step (e.g., as described herein, with respect to FIGS. 5 and 6) is performed 2340 to identify an interface sub-region of the scaffold-target complex model comprising a portion of the scaffold and target that are in proximity to each other. In certain embodiments, a three-dimensional EDM is generated 2360 based on the identified interface sub-region and provided as input to scaffold predictor model 2380. Based on the received EDM, scaffold predictor model 2380 determines a scaffold-pose score 2382 for the particular scaffold-target complex model. In certain embodiments, as described herein, scaffold predictor model is trained to perform a binary classification and, accordingly, outputs, as the scaffold-pose score, a likelihood value representing a probability that the EDM representation of the scaffold-target complex model represents a native complex. In this manner, although the input scaffold-target complex is artificially generated, the scaffold-pose score determined by the scaffold predictor model provides a quantitative assessment of a degree to which the input scaffold-target complex model and, accordingly, the particular candidate peptide backbone and pose it represents, exhibits its properties and/or has key structural features resembling those of native, physically viable structures. For example, a scaffold-pose score may range from zero to one (e.g., representing a probability) with values closer to one indicative of more favorable scaffold models and poses thereof.

Accordingly, the scaffold docker may use its machine learning model to evaluate and score a plurality of scaffold-target complex models and use the determined scaffold-pose scores to select a subset of scaffold-target complex models that represent favorable poses of a particular candidate peptide backbone.

Without wishing to be bound to any particular theory, while, in certain embodiments, a scaffold model of a scaffold-target complex model does not represent detailed amino acid structure of a candidate peptide backbone, the representation of the target may be a full representation of a protein and/or peptide and, accordingly, include representations of amino acid side chains. Accordingly, the machine learning based approach utilized herein may account for, not only a geometrical relation between a target and various backbones and poses thereof, but also complex physiochemical behavior due to a detailed amino acid structure and atoms of the target. Leveraging deep learning to train machine learning models of the scaffold docker module as described herein, scaffold-pose scores computed and used to evaluate candidate backbones and poses thereof may thus reflect and be based on detailed geometric and physiochemical features 'learned' (e.g., via the training process) by the machine learning models.

In certain embodiments, poses and scaffold-target complex models are generated in batches, and then scored 2390a. In certain embodiments, poses and scaffold-target complex models are generated and scored in an interactive fashion 2390b, whereby a pose is generated, used to create a scaffold-target complex model that is then scored, and the determined score used as feedback for generation of a new pose which is evaluated in a subsequent iteration. In certain embodiments, this iterative approach utilizes optimization algorithms, such as simulated annealing, with the scaffold predictor model acting as an objective function whose output is maximized.

Computationally, in certain embodiments, a scaffold docker module in accordance with the present disclosure can evaluate about 1 million poses in about 36 hours using a graphics processing unit (GPU), in particular, as tested using a GPU x1: NVIDIA TITAN RTX, 24 GB and CPU core x10: Intel® Xeon® CPU E5-2609 v4 @ 1.70 GHz. In certain embodiments, a particular sampling and/or optimization approach, such as a brute force approach, simulated annealing approach, etc., may be selected based on a number of poses to be evaluated (e.g., determined poses, e.g., based on various approaches described herein). For example, in certain embodiments, a brute force approach may be used when a number of poses to be evaluated is below (e.g., or equal to) a particular pose threshold value and another, such as a simulated annealing, approach used when a number of poses to be evaluated is greater than (e.g., or equal to) the particular pose threshold value. Selection of a particular sampling/optimization approach may be performed automatically, e.g., based on a comparison with a particular pose threshold value. One or more pose threshold values may be used to select between various (e.g., two or more) sampling and/or optimization techniques. Pose threshold values used in this manner may be determined and/or set based on various criteria, such as computer hardware properties, desired execution times, etc. and/or via a user interaction (e.g., as a user-defined parameter). For example, in the example approach shown in FIG. 23, a brute force approach 2390a was used when a number of poses to be evaluated is about 8 million or less, and when a number of poses to be evaluated exceeded 8 million, an optimization approach 2390b such as simulated annealing, was used, in order to decrease a number of cases. In some embodiments, other computational and/or hardware configurations that make use of application-specific integrated circuits (ASIC), multiple GPUs, one or more tensor processing units (TPU), and/or other scheme that employ parallelization may be used.

In certain embodiments, scaffold docking approaches described herein utilize one or more clustering methods to reduce a number of poses, for example (i) for evaluation and scoring by a machine learning model and/or thereafter—pre-scoring clustering, and/or (ii) for evaluation and/or further processing in design of a custom biologic—post-scoring clustering. In certain embodiments, this is achieved by clustering/grouping the poses based on an RMSD distance metric and selecting only centroids of various clusters as representative poses (e.g., selecting, for each cluster, a centroid of the cluster as representative of all poses in the particular cluster). In certain embodiments, by reducing an initial set of poses to a smaller subset of representative cluster centroid poses, the number of poses used in a scaffold docker module pipeline as described herein can be significantly reduced. This reduction offers benefits in terms of computational time for downstream processing steps, and, additionally or alternatively, facilitates analysis for users.

Pre-scoring clustering: In certain embodiments, pre-scoring clustering is performed, wherein poses are clustered after a pose generation step (e.g., such as cross-correlation, and/or other steps such as, but not limited to, steps of process 1600 described herein), but before they have been scored (e.g., by a machine learning model). This approach reduces a number of poses that are evaluated and scored by a machine learning model and may provide significant benefit in computational time as this step may be one of the slowest steps of the process, e.g., especially a number of poses to test is on the order of millions. Additionally or alternatively, native-like, and hence high scoring poses, are likely to be located in a same neighboring space and, accordingly, once one of these poses is identified in that space, others are not necessarily required (e.g., for example, for a binding site region on a receptor, most poses in that proximity are likely to be more native like).

Post-scoring clustering: In certain embodiments, post-scoring clustering is performed, wherein poses are clustered after they have been scored, e.g., by a machine learning model as described herein. In certain embodiments, this approach reduces a number of poses provided, for example as output of a scaffold docker module as described herein. Where such poses are reviewed and/or otherwise evaluated/ analysed by a human operator, this provides a more manageable number of poses for the human operator to analyse. Additionally or alternatively, wherein favourable poses are provided to downstream modules in a pipeline, such as an interface designer module and/or binding affinity predictor module as described herein, this approach provides a reduced set of poses for downstream processing. As described herein, in this approach takes advantage of a likelihood that native-like poses tend to be concentrated in certain spatial regions.

Various methods for clustering may be implemented to perform pre-scoring clustering and/or post-scoring clustering as described herein.

E. Interface Designer Module

Figure 24:
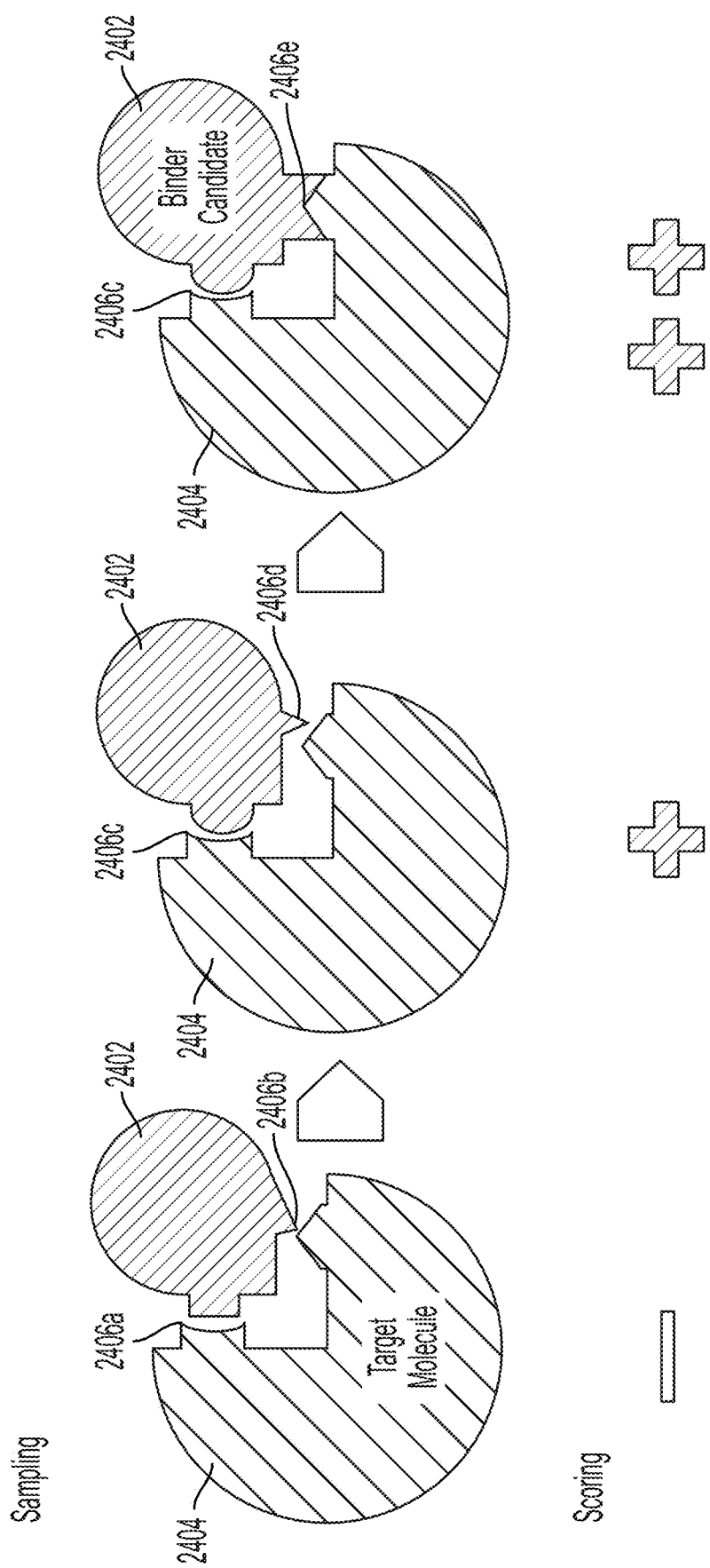
FIG. 24 is a schematic illustrating an example interface design approach, according to an illustrative embodiment.

FIG. 24 is a schematic illustration of an approach to interface design, which, in certain embodiments, may be performed by an interface designer module as described herein. In particular, in certain embodiments, interface design begins with a candidate peptide backbone oriented in a particular pose with respect to a target and aims to design a binding interface for interacting with the target. In particular, in certain embodiments, a candidate peptide backbone serves as a molecular scaffold which can be populated with amino acid side chains to create a binding interface. As illustrated in FIG. 24, a structural model representing a candidate peptide backbone 2402 in a favorable pose may be populated with varying types and orientations (e.g., rotamers) of amino acid side chains (e.g., 2406a,b,c,d,e) along a region in proximity to the target 2404. Amino acids may be varied, and resulting complex models scored to design a favorable interface.

Figure 25:
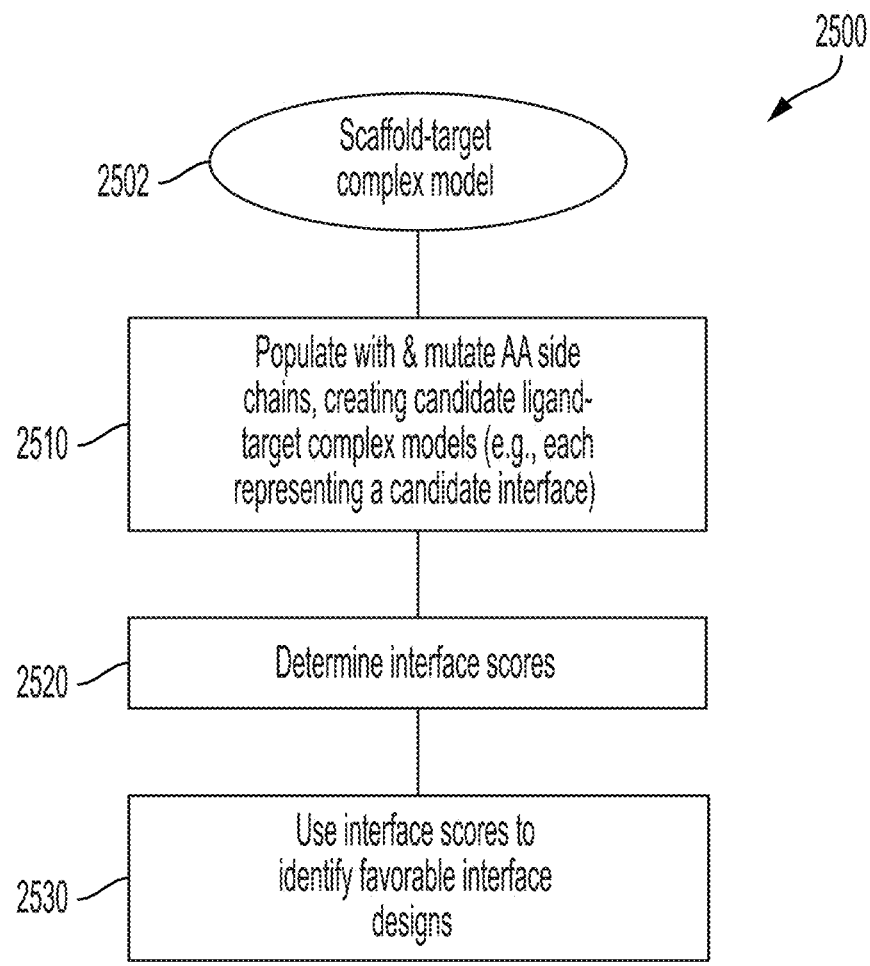
FIG. 25 is a block flow diagram of an example process for creating and evaluating candidate interface designs, according to an illustrative embodiment.

FIG. 25 shows an example process 2500 for designing candidate interfaces, described in further detail herein.

i. Training Data Set Construction

In certain embodiments, an interface designer module utilizes a machine learning model to determine an interface score that quantifies a level of similarity between a representation of a prospective interface received as input and a native interface. In certain embodiments, an interface score is a numerical value that represents a predicted number of mutations between a prospective interface and a native interface, as determined by the machine learning model. In certain embodiments, in order to train a machine learning model to generate interface scores in this manner, systems and methods described herein utilize a training dataset construction approach that uses (i) examples of native interfaces obtained from structural data of native complexes and (ii) artificially generated mutant interfaces.

Figure 26:
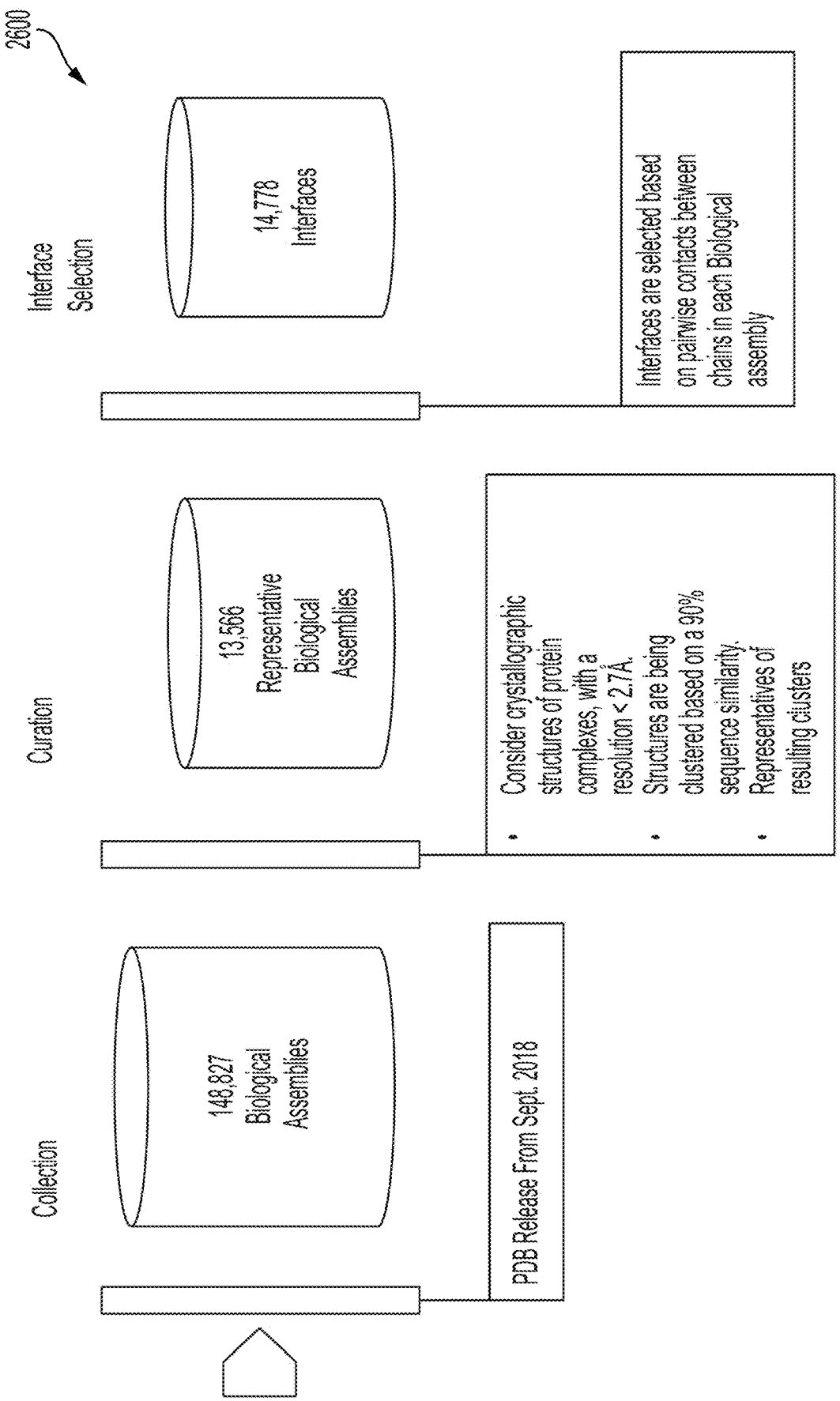
FIG. 26 is a schematic illustrating an approach for obtaining and curating an initial dataset for training a machine learning model to evaluate prospective interface designs, according to an illustrative embodiment.

Turning to FIG. 26, for example, in certain embodiments, native interface models may be obtained and/or created by obtaining structural models of various ligand-receptor complexes (e.g., biological assemblies) from one or more databases. These may include, without limitation, public databases such as PDB, as well as other database sources, such as proprietary databases. For example, as shown in FIG. 26, the September 2018 PDB release provides access to structural models of over one hundred and forty thousand native biological assemblies. In certain embodiments, a subset of the available structural models are filtered and selected based on various selection criteria in a data curation step to produce a curated dataset. For example, in certain embodiments, a minimum resolution criteria is imposed. In certain embodiments, additionally or alternatively, clustering analysis may be used to select a subset of structural models based on sequence similarity.

For example, FIG. 26 shows an illustrative implementation whereby a data curation step imposed a minimum resolution requirement to select a subset of crystallographic structures of protein complexes with a resolution of <2.7 Å (i.e., 2.7 Angstroms) and performed clustering analysis to group structures based on sequence similarity. Representative structures of resulting clusters were selected. This approach resulted in selection of a subset of 13,566 particular structural models from the 148,827 available in the PDB database. In various embodiments and implementations, other resolution thresholds such as from about 0.1 Å to about 10 Å, or from about 0.2 Å to about 8 Å, or from about 0.3 Å to about 7 Å, or from about 0.4 Å to about 6 Å, or from about 0.5 Å to about 5 Å, or from about 1.0 Å to about 4 Å, or from about 2 Å to about 3.5 Å, or from about 2.5 Å to about 3 Å may be used as minimum crystallographic resolutions.

In certain embodiments, an interface extraction step is performed on each structural model of the curated dataset to obtain a plurality of interface models, each a representing a portion of a complex comprising a ligand and a receptor, said portion an interface sub-region about an interface between the ligand and receptor. In certain embodiments, a particular structural model may yield more than one extracted interface. For example, the example implementation shown in FIG. 26 resulted in 14,778 interfaces.

Approaches described above with respect to FIG. 26, e.g., for interface extraction and/or data curation may also be used in connection with steps and processes for creating training data for other approaches described herein, for example with respect to creation of training data for interface designer module and/or binding affinity predictor module, described in further detail herein.

Figure 27:
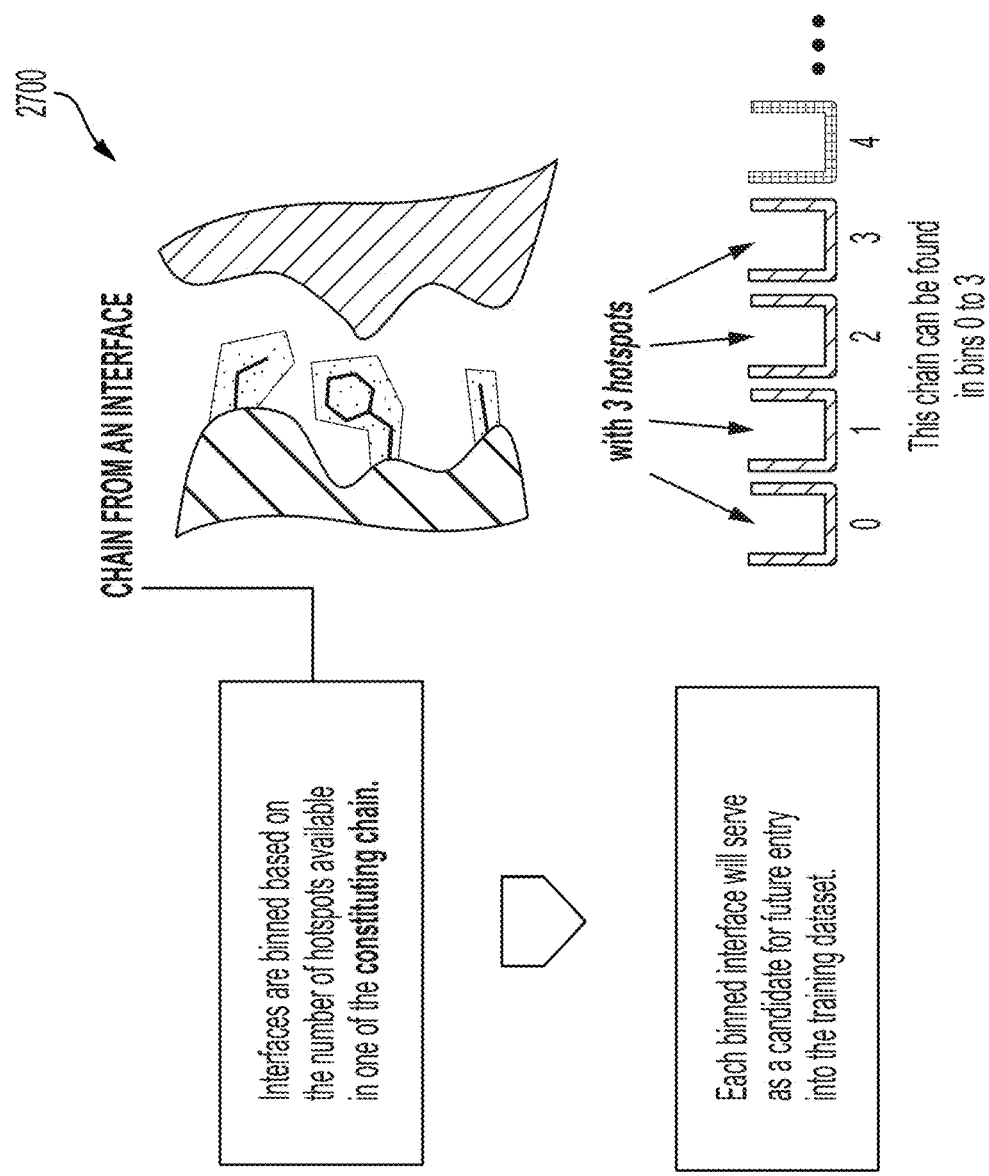
FIG. 27 is a schematic illustrating an approach for creation of a training dataset for training a machine learning model to evaluate prospective interface designs, according to an illustrative embodiment.

Turning to FIG. 27, in certain embodiments, interface models may be binned according to a number of identified hotspots. For example, in certain embodiments, each interface model is analyzed to identify hotspots available on a particular constituting chain. An interface model is then assigned to one or more bins according to a number of identified hotspots on a particular constituting chain—e.g., a ligand-side or receptor-side of the interface model.

In certain embodiments, each interface model includes two constituting chains, and hotspots are identified on each constituting chain, such that two sets of hotspots are identified (e.g., treating one chain as the ligand and the other as the receptor, and then switching). In certain embodiments, a particular constituting chain to use for identifying hotspots for purposes of assignment to one or more bins is selected randomly. In one example process, an interface model was randomly assigned as a putative candidate to a specific class/bin based on a number of hotspots found on each chain. This assignment is made with the prerequisite that for a particular chain, a number of hotspots could not be smaller than the bin label—for example, if one chain of a particular interface model was identified as having 6 hotspots it would not be placed in a bin associated with class 9 (e.g., chains with 9 hotspots), but if the other chain was identified as having 9 or more hotspots, it would be. In the specific case where an interface has both chains assigned to the same bin, the generation procedure after picking the interface once as a candidate will prioritize the random selection of other interfaces and will only select the second chain if needed.

Figure 28:
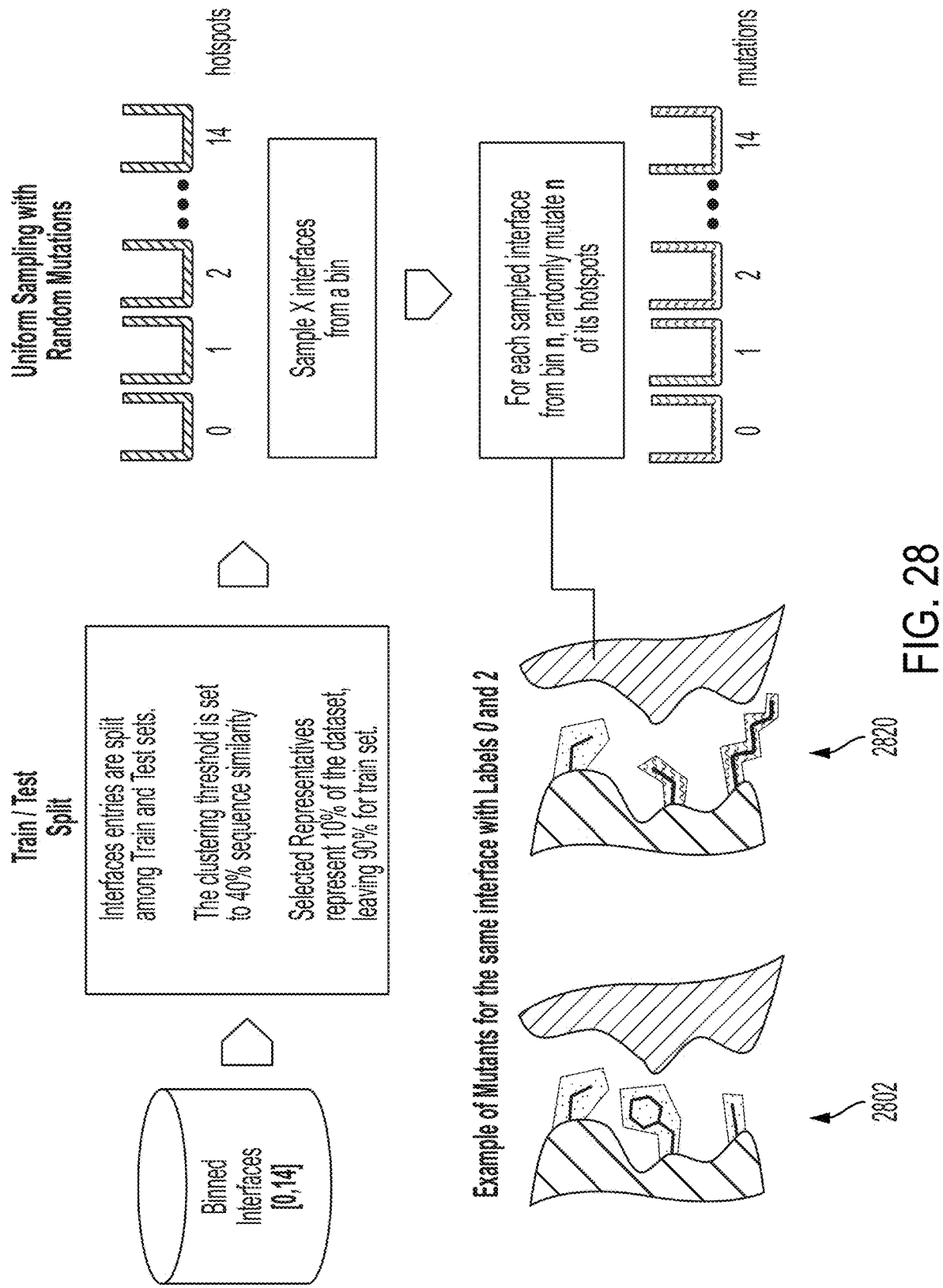
FIG. 28 is a schematic illustrating an approach for creation of a training dataset for training a machine learning model to evaluate prospective interface designs, according to an illustrative embodiment.

Turning to FIG. 28, in certain embodiments, artificial mutant interfaces may be generated from native interfaces by mutating (i.e., varying) amino acids in one or more hotspot locations on a particular chain. In certain embodiments, mutant interfaces are generated to create examples of mutant interfaces having a number of mutations spanning particular (e.g., predefined) range. For example, as shown in FIG. 28, mutant interface 2820 is generated from native interface 2802 by mutating amino acid side chains in two hotspots (shown in red along mutant interface 2802) and retaining an amino acid side chain in a third hotspot. In certain embodiments, a uniform sampling and binning approach such as the approach shown in FIG. 28 is used.

Turning to FIG. 29, in certain embodiments, mutating an amino acid may comprise varying a particular type and/or rotamer of an amino acid side chain in a hotspot. In particular, FIG. 29 illustrates an approach to the random mutation procedure illustrated in FIG. 28. In certain embodiments, random mutation procedure may generally include AA (amino acid) type sampling followed by rotamer sampling. AA type sampling may include randomly selecting a natural amino acid from a given hotspot. In certain embodiments, amino acid types are sampled according to their naturally occurring frequencies (e.g., as opposed to from a uniform distribution), for example via a frequency table as shown in FIG. 29. In certain embodiments, a frequency table such as that shown in FIG. 29 accounts for a particular type of secondary structure (e.g., providing for different frequencies based on a particular secondary structure motif associated with the interface). In certain embodiments, once a particular amino acid type is selected for a particular hotspot site, allowed rotamers for the particular amino acid type and hotspot site are computed based on a library of rotamer probabilities (e.g., torsion angles and probabilities thereof for particular amino acid types), for example such as a Dunbrack Rotamer Library. In certain embodiments, rotamers that induce clashes with the rest of the molecule are excluded. In certain embodiments, for each combination of amino acid type and phi/psi backbone torsion angles, the Dunbrack library yields probabilities of rotamers that have been derived from (for example) existing PDB structures.

Example Training Dataset

Figure 30:
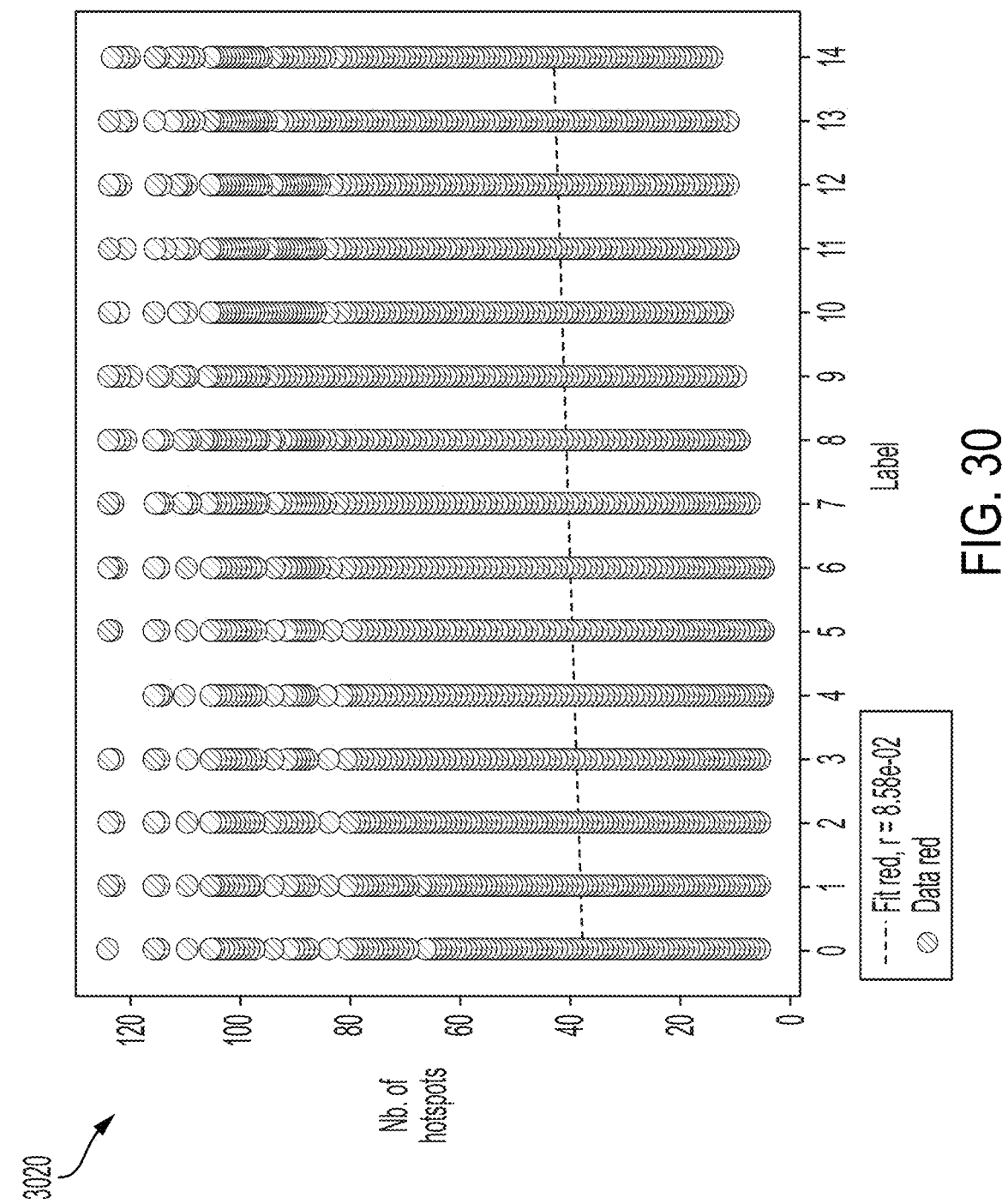
FIG. 30 is a schematic illustrating certain features of a dataset comprising examples of interfaces created in accordance with various embodiments described herein.

FIG. 30 illustrates results of an example training dataset constructed via approaches described herein, for example with respect to FIGS. 26 through 29. In particular, the example training dataset described in FIG. 30 was constructed by identifying hotspots on 14,778 curated native interfaces and assigning each of the native interfaces to one or more of 15 bins labeled 0 to 14 according to a number of identified hotspots. In particular, in accordance with the hotspot binning approaches described with respect to FIGS. 27 and 28, an interface with n identified hotspots on a constituting chain was assigned each of bins labeled zero to n. As shown in FIG. 28, for each interface in a particular bin, mutant versions of the interface were generated by randomly mutating n hotspots of the interface. In this manner, interfaces in bin 0 provided examples of un-mutated, native interfaces (i.e., 0 mutations), interfaces in bin 1 had a single mutation, interfaces in bin 2 had two mutations, and so on, through bin 14. Each interface in each bin was used to generate 10 mutant interfaces to create a final dataset which was split into (i) a training set comprising 3.6 million examples and (ii) a testing dataset comprising 382,000 examples to validate a machine learning model once trained. Graph 3020 of FIG. 30 plots a distribution of training examples according to their label—i.e., with points representing examples located according to a number of mutations and hotspots. The uniform distribution of interfaces across all 15 bins limits possible correlations between the number of hotspots and the labels, thereby preventing biasing of the model during training.

In order to train a machine learning model, each interface example had interface extraction performed and was used to generate a 3D EDM representation for input to the machine learning model.

ii. Example Machine Learning Model Architecture

In certain embodiments, interface designer modules as described herein utilize an interface scoring machine learning model to determine an interface score that quantifies a measure of similarity between a representation of a candidate interface and a native-like interface. In certain embodiments, an interface scoring machine learning model implements a regression model architecture. In certain embodiments the interface scoring model determines, as an interface score, a predicted number of mutations. In certain embodiments, an interface scoring machine learning model implements a classifier architecture, such as a multi-class (e.g., non-binary, having greater than two classes). In certain embodiments, a classifier architecture computes one or more classifier probabilities (e.g., likelihoods of belonging to a particular class) which can, in turn, be used to generate a continuous score, e.g., by computing an expected value using the classifier probabilities and a class label value.

As an illustrative example, two classes representing two intervals e.g. class 0, representing a number of mutations in an interval [0, 4] and class 1, representing a number of mutation interval [4, 8] can be used to create a continuous score as follows by associated each class with a representative value, based on the interval it represents. For example, a mean value of the interval can be used, such that class 0 can be associated with to a mean value for its interval, i.e. 2, and class 1 can be likewise associated with a mean value of 6. Other values/manners of converting an interval to a representative value, e.g., use of a median, mode, etc., may be used. An expectation value for a model prediction can then be determined based on the probabilities predicted for each class and their representative values (e.g., as the sum of the probability-weighted representative values). For example, if a machine learning model predicts a probability of 0.2 and 0.8 respectively for the two classes, one can then compute a score corresponding to an expected value as follows: score=2×0.2+6×0.8=5.2. Other approaches for generating a continuous score from a classifier may be used, additionally or alternatively. For example, one approach is to pre-calculate a regression between the predicted and true labels using the test dataset. The pre-calculated regression function can then be used compute a continuous score. In another approach, a distribution over the different classes may be predicted and then used to derive a mean value.

Figure 31A:
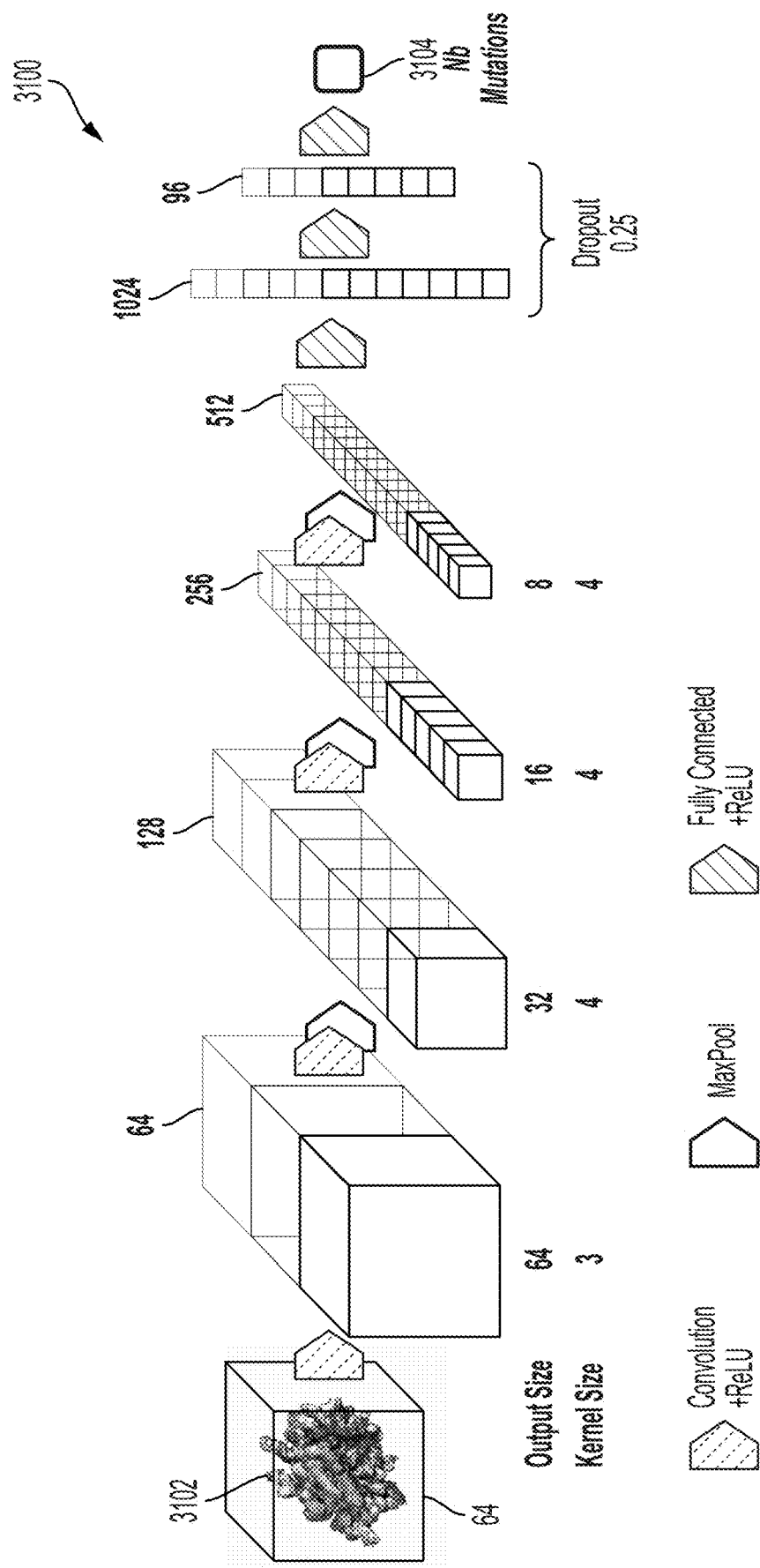
FIG. 31A is a schematic of an example architecture of a machine learning model for evaluating candidate interface designs, according to an illustrative embodiment.

FIG. 31A shows an example regression model architecture that may be implemented via an interface scoring model to compute interface scores as described herein. Example regression model 3100 takes a three-dimensional EDM representation of an interface region of an unknown ligand-target complex model as input and outputs a value representing a predicted number of mutations (e.g., an integer value). The particular implementation shown in FIG. 31 receives an input EDM 3102 having a size of 64×64×64 Å$^3$ (i.e., cubic Angstroms) with a 1 Å (one Angstrom) grid spacing, though various embodiments and implementations may utilize other input sizes and resolution. Regression model 3100 includes multiple convolution layers that progressively collapse output size before passing through a series of fully connected layers to produce the final output value 3104. In certain embodiments, FIG. 31B shows a detailed network diagram of example architecture 3100.

Figure 32A:
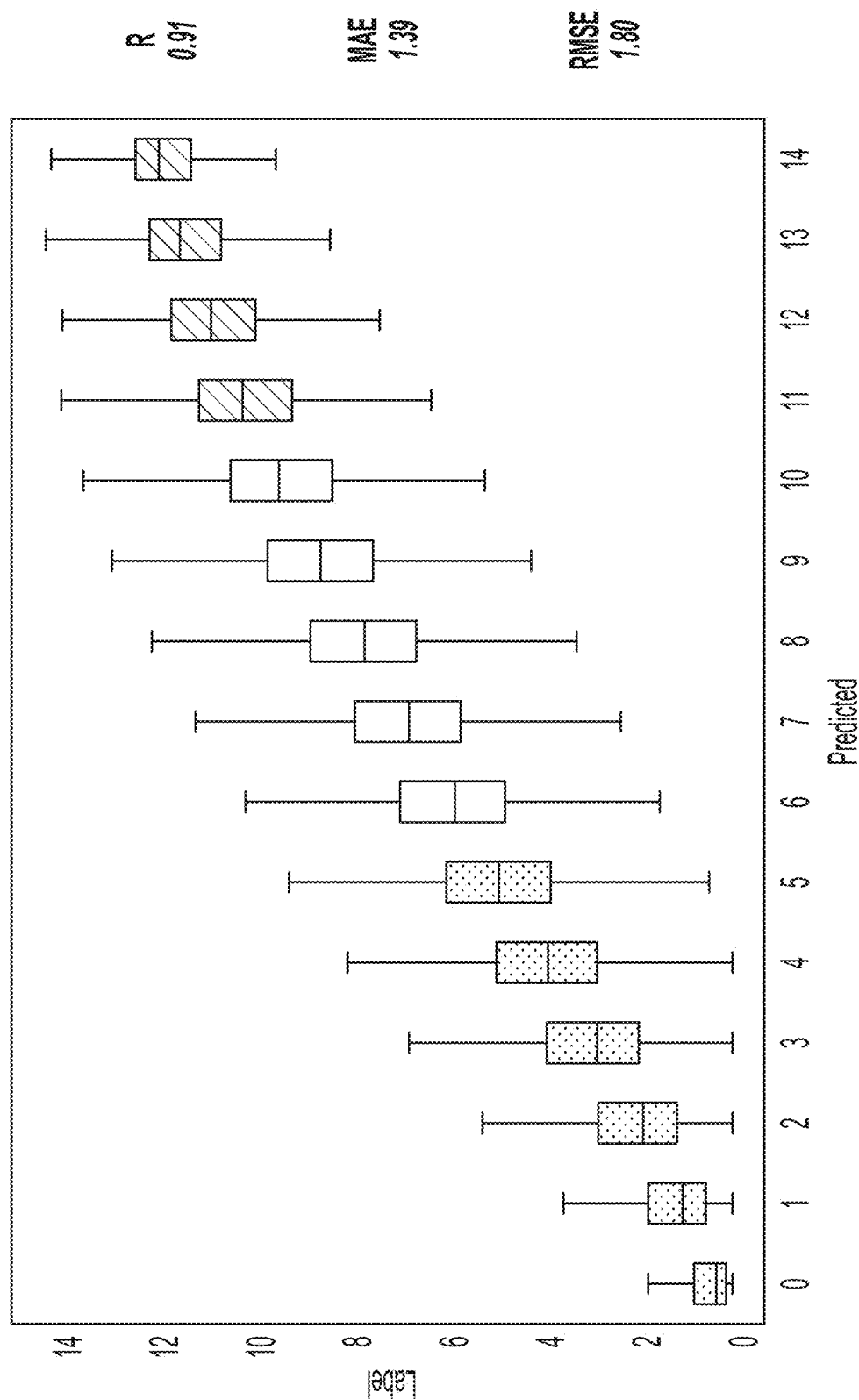
FIG. 32A is a candlestick chart demonstrating performance of a machine learning model used for computing interface scores in accordance with various embodiments described herein.
Figure 32B:
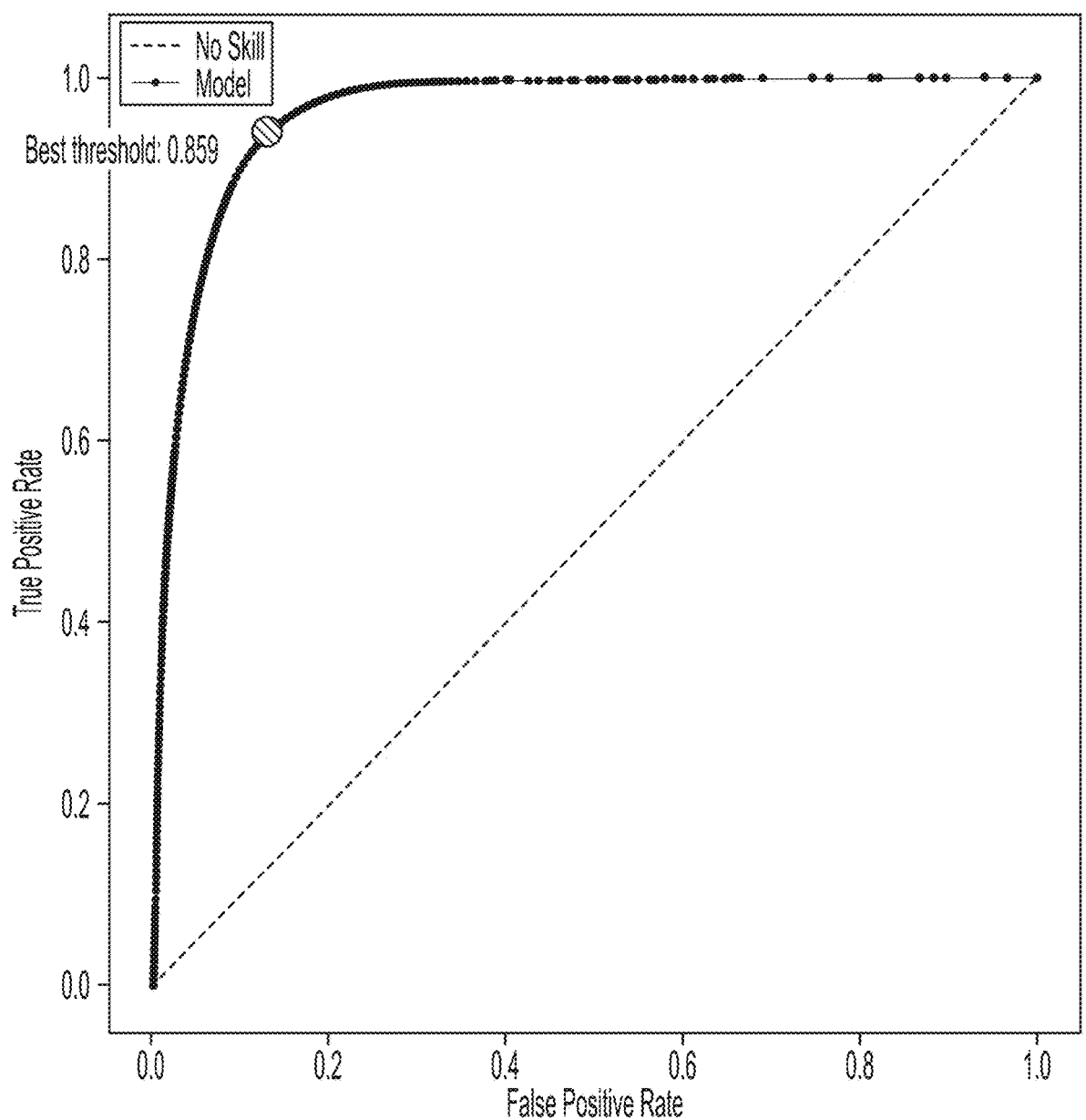
FIG. 32B is a graph showing a receiver operating characteristic (ROC) curve demonstrating performance of interface scores computed by a machine learning model as described herein for differentiation between native and non-native interfaces, in accordance with various embodiments described herein.

FIG. 32A shows a candlestick chart of the resulting performance of an interface scoring model implementing the example architecture shown in FIGS. 31A and B. Candlestick chart of FIG. 32A plots resulting label as a function of what was predicted. The performance, in this example, included an R value of 0.91, a MAE (mean absolute error, which is a measure of the number of mutations needed to get to a wild type interface) of 1.39, and an RMSE (root mean squared error) of 1.80. FIG. 32B demonstrates performance of an example use of an interface designer module in classifying interfaces as native or non-native (e.g., as a binary classifier) based on a predicted number of mutations predicted by an interface scoring model as shown in FIGS. 321A and B (a same model as used to generate the graph in FIG. 32A). The interface scoring model was tested with a testing dataset comprising 1,000 native/wild-type interfaces and 1,000 non-native interfaces, with a number of non-native examples for each bin (e.g., number of mutations) divided equally between the bins. The interface scoring model determined a predicted number of mutations for each example, and examples determined (by the interface scoring model) to have mutations below a selected threshold value were classified as native, and others, with a number of mutations above the selected threshold value were classified as non-native. As shown in FIG. 32B, for a selected threshold value of 0.859, use of the model predictions as a binary classifier resulted in an AUC of 0.96, a TPR of 0.94, accuracy of 0.91 and a FPR Of 0.13.

Figure 31B:
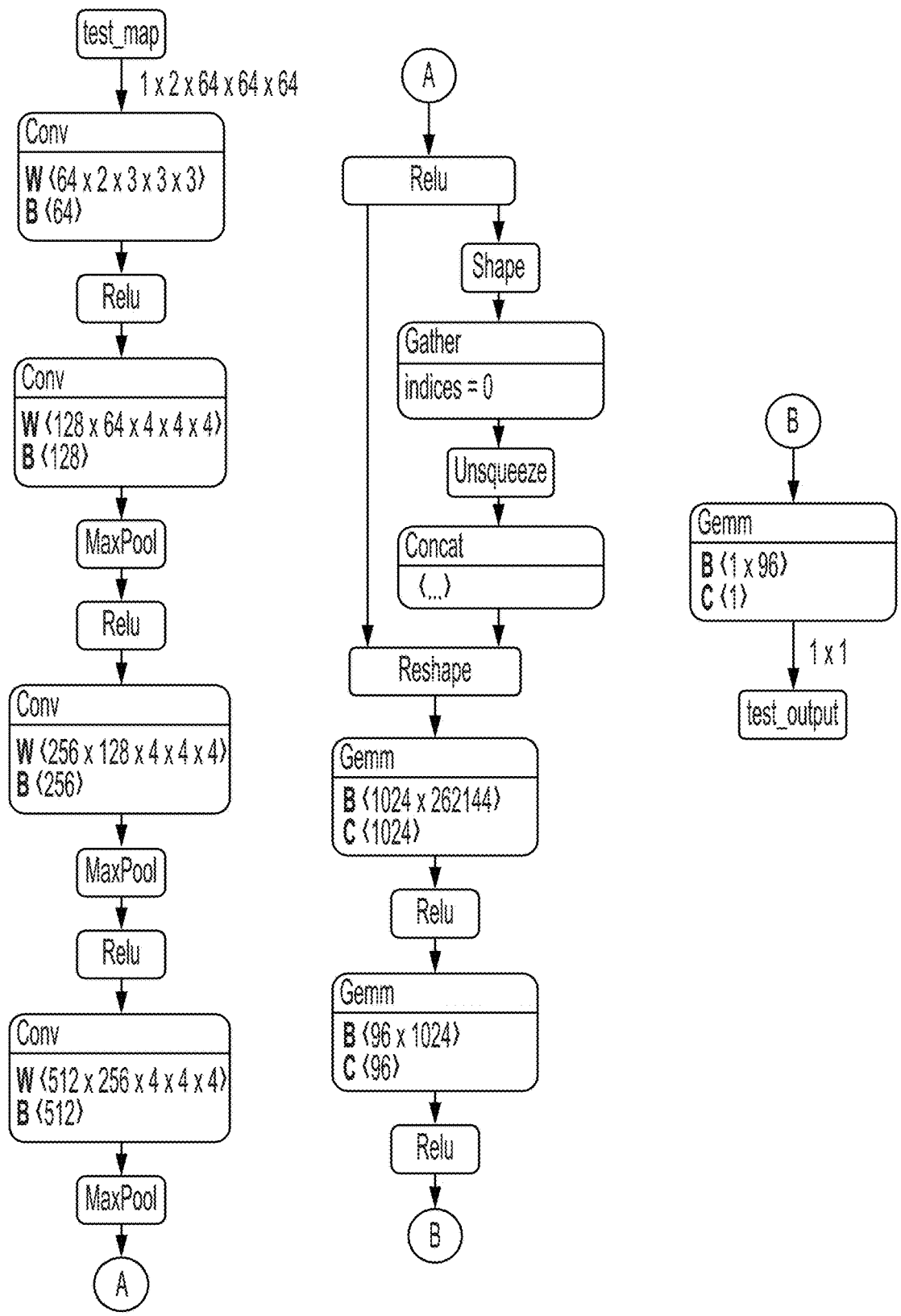
FIG. 31B is a network diagram of an example regression model machine learning architecture, according to an illustrative embodiment.

As described herein, the regression model architectures shown in and described with respect to FIGS. 31A and 31B may be used to implement an interface scoring model, for example, for use in an interface designer module as described herein. It should be understood, however, that particular model features and parameters, such as input size and resolution, kernel sizes, number of layers, etc. are exemplary and may be varied and used in accordance with various embodiments described herein. Such variations are contemplated in accordance with various embodiments described herein. Additionally or alternatively, in certain embodiments, such regression model architectures are not limited in use to interface scoring approaches and/or use within an interface designer module, and may be used in connection with other models, to generate other predictions, for example relevant to other scoring approaches (e.g., scaffold-pose scoring, binding affinity prediction, etc.) described herein. Additionally or alternatively, in certain embodiments, other regression model architectures may also be used, for example for determining interface scores and/or other scores described herein (e.g., scaffold pose scores, binding affinities, etc.).

iii. Example Interface Design Process

Figure 33:
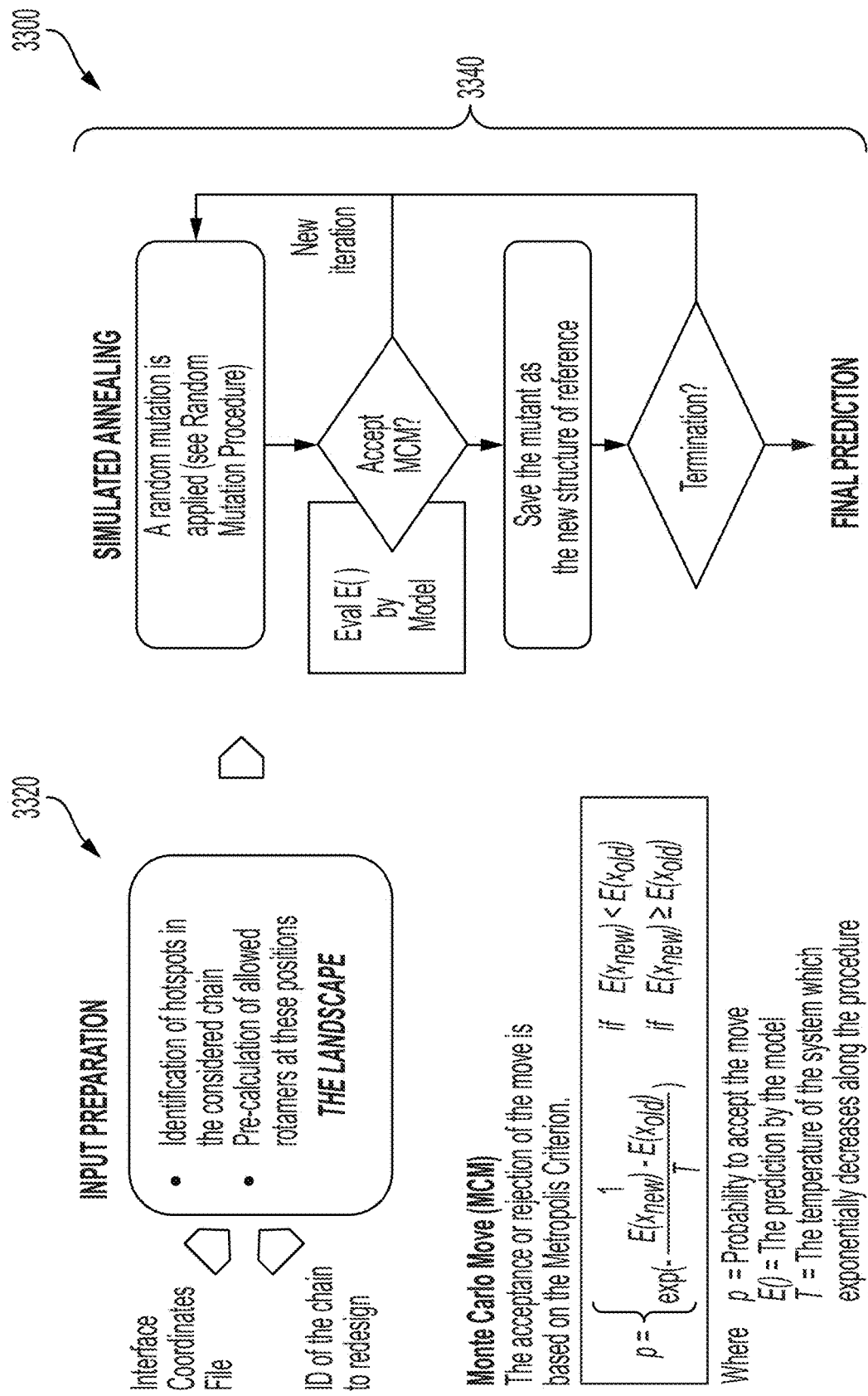
FIG. 33 is a diagram of an example process for designing candidate interfaces using an optimization algorithm, according to an illustrative embodiment.

Turning to FIG. 25 and FIG. 33, in certain embodiments a trained interface scoring model as described herein can be used in an interface designer module to design one or more ligand interfaces for binding to a particular target. As described herein, an interface designer module may utilize a scaffold-target complex model 2502 as a starting point. The interface designer module may then populate an interface region of the scaffold model of the scaffold-target complex model with amino acid side chains to create a ligand-target complex model which corresponds to the scaffold-target complex model, but with a ligand model representing a portion of the candidate peptide backbone with amino acid side chains populating sites that are located in proximity to the target. In certain embodiments, these populated sites comprise hotspots. In certain embodiments, populated sites also comprise context regions. The interface designer module may mutate amino acids in various sites (e.g., hotspots and/or context regions) of the ligand model to create a plurality of candidate ligand-target complex models, each representing a different candidate interface in a complex with the target 2510. In certain embodiments, generation of candidate ligand-target complex models may represent a ligand having a peptide backbone and pose thereof with respect to the target that is based on, but not necessarily identical to the candidate peptide backbone and pose of the scaffold-target complex model used as a starting point. For example, various ligand-target complex model may be created to account for, and represent variations of the candidate peptide backbone accounting for backbone flexibility. Additionally or alternatively, a pose of the initial scaffold-target complex model may be varied, for example via rigid body perturbations (e.g., random perturbations to one or more (e.g., of six) degrees of translational and/or rotations freedom. Such perturbations may allow for minor translations and/or rotations along one or more axis. In certain embodiments, such translations are within about 10 angstroms or less, (e.g., about 5 angstroms or less, about 1 angstrom or less, about 0.5 angstroms or less) along one or more directions (e.g., an x-, y, or z-, direction). In certain embodiments, rotational perturbations may be approximately 15 degrees or less (e.g., approximately 5 degrees or less, e.g., approximately one or two degrees or less) about one or more axes (e.g., x- and/or y- and/or z-axis).

In certain embodiments, volumetric representations, such as 3D EDMs are created from candidate ligand-target complex models and provided as input to a machine learning model such as an interface scoring model as described herein, thereby determining interface scores 2520 which can be used to rank and/or select a subset of interface designs that are likely to be successful 2530.

In certain embodiments, for example in order to efficiently search a landscape of possible interface designs, an interface designer module may leverage an optimization algorithm, such as simulated annealing, using an interface scoring model as an objective function whose output the optimization algorithm seeks to optimize. FIG. 33 shows an example process 3300 that utilizes a simulated annealing algorithm with an interface scoring model as an objective function. Process 3300 includes an input preparation step 3320 in which hotspots on a ligand-side of a ligand-target complex are identified, and certain pre-calculations, such as calculation of allowed rotamers at the identified hotspot locations, are performed. Following input preparation step 3320, a simulated annealing procedure is used to iteratively mutate amino acids at the identified hotspot locations to create a new candidate ligand-target complex model that represents the mutated interface and evaluate the new ligand target-complex using an interface scoring model to compute an interface score as described herein until a termination criteria is reached. For example, simulated annealing algorithm may terminate when one or more thresholds have been met; for example, a total of 6000 iterations have been run, or an interface score determined by the interface scoring model is less than 1 for twenty consecutive iterations.

In this manner, in certain embodiments, a subset of one or more ligand-target complex models, each representing a candidate interface determined, e.g., based on computed interface scores, as favorable. In certain embodiments, the subset of ligand-target complex models may then be used to design a custom biologic. In certain embodiments, one or more additional modules may be used to further refine designs of candidate interfaces based on the subset of ligand-target complex models.

F. Binding Affinity Predictor

Figure 34:
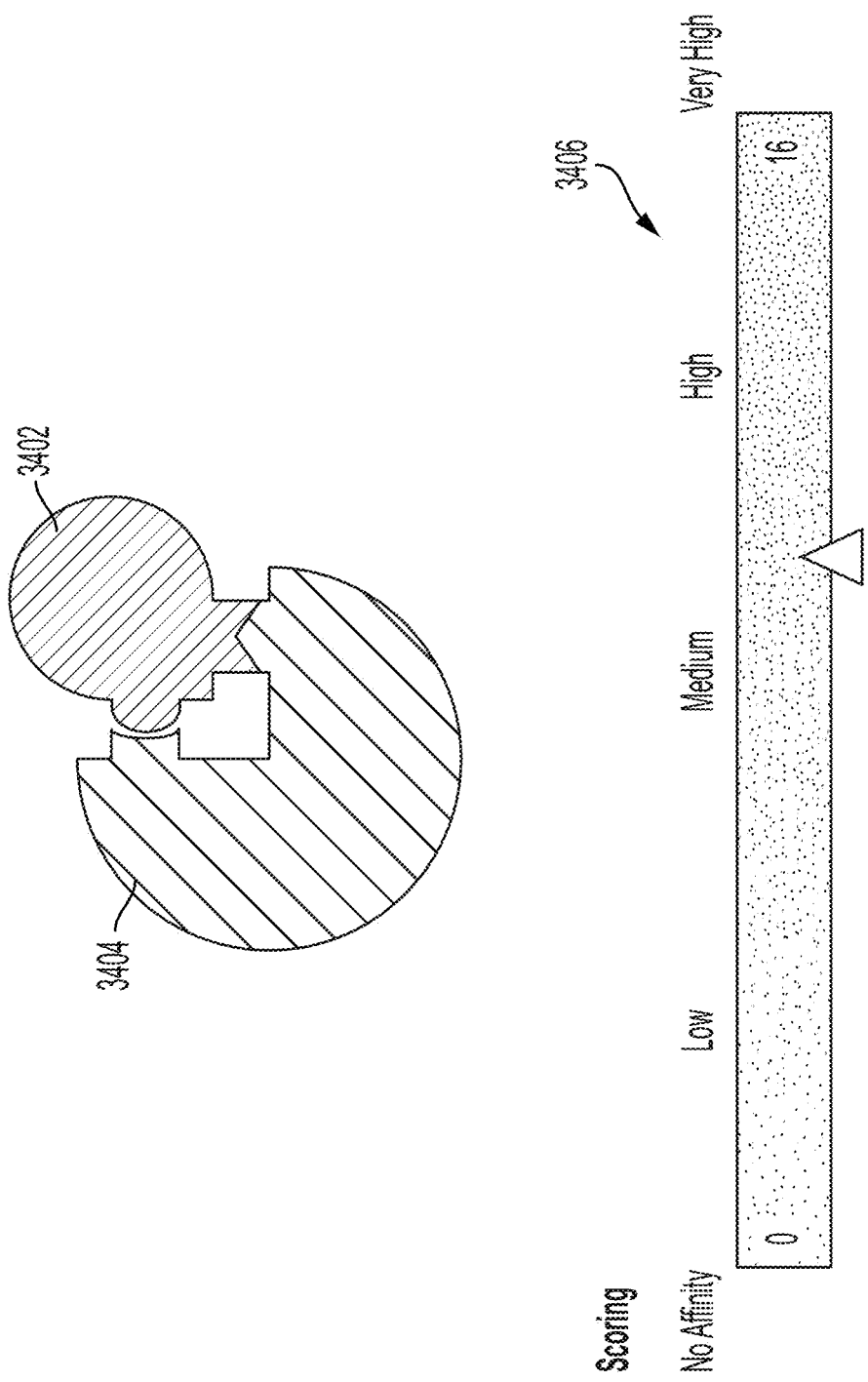
FIG. 34 is a schematic showing an example approach for evaluating performance of a binder candidate, according to an illustrative embodiment.

Turning to FIG. 34, in certain embodiments, in silico biologic design tools described herein include a binding affinity predictor module that can be used to predict a binding affinity between a particular ligand 3402 and target 3404. In certain embodiments, a binding affinity predictor module as described herein evaluates one or more ligand-target complex models and determines, for each, a predicted binding affinity score 3406. In certain embodiments, the predicted binding affinity score is a numerical value representing a predicted $pK_d$ value. In certain embodiments, the predicted binding affinity score is a classification (e.g., as determined via a machine learning model that acts as a classifier) and/or a value on a scale that is related (e.g., correlated with, proportional to, indicative of a range of) a binding affinity, e.g., $pK_d$, value.

In certain embodiments, a binding affinity predictor module utilizes a machine learning model to evaluate a particular ligand-target complex model and determine, as output, a binding affinity score. In certain embodiments, a binding affinity predictor's machine learning model receives, as input, a volumetric representation of at least a portion of the particular ligand-target complex model. For example, a 3D EDM may be generated from at least a portion, such as an extracted interface, of the particular ligand-target complex model, and used as input to the binding affinity predictor's machine learning model. In certain embodiments, a binding affinity score determined by the machine learning model corresponds directly to a (e.g., is a predicted) pKd value.

Figure 35:
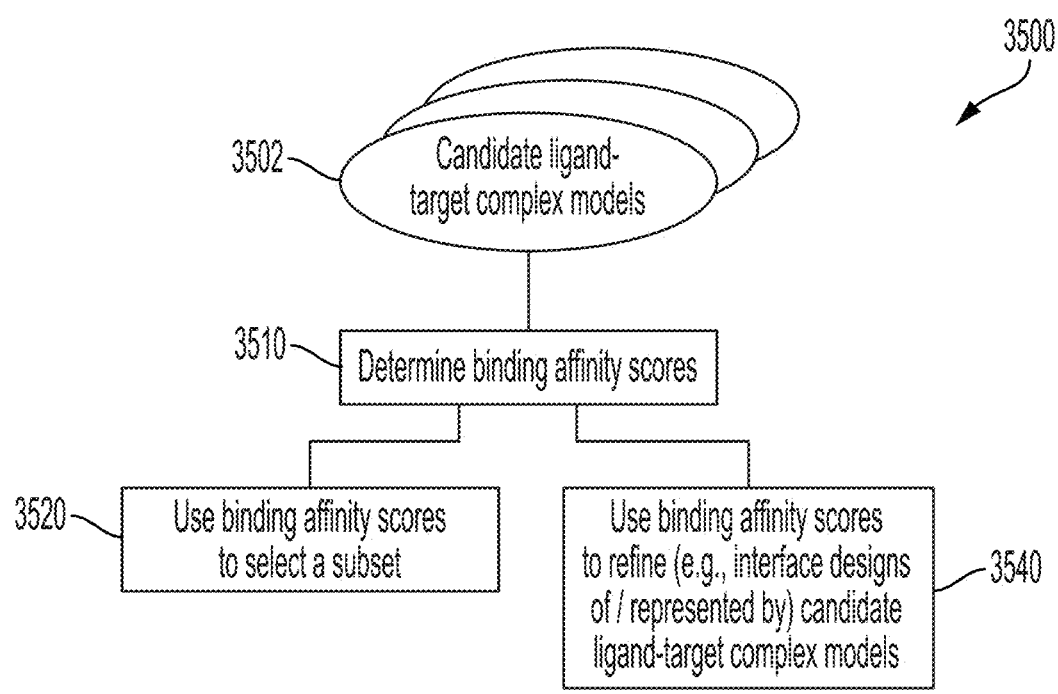
FIG. 35 is a block flow diagram of an example process for using predicted binding affinity scores to select a subset and/or refine candidate interface designs, according to an illustrative embodiment.

Turning to FIG. 35, in certain embodiments, which shows an example process 3500 for determining and using predicted binding affinity scores, a binding affinity module may receive, as input, a plurality of candidate ligand-target complex models, each representing a prospective custom biologic design 3502. For example, in certain embodiments, candidate ligand-target complex models are produced via other modules described herein, such as an interface designer module, and received as input by the binding affinity module. The binding affinity module may then use its machine learning model to determine predicted binding affinity scores 3510 for each of the candidate ligand-target complex models. In certain embodiments, a binding affinity module may select a subset of the candidate ligand-target complex models, based on the predicted binding affinity scores 3520, e.g., to determine a final set of designs for use in creating one or more new, engineered, custom biologics to be synthesized and experimentally tested. For example, the binding affinity module may rank candidate ligand-target complex models according to their predicted binding affinities, and select a portion, for example those having highest predicted affinities (e.g., a top 1, a top 5, those, lying in a particular upper percentile, etc.). Additionally or alternatively, in certain embodiments, a subset of ligand-target complex models may be selected and/or filtered by comparing predicted binding affinities to one or more threshold values.

Additionally or alternatively, in certain embodiments, a binding affinity predictor module may utilize predicted binding affinities to refine one or more received ligand-target complex models 3540. For example, in certain embodiments, one or more amino acids of a candidate ligand-target complex model may be mutated, and evaluated by a machine learning model to determine effects of various mutations on predicted binding affinities. In certain embodiments, mutations that improve binding affinity can be identified in this manner, and applied to an initial candidate ligand-target complex model to generate a find candidate, with improved binding affinity. In certain embodiments, optimization algorithms, for example as described herein, may be used to optimize binding affinity as a function of amino acid mutations, for example using received candidate ligand-target complex models as initial input and using predicted binding affinities generated via a machine learning model as an objective function to be optimized.

Accordingly, as described herein, binding affinity modules described herein may be utilized alone and/or incorporated in various custom biologic design pipelines and workflows to predict binding affinities for and/or further refine candidate biologic designs.

i. Example Machine Learning Model for Predicting Binding Affinities

As described herein, developing a machine learning model to generate accurate predictions and perform scoring functions as described herein involves steps and procedures including construction of an appropriate (e.g., balanced, sufficiently varied, etc.) training dataset, selecting a particular machine learning architecture and applying a training procedure, as well as validating performance. FIG. 36 through 39 describe an example implementation of a machine learning model used for predicting binding affinities, in accordance with certain embodiments described herein. Example implementation shown in FIG. 36 through 39 includes steps of training dataset construction, training, and validation. Accordingly, this example implementation demonstrates accurate predictions of binding affinities via machine learning approaches as described herein.

Training Dataset Construction

Figure 36:
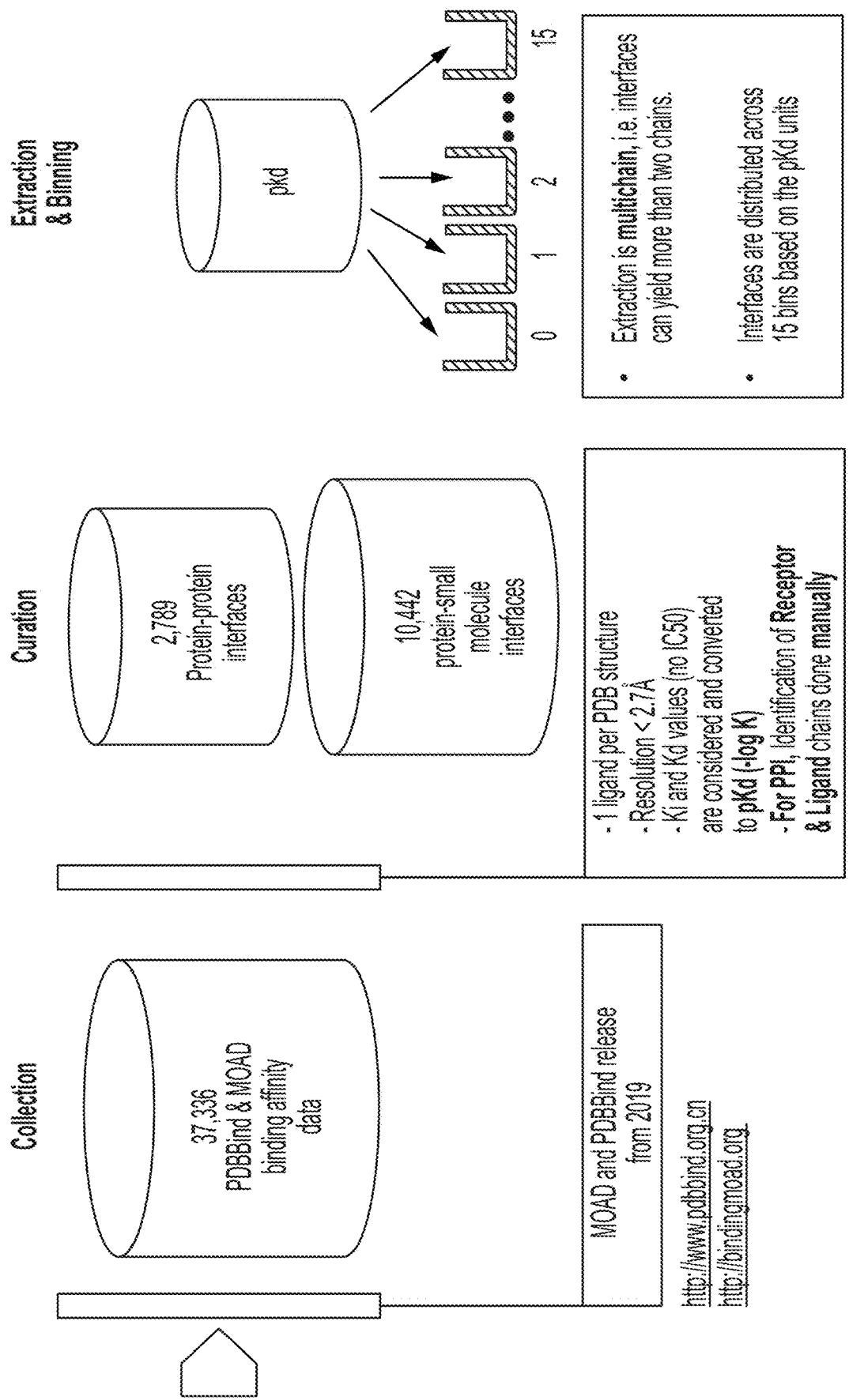
FIG. 36 is a schematic of an example approach for creating of a dataset for training a machine learning model for determining binding affinity predictions, according to an illustrative embodiment.
Figure 37:
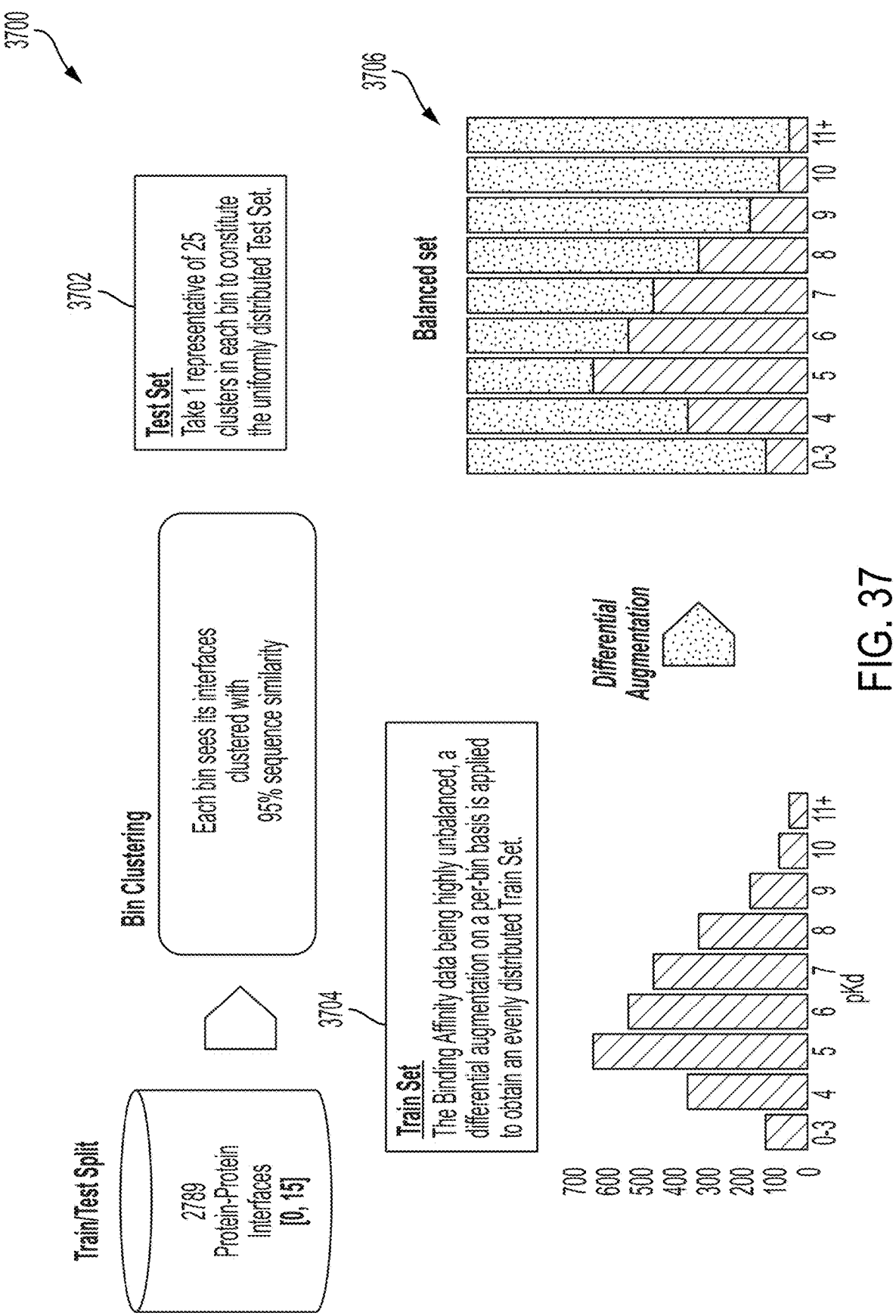
FIG. 37 is a schematic of an example approach, including balancing and data augmentation steps, for creating a dataset for training a machine learning model for determining binding affinity predictions, according to an illustrative embodiment.

Turning to FIG. 36, construction of a training dataset for binding affinity prediction may generally include data collection, data curation, data extraction and binning. Data collection may entail gathering binding affinity data from public databases such as PDB Bind and MOAD. In certain embodiments, $K_i$ (inhibition constant) and $K_d$ (dissociation constant) values are used and converted into $pK_d$ ($-\log K$) values to determine a measure of binding affinity for each ligand in the training set. In certain embodiments, only $K_i$ and $K_d$ values are used for determining binding affinity and IC50 values are not used/excluded. In certain embodiments, receptor and ligand chains are identified manually. Data extraction may be multi-chain meaning that a single interface may yield multiple side chains. The interfaces may be distributed across 15 bins based on $pK_d$ units.

Turning to FIG. 36, creation of a training dataset used in binding affinity prediction may include clustering protein-protein interfaces into bins that share 95% sequence similarity. A single interface may then be selected from each of the (for example, 25) bins to act as a representative for that bin to be used in a uniformly distributed test set (i.e., for testing the model). The remaining interfaces may be used for training. In order to achieve a balanced set, a differential augmentation on a per-bin basis (for example, based on $pK_d$ value) may be used to obtain an evenly distributed training set.

In an example implementation, a training set created in this manner included about 7250 entries per bin while the testing set included about 1000 entries per bin with labels ranging uniformly from 0 to 15. In this example implementation, this approach resulted in a total of about 65,184 entries in the training data set and t a total of about 8,928 entries in the testing data set. Interface extraction was performed and each extracted interface converted to a 3D EDM. Accordingly, in certain embodiments, the training set may include from about 5 to about 10 times (or from about 6 to about 9 times, or from about 7 time to about 8 times) more entries than the testing set. Stated otherwise, from about 70% to about 95% (or from about 75% to about 90%, or from about 80% to about 90%) of the total number of entries may be used for model training, while the remaining entries (or data points) may be used for testing.

Example Training Approach

Figure 38:
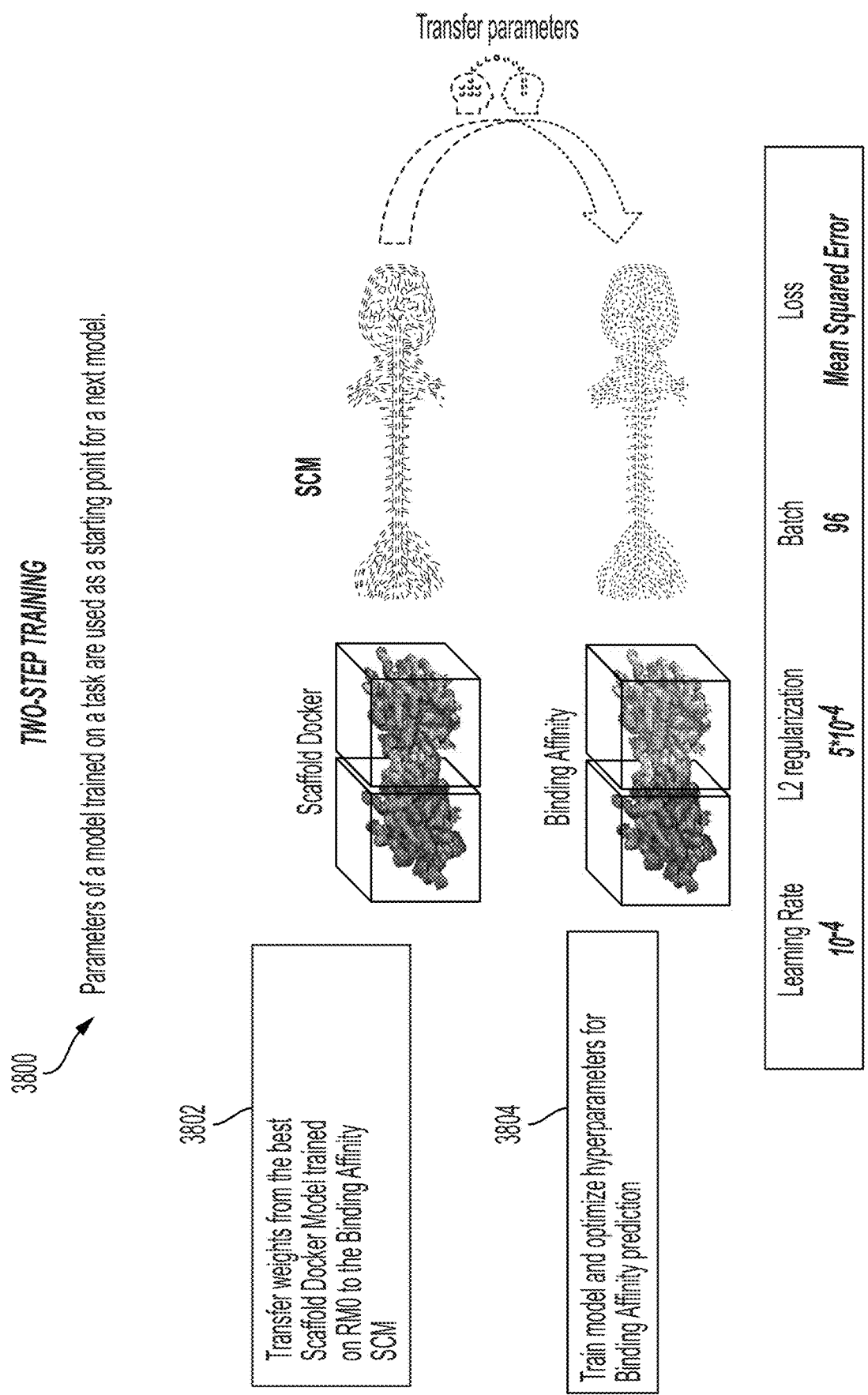
FIG. 38 is a schematic of a two-step transfer learning approach for training a machine learning model, according to an illustrative embodiment.

FIG. 38 illustrates an approach to two-step training used in binding affinity prediction, used in certain embodiments. The approach to two-step training may include a first step in which weights from a best scaffold docker model trained on RM0 (i.e., one of the RMSD models) may be transferred to the binding affinity spinal cord model (SCM). The approach to two-step training may also include a second step in which the model is trained and hyperparameters are optimized for binding affinity prediction. Weights for layers of an SCM trained for a scaffold docker model were transferred, apart from a final, fully-connected layer that outputs a single value and was trained on a binding affinity dataset created as described herein. Without wishing to be bound to any particular theory, in certain embodiments a transfer learning approach such as the approach shown in FIG. 38 provides for accurate training of a machine learning model even when a limited dataset is used, by leveraging training performed on a related (though not identical) task for which a more extensive dataset is available. In certain embodiments, this approaches allows for creation of an accurate binding affinity predictor machine learning model, despite relatively limited experimental binding affinity data.

Performance Example

Figure 39:
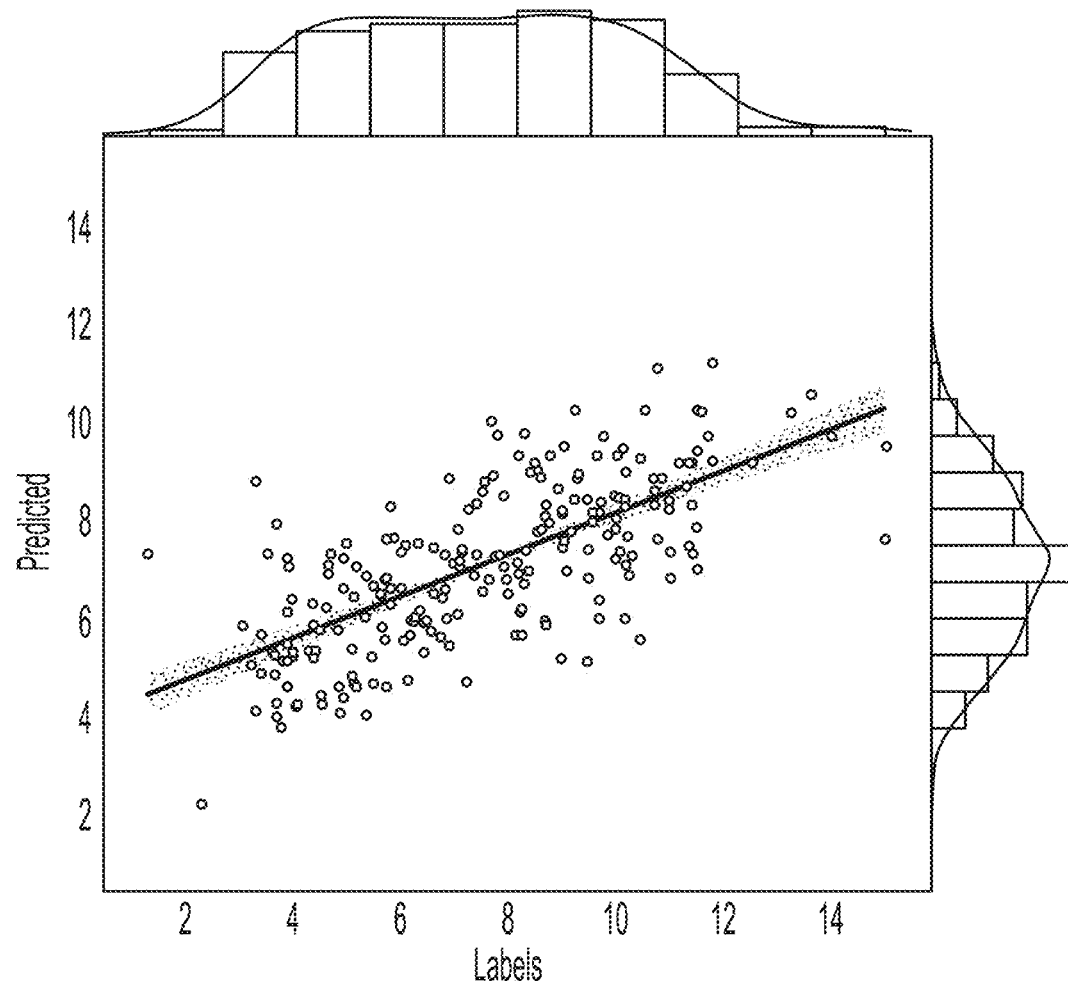
FIG. 39 is a graph demonstrating performance of a machine learning model used for determining binding affinity predictions, according to an illustrative embodiment.

FIG. 39 illustrates performance results for binding affinity predictions, used in certain embodiments. The performance, in this example, included an R value of 0.7, a MAE (mean absolute error, which is a measure of the number of mutations needed to get to a wild type interface) of 1.54, and an RMSE (root mean squared error) of 1.98.

Accordingly, embodiments of the binding affinity module described herein include various features that facilitate accurate prediction of binding affinity, and generate models capable of more accurate predictions than other (e.g., previous) approaches.

G. Additional Modules and Flexible, Modular, Pipeline Architecture

As described herein, embodiments of various modules described herein—such as the scaffold docker module, interface designer, and binding affinity predictor may be utilized separate and/or in combination to engineer structural features of custom biologics with respect particular criteria (e.g., each module evaluating and facilitating design with respect to a particular criteria). In certain embodiments, these modules, as well as various other modules may be used individually or combined with each other, in pipeline architectures as described herein, e.g., with respect to design of custom binders, as well as other architectures and organizations.

Figure 40:
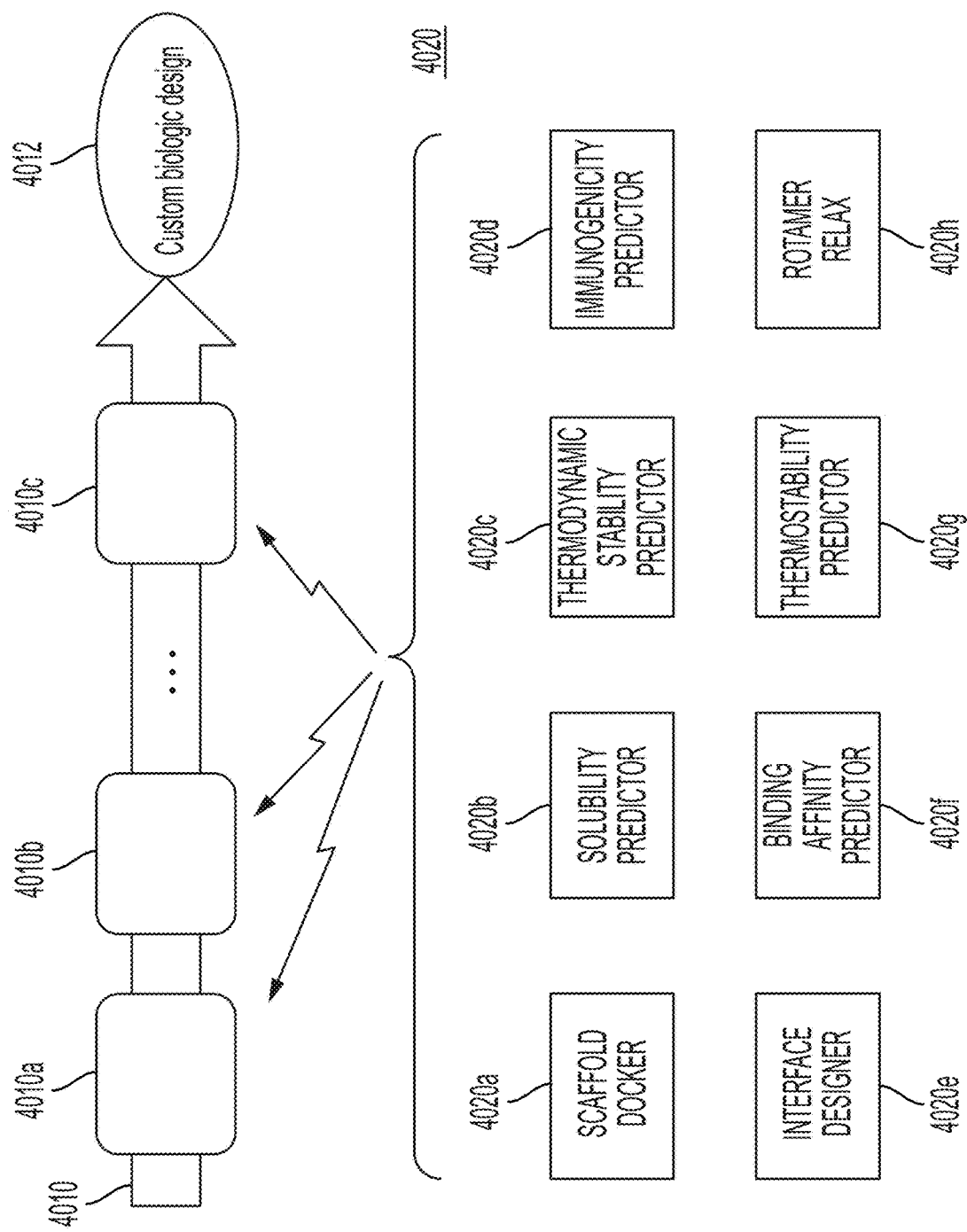
FIG. 40 is a schematic showing an example modular approach for designing custom biologics, according to an illustrative embodiment.

For example, as shown in FIG. 40*a* modular approach as described herein allows, in certain embodiments, for creation of various custom pipelines 4010, tailored for a particular design task, to create various custom biologic designs 4012 having particular desired functionality. Various pipelines can be created in a flexible manner, via selection and arrangement of various modules from a collection of modules 4020. In certain embodiments, module collection may include one or more of a scaffold docker module 4020*a*, an interface designer module, 4020*e*, and a binding affinity predictor module 4020*f* as described herein. In certain embodiments, module collection 4020 may include various other modules, such, without limitation, any of a rotamer relax module 4020h, a solubility prediction module 4020b, a thermodynamic stability prediction module 4020c, an immunogenicity prediction module 4020d, and a thermostability prediction module 4020g. In certain embodiments, as with the scaffold docker, interface designer, and binding affinity predictor modules, these modules may be used, along with the scaffold docker, interface designer and binding affinity predictor modules, in various combinations, sequentially or in parallel fashion, depending on a particular application.

In certain embodiments, approaches described herein with regard to a scaffold docker module may be used to create a ligand docking module that identifies docking configurations of two peptide and/or polypeptide chains. In particular, instead of operating on scaffold models, various dataset creation, training, sampling and scoring procedures described herein with regard to a scaffold docker module may be performed using two or more ligand models, each of which represents a full ligand—i.e., including amino acid side chains. In this manner, favorable orientations of full ligands for binding with respect to each other may be identified—providing a tool for, among other things, handling classical protein and/or peptide docking.

H. Computer System and Network Environment

Figure 41:
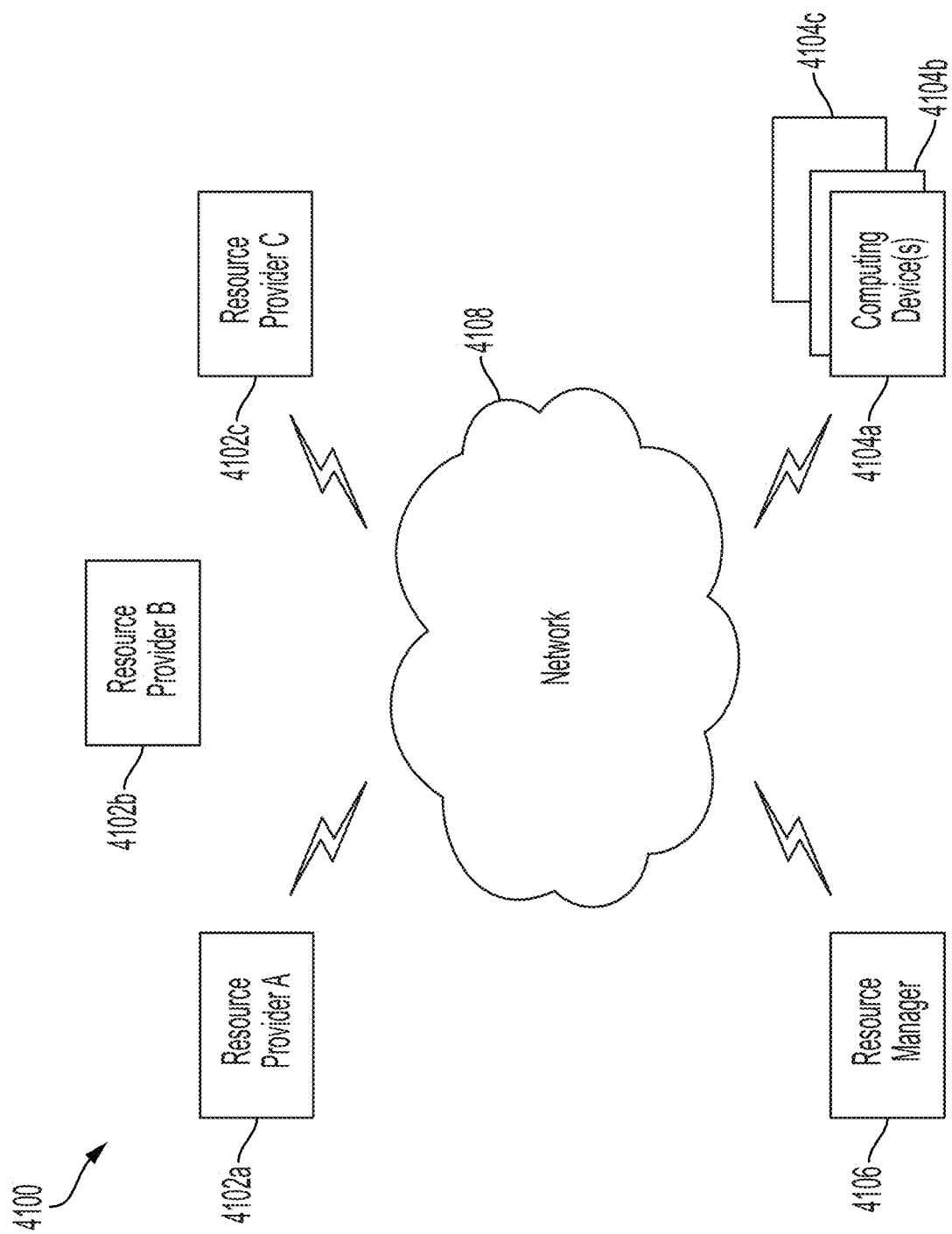
FIG. 41 is a block diagram of an exemplary cloud computing environment, used in certain embodiments.

Turning to FIG. 41, an implementation of a network environment 4100 for use in providing systems, methods, and architectures as described herein is shown and described. In brief overview, referring now to FIG. 41, a block diagram of an exemplary cloud computing environment 4100 is shown and described. The cloud computing environment 4100 may include one or more resource providers 4102a, 4102b, 4102c (collectively, 4102). Each resource provider 4102 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 4102 may be connected to any other resource provider 4102 in the cloud computing environment 4100. In some implementations, the resource providers 4102 may be connected over a computer network 4108. Each resource provider 4102 may be connected to one or more computing device 4104a, 4104b, 4104c (collectively, 4104), over the computer network 4108.

The cloud computing environment 4100 may include a resource manager 4106. The resource manager 4106 may be connected to the resource providers 4102 and the computing devices 4104 over the computer network 4108. In some implementations, the resource manager 4106 may facilitate the provision of computing resources by one or more resource providers 4102 to one or more computing devices 4104. The resource manager 4106 may receive a request for a computing resource from a particular computing device 4104. The resource manager 4106 may identify one or more resource providers 4102 capable of providing the computing resource requested by the computing device 4104. The resource manager 4106 may select a resource provider 4102 to provide the computing resource. The resource manager 4106 may facilitate a connection between the resource provider 4102 and a particular computing device 4104. In some implementations, the resource manager 4106 may establish a connection between a particular resource provider 4102 and a particular computing device 4104. In some implementations, the resource manager 4106 may redirect a particular computing device 4104 to a particular resource provider 4102 with the requested computing resource.

Figure 42:
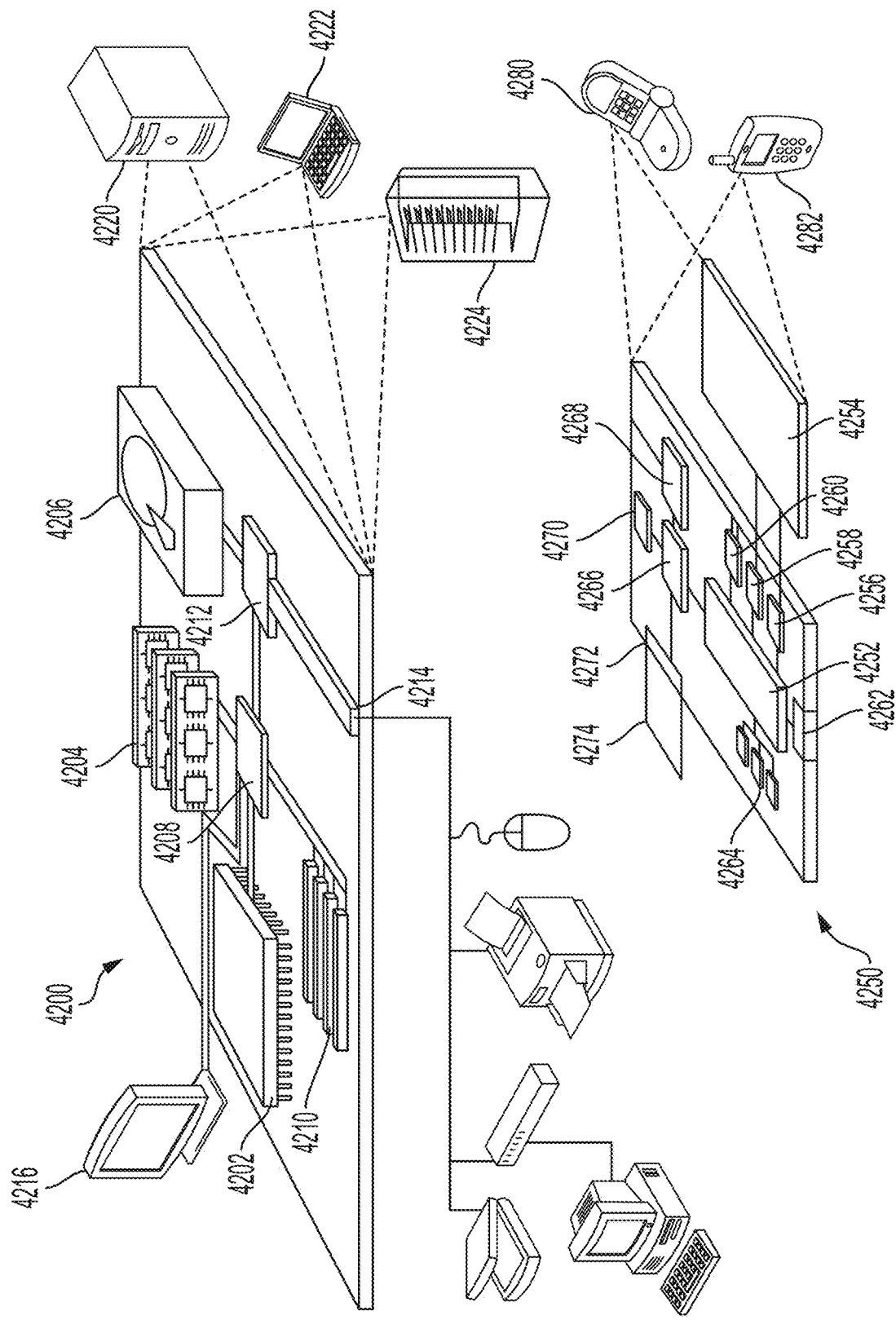
FIG. 42 is a block diagram of an example computing device and an example mobile computing device, used in certain embodiments.

FIG. 42 shows an example of a computing device 4200 and a mobile computing device 4250 that can be used to implement the techniques described in this disclosure. The computing device 4200 is intended to represent various forms of digital computers, such as laptops, desktops, workstations, personal digital assistants, servers, blade servers, mainframes, and other appropriate computers. The mobile computing device 4250 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 4200 includes a processor 4202, a memory 4204, a storage device 4206, a high-speed interface 4208 connecting to the memory 4204 and multiple high-speed expansion ports 4210, and a low-speed interface 4212 connecting to a low-speed expansion port 4214 and the storage device 4206. Each of the processor 4202, the memory 4204, the storage device 4206, the high-speed interface 4208, the high-speed expansion ports 4210, and the low-speed interface 4212, are interconnected using various busses, and may be mounted on a common motherboard or in other manners as appropriate. The processor 4202 can process instructions for execution within the computing device 4200, including instructions stored in the memory 4204 or on the storage device 4206 to display graphical information for a GUI on an external input/output device, such as a display 4216 coupled to the high-speed interface 4208. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 4204 stores information within the computing device 4200. In some implementations, the memory 4204 is a volatile memory unit or units. In some implementations, the memory 4204 is a non-volatile memory unit or units. The memory 4204 may also be another form of computer-readable medium, such as a magnetic or optical disk.

The storage device 4206 is capable of providing mass storage for the computing device 4200. In some implementations, the storage device 4206 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 4202), perform one or more methods, such as those described above. The instructions can also be stored by one or more storage devices such as computer- or machine-readable mediums (for example, the memory 4204, the storage device 4206, or memory on the processor 4202).

The high-speed interface 4208 manages bandwidth-intensive operations for the computing device 4200, while the low-speed interface 4212 manages lower bandwidth-intensive operations. Such allocation of functions is an example only. In some implementations, the high-speed interface 4208 is coupled to the memory 4204, the display 4216 (e.g., through a graphics processor or accelerator), and to the high-speed expansion ports 4210, which may accept various expansion cards (not shown). In the implementation, the low-speed interface 4212 is coupled to the storage device 4206 and the low-speed expansion port 4214. The low-speed expansion port 4214, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 4200 may be implemented in a number of different forms, as shown in the figure. For example, it may be implemented as a standard server 4220, or multiple times in a group of such servers. In addition, it may be implemented in a personal computer such as a laptop computer 4222. It may also be implemented as part of a rack server system 4224. Alternatively, components from the computing device 4200 may be combined with other components in a mobile device (not shown), such as a mobile computing device 4250. Each of such devices may contain one or more of the computing device 4200 and the mobile computing device 4250, and an entire system may be made up of multiple computing devices communicating with each other.

The mobile computing device 4250 includes a processor 4252, a memory 4264, an input/output device such as a display 4254, a communication interface 4266, and a transceiver 4268, among other components. The mobile computing device 4250 may also be provided with a storage device, such as a micro-drive or other device, to provide additional storage. Each of the processor 4252, the memory 4264, the display 4254, the communication interface 4266, and the transceiver 4268, are interconnected using various buses, and several of the components may be mounted on a common motherboard or in other manners as appropriate.

The processor 4252 can execute instructions within the mobile computing device 4250, including instructions stored in the memory 4264. The processor 4252 may be implemented as a chipset of chips that include separate and multiple analog and digital processors. The processor 4252 may provide, for example, for coordination of the other components of the mobile computing device 4250, such as control of user interfaces, applications run by the mobile computing device 4250, and wireless communication by the mobile computing device 4250.

The processor 4252 may communicate with a user through a control interface 4258 and a display interface 4256 coupled to the display 4254. The display 4254 may be, for example, a TFT (Thin-Film-Transistor Liquid Crystal Display) display or an OLED (Organic Light Emitting Diode) display, or other appropriate display technology. The display interface 4256 may comprise appropriate circuitry for driving the display 4254 to present graphical and other information to a user. The control interface 4258 may receive commands from a user and convert them for submission to the processor 4252. In addition, an external interface 4262 may provide communication with the processor 4252, so as to enable near area communication of the mobile computing device 4250 with other devices. The external interface 4262 may provide, for example, for wired communication in some implementations, or for wireless communication in other implementations, and multiple interfaces may also be used.

The memory 4264 stores information within the mobile computing device 4250. The memory 4264 can be implemented as one or more of a computer-readable medium or media, a volatile memory unit or units, or a non-volatile memory unit or units. An expansion memory 4274 may also be provided and connected to the mobile computing device 4250 through an expansion interface 4272, which may include, for example, a SIMM (Single In Line Memory Module) card interface. The expansion memory 4274 may provide extra storage space for the mobile computing device 4250, or may also store applications or other information for the mobile computing device 4250. Specifically, the expansion memory 4274 may include instructions to carry out or supplement the processes described above, and may include secure information also. Thus, for example, the expansion memory 4274 may be provide as a security module for the mobile computing device 4250, and may be programmed with instructions that permit secure use of the mobile computing device 4250. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 4252), perform one or more methods, such as those described above. The instructions can also be stored by one or more storage devices, such as one or more computer- or machine-readable mediums (for example, the memory 4264, the expansion memory 4274, or memory on the processor 4252). In some implementations, the instructions can be received in a propagated signal, for example, over the transceiver 4268 or the external interface 4262.

The mobile computing device 4250 may communicate wirelessly through the communication interface 4266, which may include digital signal processing circuitry where necessary. The communication interface 4266 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 4268 using a radio-frequency. In addition, short-range communication may occur, such as using a Bluetooth®, Wi-Fi™, or other such transceiver (not shown). In addition, a GPS (Global Positioning System) receiver module 4270 may provide additional navigation- and location-related wireless data to the mobile computing device 4250, which may be used as appropriate by applications running on the mobile computing device 4250.

The mobile computing device 4250 may also communicate audibly using an audio codec 4260, which may receive spoken information from a user and convert it to usable digital information. The audio codec 4260 may likewise generate audible sound for a user, such as through a speaker, e.g., in a handset of the mobile computing device 4250. Such sound may include sound from voice telephone calls, may include recorded sound (e.g., voice messages, music files, etc.) and may also include sound generated by applications operating on the mobile computing device 4250.

The mobile computing device 4250 may be implemented in a number of different forms, as shown in the figure. For example, it may be implemented as a cellular telephone 4280. It may also be implemented as part of a smart-phone 4282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Actions associated with implementing the systems may be performed by one or more programmable processors executing one or more computer programs. All or part of the systems may be implemented as special purpose logic circuitry, for example, a field programmable gate array (FPGA) or an application-specific integrated circuit (ASIC), or both. All or part of the systems may also be implemented as special purpose logic circuitry, for example, a specially designed (or configured) central processing unit (CPU), conventional central processing units (CPU) a graphics processing unit (GPU), and/or a tensor processing unit (TPU).

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

EQUIVALENTS

It is to be understood that while the disclosure has been described in conjunction with the detailed description thereof, the foregoing description is intended to illustrate and not limit the scope of the claims. Other aspects, advantages, and modifications are within the scope of the claims.

This written description uses examples to disclose the invention, including the best mode, and also to enable any person skilled in the art to practice the present embodiments, including making and using any devices or systems and performing any incorporated methods. The patentable scope of the present embodiments is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for designing a custom biologic structure for binding to a target via an artificial intelligence (AI)-powered interface designer module, the method comprising:
   (a) receiving and/or generating, by a processor of a computing device, a scaffold-target complex model that represents at least a portion of a complex comprising the target and a particular candidate peptide backbone on which to build a custom interface portion of a ligand for binding to the target, wherein the particular candidate peptide backbone is oriented at a particular pose with respect to the target and the scaffold-target complex model comprises a representation of (i) at least a portion of the target and (ii) at least a portion of the candidate peptide backbone, said portions of the target and candidate peptide backbone located in proximity to each other and forming a potential binding interface;
   (b) generating, by the processor, based on the scaffold-target complex model, one or more prospective ligand-target complex models, each representing at least a portion of a complex comprising the target and a particular prospective ligand, each particular prospective ligand: (i) having a peptide backbone corresponding to the particular candidate peptide backbone, (ii) positioned with respect to the target based on the particular pose, and (iii) comprising at least an interface region, located in proximity to the target, populated with amino acids, such that each particular prospective ligand comprises a particular amino acid population at its interface region;
   (c) for each of the one or more prospective ligand-target complex models, determining, by the processor, an interface score using a machine learning model, thereby determining one or more interface scores;
   (d) selecting, by the processor, a subset of the prospective ligand-target complex models based on at least a portion of the one or more interface scores; and
   (e) providing the selected subset of prospective ligand-target complex models for use in designing the custom biologic structure for binding to the target.

2. The method of claim 1, wherein the candidate peptide backbone comprises a length of less than about 100 peptide bonds and/or greater than about 20 peptide bonds.

3. The method of claim 1, wherein the candidate peptide backbone is a backbone of a pre-existing protein molecule.

4. The method of claim 1, comprising identifying, by the processor, an interface sub-region of the scaffold-target complex model, the interface sub-region comprising representations of atoms of the candidate peptide backbone and/or the target located in proximity to an interface between the candidate peptide backbone and/or the target.

5. The method of claim 1, wherein step (b) comprises assigning an initial amino acid sequence to an interface region of the candidate peptide backbone and mutating amino acids to generate, for each prospective ligand-target complex model, the particular amino acid population at the interface region of the prospective ligand.

6. The method of claim 1, wherein step (c) comprises receiving and/or generating, for each particular one of the one or more prospective ligand-target complex models, a simulated three-dimensional electron density map (3D EDM) corresponding to at least a portion of the particular prospective ligand-target complex model and using the simulated 3D EDM as input to the machine learning model.

7. The method of claim 1, wherein the machine learning model receives, as input, for each particular prospective ligand-target complex model, a candidate interface representation based on and representing at least the interface region of the particular prospective ligand-target complex model and outputs, for the particular prospective ligand-target complex model, as the interface score, a measure of similarity and/or dissimilarity between the candidate interface representation and representations of native interfaces.

8. The method of claim 7, wherein the machine learning model is a trained model, having been trained to determine a predicted number of mutations between (i) candidate interface representations received as input and (ii) the representations of native interfaces.

9. The method of claim 1, wherein the machine learning model has been trained using training data comprising:
   (A) a plurality of native interface models, each native interface model representing at least a portion of a native interface based on an experimentally determined structural model of the native interface; and
   (B) a plurality of artificially generated mutant interface models, each mutant interface model based on a mutated version of a native interface.

10. The method of claim 1, wherein the machine learning model comprises a neural network.

11. The method of claim 1, comprising using, by the processor, an optimization routine to select the subset of the prospective ligand-target complex models.

12. The method of claim 1, wherein the target comprises a member selected from the group consisting of a peptide, a peptide complex, a protein, and a protein complex.

13. The method of claim 1, further comprising, for each of at least a portion of the prospective ligand-target complex models, determining, by the processor, a binding affinity score using a machine learning model that receives, as input, a representation of at least a portion of a particular ligand-target complex model and outputs, as the binding affinity score, a value representing a predicted binding affinity between the prospective custom biologic structure and the target molecule of the particular ligand-target complex model; and using the one or more binding affinity scores to design the custom biologic structure.

14. The method of claim 13, comprising:
   selecting one or more high binding affinity ligand-target complex models based on the one or more binding affinity scores; and
   providing the one or more high binding affinity ligand-target complex models for use in designing the custom biologic structure.

15. The method of claim 14, comprising comparing the one or more binding affinity scores to a threshold value and/or ranking the prospective ligand target-complex models according to the one or more determined binding affinity scores.

16. A system for in silico design of a custom biologic structure for binding to a target via an artificial intelligence (AI)-powered interface designer module, the system comprising:
   a processor of a computing device; and
   a memory having instructions stored thereon, wherein the instructions, when executed by the processor, cause the processor to:
   (a) receive and/or generate a scaffold-target complex model that represents at least a portion of a complex comprising the target and a particular candidate peptide backbone on which to build a custom interface portion of a ligand for binding to the target, wherein the particular candidate peptide backbone is oriented at a particular pose with respect to the target and the scaffold-target complex model comprises a representation of (i) at least a portion of the target and (ii) at least a portion of the candidate peptide backbone, said portions of the target and candidate peptide backbone located in proximity to each other and forming a potential binding interface;

(b) generate, based on the scaffold-target complex model, one or more prospective ligand-target complex models, each representing at least a portion of a complex comprising the target and a particular prospective ligand, each particular prospective ligand: (i) having a peptide backbone corresponding to the particular candidate peptide backbone, (ii) positioned with respect to the target based on the particular pose, and (iii) comprising at least an interface region, located in proximity to the target, populated with amino acids, such that each particular prospective ligand comprises a particular amino acid population at its interface region;

(c) for each of the one or more prospective ligand-target complex models, determine an interface score using a machine learning model, thereby determining one or more interface scores;

(d) select a subset of the prospective ligand-target complex models based on at least a portion of the one or more interface scores; and (e) provide the selected subset of prospective ligand-target complex models for use in designing the custom biologic structure for binding to the target.

17. The system of claim 16, wherein the candidate peptide backbone is a backbone of a pre-existing protein and/or peptide.

18. The system of claim 16, wherein the instructions cause the processor to identify an interface sub-region of the scaffold-target complex model, the interface sub-region comprising representations of atoms of the candidate peptide backbone and/or the target located in proximity to an interface between the candidate peptide backbone and/or the target.

19. The system of claim 16, wherein the instructions cause the processor to, at step (b), assign an initial amino acid sequence to an interface region of the candidate peptide backbone and mutate amino acids to generate, for each prospective ligand-target complex model, the particular amino acid population at the interface region of the prospective ligand.

20. The system of claim 16, wherein, at step (c), the instructions cause the processor to:
receive and/or generate, for each particular one of the one or more prospective ligand-target complex models, a simulated three-dimensional electron density map (3D EDM) corresponding to at least a portion of the particular prospective ligand-target complex model; and
use the simulated 3D EDM as input to the machine learning model.

21. The system of claim 16, wherein the machine learning model receives, as input, for each particular prospective ligand-target complex model, a candidate interface representation based on and representing at least the interface region of the particular prospective ligand-target complex model and outputs, for the particular prospective ligand-target complex model, as the interface score, a measure of similarity and/or dissimilarity between the candidate interface representation and representations of native interfaces.

22. The system of claim 21, wherein the machine learning model is a trained model, having been trained to determine a predicted number of mutations between (i) candidate interface representations received as input and (ii) the representations of native interfaces.

23. The system of claim 16, wherein the machine learning model has been trained using training data comprising:
(A) a plurality of native interface models, each native interface model representing at least a portion of a native interface based on an experimentally determined structural model of the native interface; and
(B) a plurality of artificially generated mutant interface models, each mutant interface model based on a mutated version of a native interface.

24. The system of claim 16, wherein the machine learning model comprises a neural network.

25. The system of claim 16, wherein the instructions cause the processor to use an optimization routine to select the subset of the prospective ligand-target complex models.

26. The system of claim 16, wherein the target comprises a member selected from the group consisting of a peptide, a peptide complex, a protein, and a protein complex.

27. The system of claim 16, wherein the instructions cause the processor to, for each of at least a portion of the prospective ligand-target complex models, determine a binding affinity score using a machine learning model that receives, as input, a representation of at least a portion of a particular ligand-target complex model and outputs, as the binding affinity score, a value representing a predicted binding affinity between the prospective custom biologic structure and the target molecule of the particular ligand-target complex model; and use the one or more binding affinity scores to design the custom biologic structure.

28. The system of claim 27, wherein the instructions cause the processor to:
select one or more high binding affinity ligand-target complex models based on the one or more binding affinity scores; and
provide the one or more high binding affinity ligand-target complex models for use in designing the custom biologic structure.

29. The method of claim 28, wherein the instructions cause the processor to compare the one or more binding affinity scores to a threshold value and/or rank the prospective ligand target-complex models according to the one or more determined binding affinity scores.

30. The method of claim 1, wherein, at step (c), determining the interface score for each particular one of the prospective ligand-target complex models comprises:
generating, based on the particular prospective ligand-target complex model, a corresponding representation of a ligand-target interface between the particular prospective ligand and the target, said ligand-target interface comprising the particular amino acid population of the particular prospective ligand and at least a portion of the target located in proximity thereto; and
using the corresponding representation of the ligand-target interface as input to the machine learning model, which determines, as output, the interface score for the particular prospective ligand-target complex model.

* * * * *